(12) United States Patent
Birnberg et al.

(10) Patent No.: US 11,844,754 B2
(45) Date of Patent: *Dec. 19, 2023

(54) METHODS FOR TREATMENT OF PARKINSON'S DISEASE

(71) Applicant: NeuroDerm, Ltd., Rehovot (IL)

(72) Inventors: Tal Birnberg, Rehovot (IL); Shmuel Ben Eliahu, Rehovot (IL); Natalia Vostokova, Rehovot (IL); Danit Finkelshtein Beker, Rehovot (IL); Liat Adar, Rehovot (IL); Itay Perlstein, Philadelphia, PA (US)

(73) Assignee: NeuroDerm, Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/092,688

(22) Filed: Jan. 3, 2023

(65) Prior Publication Data

US 2023/0157985 A1 May 25, 2023

Related U.S. Application Data

(63) Continuation-in-part of application No. 17/720,777, filed on Apr. 14, 2022, which is a continuation of application No. 17/567,473, filed on Jan. 3, 2022, now Pat. No. 11,331,293, which is a continuation-in-part of application No. 17/334,554, filed on May 28, 2021, now Pat. No. 11,213,502.

(60) Provisional application No. 63/296,019, filed on Jan. 3, 2022, provisional application No. 63/114,688, filed on Nov. 17, 2020.

(51) Int. Cl.
A61K 31/198 (2006.01)

(52) U.S. Cl.
CPC .................... *A61K 31/198* (2013.01)

(58) Field of Classification Search
CPC .................................. A61K 31/198
See application file for complete search history.

(56) References Cited

U.S. PATENT DOCUMENTS

| | | |
|---|---|---|
| 3,769,424 A | 10/1973 | Bayne |
| 3,808,317 A | 4/1974 | Hecht et al. |
| 3,936,495 A | 2/1976 | Sullivan, Jr. |

(Continued)

FOREIGN PATENT DOCUMENTS

| | | |
|---|---|---|
| CA | 2143070 A1 | 8/1995 |
| CN | 101022784 A | 8/2007 |

(Continued)

OTHER PUBLICATIONS

Nahata, et al., (2000) "Development of Two Stable Oral Suspensions of Levodopa-Carbidopa for Children with Amblyopia," *J. Pediatric Ophthal. & Strab.*, 37:333-337.

(Continued)

*Primary Examiner* — San Ming R Hui
(74) *Attorney, Agent, or Firm* — Goodwin Procter LLP

(57) ABSTRACT

Disclosed is a method for the treatment of a neurological or movement disorder, e.g., Parkinson's disease, in an individual in need thereof, by parenteral administration of levodopa, a levodopa salt, a levodopa prodrug, or any combination thereof, and a dopa decarboxylase inhibitor (DDCI), such as carbidopa, a carbidopa salt, a carbidopa prodrug, benserazide or any combination thereof, concomitantly with oral administration of levodopa, a DDCI, such as carbidopa, benserazide, or any combination thereof.

29 Claims, 1 Drawing Sheet

(56) References Cited

U.S. PATENT DOCUMENTS

| | | |
|---|---|---|
| 3,961,060 A | 6/1976 | Fuxe |
| 4,035,507 A | 7/1977 | Bodor et al. |
| 4,166,452 A | 9/1979 | Generales, Jr. |
| 4,241,082 A | 12/1980 | Baba et al. |
| 4,256,108 A | 3/1981 | Theeuwes |
| 4,265,874 A | 5/1981 | Bonsen et al. |
| 4,409,233 A | 10/1983 | Tsukada et al. |
| 4,642,316 A | 2/1987 | Fawzi et al. |
| 4,684,666 A | 8/1987 | Haas |
| 4,826,875 A | 5/1989 | Chiesi |
| 4,832,957 A | 5/1989 | Dempski et al. |
| 4,962,223 A | 10/1990 | Cannata et al. |
| 4,963,568 A | 10/1990 | Schoenleber et al. |
| 5,350,769 A | 9/1994 | Kasai et al. |
| 5,861,423 A | 1/1999 | Caldwell et al. |
| 5,877,176 A | 3/1999 | Gross |
| 6,153,615 A | 11/2000 | Gross |
| 6,166,083 A | 12/2000 | Barrett et al. |
| 6,245,917 B1 | 6/2001 | Bosch et al. |
| 6,274,168 B1 | 8/2001 | Addicks et al. |
| 6,348,965 B1 | 2/2002 | Palladino et al. |
| 6,500,867 B1 | 12/2002 | Virkki et al. |
| 6,620,432 B2 | 9/2003 | Addicks et al. |
| 6,716,452 B1 | 4/2004 | Piccariello et al. |
| 6,746,688 B1 | 6/2004 | Kushnir et al. |
| 6,797,732 B2 | 9/2004 | Virkki et al. |
| 6,878,529 B2 | 4/2005 | Harrow et al. |
| 6,974,591 B2 | 12/2005 | Kendrup et al. |
| 7,201,923 B1 | 4/2007 | van Lengerich |
| 7,223,776 B2 | 5/2007 | Surivet et al. |
| 7,309,719 B1 | 12/2007 | Aomatsu |
| 7,479,498 B2 | 1/2009 | Keller |
| 7,560,100 B2 | 7/2009 | Pinchasi et al. |
| 7,589,233 B2 | 9/2009 | Chandran |
| 7,709,494 B2 | 5/2010 | Defossa et al. |
| 7,863,336 B2 | 1/2011 | Yacoby-Zeevi et al. |
| 8,048,926 B2 | 11/2011 | Atlas |
| 8,058,243 B2 | 11/2011 | Tyers et al. |
| 8,173,840 B2 | 5/2012 | Chandran |
| 8,193,243 B2 | 6/2012 | Yacoby-Zeevi et al. |
| 8,207,369 B2 | 6/2012 | Stein et al. |
| 8,263,125 B2 | 9/2012 | Vaya et al. |
| 8,273,731 B2 | 9/2012 | Heldman |
| 8,815,950 B2 | 8/2014 | Remenar et al. |
| 8,921,356 B2 | 12/2014 | Heldman |
| 9,040,577 B2 | 5/2015 | Yacoby-Zeevi et al. |
| 9,040,578 B2 | 5/2015 | Yacoby-Zeevi et al. |
| 9,040,589 B2 | 5/2015 | Yacoby-Zeevi et al. |
| 9,040,590 B2 | 5/2015 | Yacoby-Zeevi et al. |
| 9,101,663 B2 | 8/2015 | Yacoby-Zeevi et al. |
| 9,381,249 B2 | 7/2016 | Yacoby-Zeevi et al. |
| 9,415,108 B2 | 8/2016 | Yacoby-Zeevi et al. |
| 9,421,267 B2 | 8/2016 | Yacoby-Zeevi et al. |
| 9,993,451 B2 | 6/2018 | Yacoby-Zeevi et al. |
| 10,022,320 B2 | 7/2018 | Yacoby-Zeevi |
| 10,258,585 B2 | 4/2019 | Yacoby-Zeevi |
| 10,624,839 B2 | 4/2020 | Yacoby-Zeevi |
| 10,813,902 B2 | 10/2020 | Yacoby-Zeevi |
| 11,213,502 B1 | 1/2022 | Birnberg et al. |
| 11,331,293 B1 | 5/2022 | Birnberg et al. |
| 11,458,115 B2 | 10/2022 | Birnberg et al. |
| 2001/0043945 A1 | 11/2001 | Addicks et al. |
| 2002/0028799 A1 | 3/2002 | Naylor et al. |
| 2002/0099013 A1 | 7/2002 | Piccariello et al. |
| 2002/0102707 A1 | 8/2002 | Harrow et al. |
| 2003/0119714 A1 | 6/2003 | Naylor et al. |
| 2003/0152628 A1 | 8/2003 | Licht et al. |
| 2004/0039033 A1 | 2/2004 | Atwal et al. |
| 2005/0038023 A1 | 2/2005 | Bebbington et al. |
| 2005/0053669 A1 | 3/2005 | Friedl et al. |
| 2005/0070608 A1 | 3/2005 | Remenar et al. |
| 2005/0163850 A1 | 7/2005 | Wong et al. |
| 2005/0163859 A1 | 7/2005 | Murthy et al. |
| 2005/0233945 A1 | 10/2005 | Brown et al. |
| 2006/0025385 A1 | 2/2006 | Atlas |
| 2006/0041014 A1 | 2/2006 | Naylor et al. |
| 2006/0088607 A1 | 4/2006 | Stefano et al. |
| 2006/0159751 A1 | 7/2006 | Gogia et al. |
| 2006/0241183 A1 | 10/2006 | Karoum |
| 2007/0191428 A1 | 8/2007 | Rao et al. |
| 2008/0051459 A1 | 2/2008 | Nyholm et al. |
| 2008/0139655 A1 | 6/2008 | Bortz et al. |
| 2008/0187590 A1 | 8/2008 | Vahervuo |
| 2008/0255235 A1 | 10/2008 | Segrell |
| 2010/0298428 A1 | 11/2010 | Yacoby-Zeevi et al. |
| 2010/0298429 A1 | 11/2010 | Yacoby-Zeevi et al. |
| 2011/0269833 A1 | 11/2011 | Yacoby-Zeevi et al. |
| 2011/0294889 A1 | 12/2011 | Segrell |
| 2012/0115823 A1 | 5/2012 | Price et al. |
| 2013/0116215 A1 | 5/2013 | Coma et al. |
| 2013/0123485 A1 | 5/2013 | Park et al. |
| 2013/0253056 A1 | 9/2013 | Nemas et al. |
| 2013/0338143 A1 | 12/2013 | Yacoby-Zeevi et al. |
| 2014/0051755 A1 | 2/2014 | Yacoby-Zeevi et al. |
| 2014/0088192 A1 | 3/2014 | Heller et al. |
| 2014/0249228 A1 | 9/2014 | Yacoby-Zeevi et al. |
| 2014/0249229 A1 | 9/2014 | Yacoby-Zeevi et al. |
| 2014/0249230 A1 | 9/2014 | Yacoby-Zeevi et al. |
| 2014/0249231 A1 | 9/2014 | Yacoby-Zeevi et al. |
| 2015/0217046 A1 | 8/2015 | Heller et al. |
| 2015/0352212 A1 | 12/2015 | Yacoby-Zeevi et al. |
| 2016/0022573 A1 | 1/2016 | Yacoby-Zeevi |
| 2016/0106765 A1 | 4/2016 | Cardinal-David et al. |
| 2016/0151317 A1 | 6/2016 | Yacoby-Zeevi et al. |
| 2017/0157077 A1 | 6/2017 | Yacoby-Zeevi et al. |
| 2017/0157079 A1 | 6/2017 | Yacoby-Zeevi |
| 2017/0196828 A1 | 7/2017 | Yacoby-Zeevi et al. |
| 2017/0296491 A1 | 10/2017 | Yacoby-Zeevi et al. |
| 2019/0125708 A1 | 5/2019 | Yacoby-Zeevi et al. |
| 2019/0151233 A1 | 5/2019 | Yacoby-Zeevi |
| 2020/0397730 A1 | 12/2020 | Yacoby-Zeevi et al. |
| 2021/0000777 A1 | 1/2021 | Yacoby-Zeevi |
| 2021/0038505 A1 | 2/2021 | Yacoby-Zeevi |
| 2021/0077442 A1 | 3/2021 | Yacoby-Zeevi et al. |
| 2021/0093560 A1 | 4/2021 | Yacoby-Zeevi |
| 2022/0151965 A1 | 5/2022 | Birnberg et al. |

FOREIGN PATENT DOCUMENTS

| | | |
|---|---|---|
| CN | 101669925 A | 3/2010 |
| CN | 110294789 A | 10/2019 |
| DE | 2838232 A1 | 3/1979 |
| EP | 0393781 A2 | 10/1990 |
| EP | 1077692 A1 | 2/2001 |
| EP | 1462101 A1 | 9/2004 |
| EP | 2656856 A2 | 10/2013 |
| IN | 244675 B | 12/2010 |
| IN | 251149 B | 2/2012 |
| JP | 54-50700 A | 4/1979 |
| JP | S56115749 | 9/1981 |
| WO | WO-1984/01501 A1 | 4/1984 |
| WO | WO-1996/037226 A2 | 11/1996 |
| WO | WO-1998/016208 A1 | 4/1998 |
| WO | WO-2000/054773 A1 | 9/2000 |
| WO | WO-2001/001984 A1 | 1/2001 |
| WO | WO-2004069146 A2 | 8/2004 |
| WO | WO-2005/099678 A1 | 10/2005 |
| WO | WO-2006/006929 A1 | 1/2006 |
| WO | WO-2006043532 | 4/2006 |
| WO | WO-2007/138086 A1 | 12/2007 |
| WO | WO-2008/124330 A2 | 10/2008 |
| WO | WO-2010027340 A1 | 3/2010 |
| WO | WO-2010/055133 A1 | 5/2010 |
| WO | WO-2010/134074 A1 | 11/2010 |
| WO | WO-2012/006959 A1 | 1/2012 |
| WO | WO-2012/066538 A1 | 5/2012 |
| WO | WO-2014/141261 A1 | 9/2014 |
| WO | WO-2015/136538 A1 | 9/2015 |
| WO | WO-2017/090039 A2 | 6/2017 |
| WO | WO-2018/154447 A1 | 8/2018 |
| WO | WO-2019/038637 A1 | 2/2019 |
| WO | WO-2019/038638 A1 | 2/2019 |

(56) References Cited

FOREIGN PATENT DOCUMENTS

| WO | WO-2019/038639 A1 | 2/2019 |
|---|---|---|
| WO | WO-2020075023 A2 | 4/2020 |

OTHER PUBLICATIONS

International Search Report for PCT/IL2015/050258, dated Aug. 13, 2015 (3 pages).
MacEwen, et al., (1981) "Chronic Inhalation Toxicity of Hydrazine: Oncogenic Effects," Air Force Aerospace Medical Research Laboratory, pp. 1-67.
Pappert, et al., (1997) "Clinical/Scientific Notes—The Stability of Carbidopa in Solution," Movement Disorders, vol. 12, pp. 608-623.
Stocchi et al., (2005), "Intermittent vs Continuous Levodopa Administration in Patients With Advanced Parkinson Disease," Arch Neurol, vol. 62, pp. 905-910.
Ahtila S et al., (1995) 'Effect of Entacapone, a COMT Inhibitor, on the Pharmacokinetics and metabolism of Levodopa After Administration of Controlled-Release Levodopa-Carbidopa in Volunteers,' Clin Neuropharmacol, 18(1):46-57.
Ingman, K et al., (2012) 'The Effect of Different Dosing Regimens of Levodopa/Carbidopa/Entacapone on Plasma Levodopa Concentrations,' Eur J Clin Pharmacol, 68:281-289.
Diederich C et al., (1997), 'Effects of L-DOPA/Carbidopa Administration on the Levels of L-DOPA, Other Amino Acids and Related Compounds in the Plasma, Brain and Heart of the Rat,' Pharmacology, 55(3):109-16.
Mashkovsky, M.D., (2012) "Pharmaceuticals" 16th Edition. Moscow, New wave. 1 page. (Abstract only).
Kharkevich, D.A., (1996) "Pharmacology M., Medicine." 1 page. (Abstract only).
Office action dated Dec. 27, 2017, issued in connection with Russian Patent Application No. 2015143112 (13 pages).
Jog et al. (2008) 'Naturalistic Evaluation of Entacapone in Patients with Signs and Symptons of L-Dopa Wearing-Off,' Current Medical Research and Opinions, 24:11, 3207-3215.
Gordon, M., et al., (2007) "Intravenous Levodopa Administration in Humans Based on a Two-Compartment Kinetic Model," *J. Neuroscience Methods*, 159: 300-307.
Hirano, et al., (2008) "Arginine Increases the Solubility of Coumarin: Comparison with Salting-in and Salting-out Additives," *J. Biochem*, 144 (3): 363-369.
International Search Report for PCT/IL2010/000400, dated Jul. 29, 2010, 4 pages.
International Search Report for PCT/IL2011/000881, dated Apr. 3, 2012, 5 pages.
International Search Report for PCT/IL2014/050261, dated May 30, 2014, 4 pages.
Martinez, et al., (1999) "Hypothesis: Can N-Acetylcysteine Be Beneficial in Parkinson's Disease?" Life Sciences, 64(15):1253-1257.
Mehlisch, et al., (2002) "A Controlled Comparative Study of Ibuprofen Arginate Versus Conventional Ibuprofen in the Treatment of Postoperative Dental Pain," *J. Clin. Pharmacol*., 42: 904-911.
Nord, M. et al., (2010) "The Effect of Peripheral Enzyme Inhibitors on Levodopa Concentrations in Blood and CSF," *Movement Disorders*, 25(3): 363-367.
Nutt JG, (2008), 'Pharmacokinetics and Pharmacodynamics of Levodopa,' *Mov. Disord*., S580-4.
Nutt, et al., (1997) "Motor Fluctuations During Continuous Levodopa Infusions in Patients with Parkinson's Disease," *Movement Disorders*, 12(3):285-292.
Nyholm, D. (2006) "Enteral Levodopa/Carbidopa Gel Infusion for the Treatment of Motor Fluctuations and Dyskinesias in Advanced Parkinson's Disease," *Expert Review of Neurotherapeutics*, 6(10): 1403-1411.
Nyholm, D., et al., (2012) "Levodopa Infusion Combined with Entacapone or Tolcapone in Parkinson Disease: a Pilot Trial," *European Journal of Neurology*, 19: 820-826.

Olanow, C.W. (2008) "Levopoda/Dopamine Replacement Strategies in Parkinson's Disease—Future Directions," *Movement Disorders*, 23:S613-S622.
Pardo, et al., (1993) "Ascorbic acid protects against levodopa-induced neurotoxicity on a catecholamine-rich human neuroblastoma cell line", *Mov. Disord*., 8(3):278-284. (Abstract Only).
Redenti, et al., (2001) "Cyclodextrin Complexes of Salts of Acidic Drugs. Thermodynamic Properties, Structural Features, and Pharmaceutical Applications," *Journal of Pharmaceutical Sciences*, 90(8): 979-986.
Steiger, M., et al., (1991) "The Clinical Efficacy of Oral Levodopa Methyl Ester Solution in Reversing Afternoon "Off" Periods in Parkinson's Disease," Clin. Neuropharmacol., 14:241-244.
Tsumoto, K., et al., (2004) "Role of Arginine in Protein Refolding, Solubilization, and Purification," *Biotechnol. Prog*., 20:1301-1308.
Umezawa H., et al., (1975) "Isolation of Isoflavones Inhibiting Dopa Decarboxylase From Fungi and Streptomyces," J Antibiot, 28(12):947-52.
Written Opinion for International Application No. PCT/IL2015/050258, dated Aug. 13, 2015 (6 pages).
Written Opinion of the International Search Authority for PCT/IL2010/000400 dated Jul. 29, 2010, 8 pages.
Written Opinion of the International Search Authority for PCT/IL2011/000881 dated Apr. 3, 2012, 6 pages.
Written Opinion of the International Search Authority for PCT/IL2014/050261 dated May 30, 2014, 5 pages.
Yacoby-Zeevi, O., et al. (2010) "Markedly Enhanced Levodopa Pharmacokinetics from Continuous Subcutaneous Carbidopa Administration," *European Journal of Neurology*, 17 (Suppl. 3): 52.
Roche Products (New Zealand) Limited. (2015) "Madopar Consumer Medicine Information." 1-9.
International Search Report for PCT/IL2016/051261, dated May 29, 2017 (6 pages).
Written Opinion of the International Searching Authority for PCT/IL2016/051261, dated May 29, 2017 (14 pages).
Food and Drug Administration (2008) "NDA 17-555/S-069: Sinemet (Carbidopa-Levodopa) Tablets," [online] Retrieved from the internet on Jun. 20, 2018, at: http://www.accessdata.fda.gov/drugsatfda_docs/label/2008/017555s069lbl.pdf (13 pages).
Kurth, MC (1997) 'Using Liquid Levodopa in the Treatment of Parkinson's Disease. A Practical Guide,' Drugs & Aging, 10 (5): 332-340.
López Lozano, JJ et al., (1995) 'Preparation of a Levodopa/Carbidopa Solution in Ascorbic Acid (Citridopa) and Chromatographic and Electrochemical Assessment of its Stability over 24 Hours,' Neurologia 10:155-158 (Abstract only).
Office Action dated Sep. 12, 2018, issued in connection with Russian Patent Application No. 2016135952 (12 pages).
Anonymous, (2002), "Levodopa: Management of Parkinson's Disease," Mov Disord, 17(Suppl 4); S23-S37.
Atlas D, (2016), "DopAmide: Novel, Water-Soluble, Slow-Release l-dihydroxyphenylalanine (l-DOPA) Precursor Moderates l-DOPA Conversion to Dopamine and Generates a Sustained Level of Dopamine at Dopaminergic Neurons," CNS Neurosci Ther, 22(6):461-7.
Chun IK et al., (2011), "Design and Evaluation of Levodopa Methyl Ester Intranasal Delivery Systems," J Parkinsons Dis, 1 (1):101-7.
Di Stefano A et al., (2009), "New Drug Delivery Strategies for Improved Parkinson's Disease Therapy," Expert Opin Drug Deliv, 6(4):389-404.
International Search Report for International Application No. PCT/IB2018/051048, dated May 21, 2018 (3 pages).
Written Opinion of the International Searching Authority for International Application No. PCT/IB2018/051048, dated May 21, 2018 (7 pages).
International Search Report for International Application No. PCT/IL04/00103, dated Aug. 7, 2006 (3 pages).
Written Opinion of the International Searching Authority for International Application No. PCT/IL04/00103, dated Aug. 7, 2006 (4 pages).

(56) References Cited

OTHER PUBLICATIONS

"Duodopa Intestinal Gel," Electronic Medicines Compendium, XP-022724129, retrieved from https://www.medicines.org.uk/emc/medicine/20786/SPC/Duodopa+intestinal+gel/#composition on Sep. 5, 2014 (2013), 7 pages.
National Institutes of Health (2010) 'Pharmacokinetics of Levodopa/Carbidopa Infusion With and Without Oral Catechol-O-Methyl Transferase (COMT) Inhibitors (DuoCOMT),' U.S. National Library of Medicine, Clinical Trials.gov, Clinical Trials.gov Identifier: NCT 00906828, XP-002724128, retrieved from URL://http://clinicaltrials.gov/ct2/show/NCT00906828 on Sep. 5, 2014 (3 pages).
Paulekuhn, GS, et al. (2007) "Trends in Active Pharmaceutical Ingredient Salt Selection based on Analysis of the Orange Book Database," *Journal of Medicinal Chemistry, American Chemical Society*, 50(26):6665-6672.
Banerjee, RC, (1979) "Aminonitriles and Aminothioamides Related to Natural Amino Acids," *International Journal of Peptide and Protein Res.* 14(3):234-46.
Elder D., et al., (2013) "Use of Pharmaceutical Salts and Cocrystals to Address the Issue of Poor Solubility," *International Journal of Pharmaceutics*, 453(1):88-100.
Hilfiker et al., "Relevance of Solid-state Properties for Pharmaceutical Products" in *Polymorphism: in the Pharmaceutical Industry*, p. 1-19 (Ed. Hilfiker, Wiley-VCH Verlag Gmbh & Co. KGaA, Weinheim, 2006).
Written Opinion of the International Searching Authority for International Application No. PCT/IB2018/056125, dated Jan. 14, 2019 (10 pages).
International Search Report for International Application No. PCT/IB2018/056125, dated Jan. 14, 2019 (5 pages).
Written Opinion of the International Searching Authority for International Application No. PCT/IB2018/056126, dated Nov. 26, 2018 (10 pages).
International Search Report for International Application No. PCT/IB2018/056126, dated Nov. 26, 2018 (4 pages).
Written Opinion of the International Searching Authority for International Application No. PCT/IB2018/056127, dated Nov. 26, 2018 (7 pages).
International Search Report for International Application No. PCT/IB2018/056127, dated Nov. 26, 2018 (4 pages).
Aldea G, et al., (2004) Abstract 15, entitled "Comparison of the speed of absorption of S(+)-ibuprofen in two pharmaceutical specialties: ibuprofen (arginate) and dexibuprofen" in *Abstract Pamphlet for the XIX Congress of the Spanish Society of Clinical Pharmacology*, XIX Congress of the Spanish Society of Clinical Pharmacology, Oct. 28-30, 2004, Santander, Spain (54 pages).
Levin, O.S. (2008) "Diagnosis and treatment of restless legs syndrome" *Attending Physician* 5(8) (retrieved Jul. 8, 2019, from the internet at <<https://www.lvrach.ru/2008/05/5154263/>> (10 pages).
Technology of Dosage Forms, in *Medicine*, vol. 1, §10.3, p. 187-91, and §14.2, p. 223-4 (Ed. T.S. Kondrat'eva, Moscow, 1991)(7 pages; English language translation of Office Action citing reference provided as English language translation of Official Action issued in connection with Russian Patent Application No. 2011149976/15, dated Sep. 15, 2014 (6 p. Cite No. C68).
"Dihydroxyphenylalanine" PubmChem CID No. 6971033, (retrieved on Jul. 8, 2019, from the internet at <<https://pubchem.ncbi.nlm.nih.gov/compound/6971033>>)(24 pages).
"Levodopa," in *Encyclopedia of Drugs*, p. 471 (Moscow, RLS, 2001)(2 pages; English language translation of Office Action citing reference provided as English language translation of Official Action issued in connection with Russian Patent Application No. 2011149976/15, dated Sep. 15, 2014 (6 pages). Cite No. C68.
English language translation of Official Action issued in connection with Russian Patent Application No. 2011149976/15, dated Sep. 15, 2014 (6 pages).
CAPLUS Registry No. 34996-80-0 (1984)) retrieved from CAPLUS on May 16, 2008 (1 page).
CAPLUS Registry No. 73148-96-6 (1984), retrieved from CAPLUS database on May 16, 2008 (1 page).
CAPLUS Registry No. 120346-34-1 (1989), retrieved from CAPLUS on May 16, 2008 (2 pages).
Roche Products Limited (2016) "Madopar 50 mg/12.5 mg Dispersible Tablets, Summary of Product Characteristics" Updated Mar. 17, 2016 (9 pages).
Roche Products Limited (2016) "Madopar 100 mg/25 mg Dispersible Tablets, Summary of Product Characteristics" Updated Mar. 17, 2016 (9 pages).
Roche Products Limited (2015) "Package leaflet: Information for the patient" Updated Mar. 2015 (6 pages).
"New Zealand standardised formulation batch sheet, Carbidopa/Levodopa (Sinemet®) suspension" (2010) Last updated Dec. 2010 (1 page).
Nationwide Children's Hospital (2010) "Levodopa/Carbidopa Oral Suspension 5mg-1.25mg/mL" (1 page).
AbbVie Ltd (2017) "Duodopa intestinal gel, Summary of Product Characteristics" Updated Dec. 5, 2017 (12 pages).
Merck Sharp & Dohme Limited (2019) "Sinemet 12.5mg/50mg Tablets, Summary of Product Characteristics" Updated Feb. 1, 2019 (7 pages).
Pharminfotech (2011) "Formulation in Pharmacy Practice—eMixt: Levodopa/Carbidopa" Updated Sep. 2011 (retrieved from <http://www.pharminfotech.co.nz/maual/Formulation/mixtures/levodopa/htm> on Apr. 8, 2019)(1 page).
"Mutschler Arzneimittelwirkungen" p. 322-5 (Ernst Mutschler et al. eds., Wissenschaftliche Verlagsgesellschaft mbH, 2008)(Cited in Decision rejecting the opposition of European Patent No. 2 432 454, dated Aug. 26, 2019)(6 pages).
European Patent Office, Opposition Division "Decision rejecting the opposition of European Patent No. 2 432 454" dated Aug. 26, 2019 (13 pages).
S. Mondal "Basic Undergraduate Pharmacology" p. 280 (Academic Publishers, Mar. 2010) (3 pages).
Kurth et al., (1993) "Oral levodopa/carbidopa solution versus tablets in Parkinson's patients with severe fluctuations: A pilot study," *Neurology* 43:1036-9.
J. E. Ahlskog "Parkinson's Disease Treatment Guide for Physicians" p. 179-81 (Oxford University Press, 2009) (6 pages).
U. Moser "Arzneibuch-Kommentar" p. C18 (Wissenschaftliche Verlagsgesellschaft mbH, 1993)(Cited in Decision rejecting the opposition of European Patent No. 2 432 454, dated Aug. 26, 2019)(2 pages).
L. Braiman-Wiksman (2018) "Experimental Report, A. Stability Testing" p. 1-7.
"Mutschler Arzneimittelwirkungen: Lehrbuch der Pharmakologie und Toxikologie" p. 327 (Ernst Mutschler et al. eds., Wissenschaftliche Verlagsgesellschaft mbH, 2008)(Cited in Decision rejecting the opposition of European Patent No. 2 432 454, dated Aug. 26, 2019)(3 pages).
"The Merck Index: an Encyclopedia of Chemicals, Drugs, and Biologicals" p. xv and 784-5 (M. Windholz et al. eds., Merck & Co., Inc., 10th edition, 1983)(4 pages).
Appendices II and III, submitted to the European Patent Office on Mar. 16, 2016 in connection with European Application No. EP10725880.8, and cited in the Decision rejecting the opposition of European Patent No. 2 432 454, dated Aug. 26, 2019 (3 pages).
Nagayama, et al. (2004) "The Effect of Ascorbic Acid on the Pharmacokinetics of Levodopa in Elderly Patients with Parkinson Disease," *Clin Neuropharmacol*, 27(6):270-3.
"Pharmacokinetics of Levodopa/Carbidopa Infusion With and Without Oral Catechol-0-methyl Transferase (COMT) Inhibitors", Internet, Jan. 2010 (Jan. 2010).
Extended European Search Report (EESR) for EP 20150020, dated May 14, 2020, 11 pages.
Notification of the Second Office Action dated May 25, 2021 for Chinese Application No. 201910369050.X.
Notification of Office Action dated Apr. 23, 2021 for Canadian Application No. 2,942,244.
Ramot et al., "Ninety-day Local Tolerability and Toxicity Study of ND0612, a Novel Formulation of Levodopa/Carbidopa, Administered by Subcutaneous Continuous Infusion in Minipigs" *Toxicologic Pathology* 2017, vol. 45(6) 764-773.

(56) References Cited

OTHER PUBLICATIONS

"History of Changes for Study: NCT02782481: A Clinical Study Investigating the Efficacy, Tolerability, and Safety of Continuous Subcutaneous ND0612 Infusion Given a Treatment to Oral Levodopa in Patients With Parkinson's Disease With Motor Fluctuations" NIH U.S. National Library of Medicine, (History of Changes for Study: NCT02782481 (clinicaltrials.gov) <https://clinicaltrials.gov/ct2/history/NCT02782481>, submitted Dec. 9, 2019, downloaded from ClinicalTrials.gov on Jan. 31, 2022.
International Search Report for PCT/IL2021/051355, dated Jan. 20, 2022.
Written Opinion of the International Search Authority for PCT/IL2021/051355, dated Jan. 20, 2022.
Zhou, et al. (2010) "Design, Synthesis and Biological Evaluation of l-dopa Amide Derivatives as Potential Prodrugs for the Treatment of Parkinson's Disease," *European Journal of Medical Chemistry*, 45(9):4035-4042.
Produodopa Summary of Product characteristics, downloaded from <https://www.hpra.ie/img/uploaded/swedocuments/Licence_PA1824-002-003_28092022110832.pdf%20>, dated Sep. 28, 2022, 16 pages.
Produodopa Package Leaflet, downloaded from https://www.hpra.ie/img/uploaded/swedocuments/b1bc0aa4-a554-4276-b7a0-27e0ed4cc2be.pdf<%20https:/www.hpra.ie/img/uploaded/swedocuments/b1bc0aa4-a554-4276-b7a0-27e0ed4cc2be.pdf%20>, 14 pages.
Solieau et al. (2022) "Safety and efficacy of continuous subcutaneous foslevodopa-foscarbidopa in patients with advanced Parkinson's disease: a randomized, double-blind, active-controlled, phase 3 trial," Lancet Neurology 21:1099-1109.
U.S. Appl. No. 12/781,357, Continuous Administration of Dopa Decarboxylase Inhibitors and Compositions for Same, filed May 17, 2010, Granted, U.S. Pat. No. 8,193,243.
U.S. Appl. No. 12/836,130, filed Jul. 14, 2010, Granted, U.S. Pat. No. 7,863,336.
U.S. Appl. No. 12/961,534, filed Dec. 7, 2010, Granted, U.S. Pat. No. 9,101,663.
U.S. Appl. No. 13/796,232, filed Mar. 12, 2013, Abandoned, 20130253056.
U.S. Appl. No. 14/276,211, filed May 13, 2014, Granted, U.S. Pat. No. 9,040,589.
U.S. Appl. No. 14/276,235, filed May 13, 2014, Granted, U.S. Pat. No. 9,040,590.
U.S. Appl. No. 14/789,214, filed Jul. 1, 2015, Granted, U.S. Pat. No. 9,993,451.
U.S. Appl. No. 15/244,326, filed Aug. 23, 2016, Abandoned, 20170196828.
U.S. Appl. No. 15/992,979, filed May 30, 2018, Abandoned, 20190125708.
U.S. Appl. No. 16/863,459, filed Apr. 30, 2020, Abandoned, 20210077442.
U.S. Appl. No. 17/985,556, filed Nov. 11, 2022, Pending.
U.S. Appl. No. 13/885,518, Continuous Administration of L-Dopa, Dopa Decarboxylase Inhibitors, Catechol-O-Methyl Transferase Inhibitors and Compositions for Same, filed Oct. 29, 2013, Granted, U.S. Pat. No. 9,421,267.
U.S. Appl. No. 14/243,625, filed Apr. 2, 2014, Granted, U.S. Pat. No. 9,040,577.
U.S. Appl. No. 14/243,638, filed Apr. 2, 2014, Granted, U.S. Pat. No. 9,040,578.
U.S. Appl. No. 15/209,423, filed Jul. 13, 2016, Abandoned, 20170157077.
U.S. Appl. No. 16/749,435, filed Jan. 22, 2020, Abandoned, 20200397730.
U.S. Appl. No. 17/696,243, filed Mar. 16, 2022, Pending.
U.S. Appl. No. 14/774,938, Method for Treatment of Parkinson'S Disease, filed Sep. 11, 2015, Abandoned, 20160022573.
U.S. Appl. No. 16/876,911, filed May 18, 2020, Abandoned, 20210093560.
U.S. Appl. No. 17/698,189, filed Mar. 18, 2022, Pending.
U.S. Appl. No. 14/645,848, Dopa Decarboxylase Inhibitor Compositions, filed Mar. 12, 2015, Granted, U.S. Pat. No. 10,022,320.
U.S. Appl. No. 15/438,472, filed Feb. 21, 2017, Granted, U.S. Pat. No. 10,258,585.
U.S. Appl. No. 16/008,228, filed Jun. 14, 2018, Granted, U.S. Pat. No. 10,624,839.
U.S. Appl. No. 16/353,544, filed Mar. 14, 2019, Granted, U.S. Pat. No. 10,813,902.
U.S. Appl. No. 16/819,740, filed Mar. 16, 2020, Abandoned, 20210038505.
U.S. Appl. No. 17/901,078, filed Sep. 1, 2022, Pending.
U.S. Appl. No. 17/031,479, filed Sep. 24, 2020, Abandoned, 20210000777.
U.S. Appl. No. 17/740,698, filed May 10, 2022, Pending.
U.S. Appl. No. 15/360,165, Pharmaceutical Compositions Comprising Levodopa Amide and Uses Thereof, filed Nov. 23, 2016, Abandoned, 20170296491.
U.S. Appl. No. 17/334,554, Method for Treatment of Parkinson's Disease May 28, 2021, Granted, U.S. Pat. No. 11,213,502.
U.S. Appl. No. 17/533,984, filed Nov. 23, 2021, Pending, 20220151965.
U.S. Appl. No. 17/567,473, filed Jan. 3, 2022, Granted, U.S. Pat. No. 11,331,293.
U.S. Appl. No. 17/720,777, filed Apr. 14, 2022, Pending.
U.S. Appl. No. 17/736,494, filed May 4, 2022, Granted, U.S. Pat. No. 11,458,115.
Felix AM et al., "Synthesis and antireserpine activity of peptides of L-dopa" J. Med. Chem. 17(4): 422-426 (1974).
Bodor, N. et al., "Improved delivery through biological membranes. 4. Prodrugs of L-Dopa" J. Med. Chem. 20(11) :1435-1445 (1977).
Wang et al., "Systemic and brain bioavailabilities of D-phenylglycine-L-Dopa. a sustained dopamine-releasing prodrug" Journal of Food and Drug Analysis. Jun I; 21(2):136-41 (2013).
Ichinose H. et al., "Increase of catecholamines in mouse brain by systemic administration of gamma-glutamyl L-3,4-dihydroxyphenylalanine" Journal of Neurochemistry. Sep. 49(3):928-32 (1987).
Shevchenko VP. et al. "Synthesis of isotopically modified derivatives of dopamine. serotonin. and doxorubicin with Boe-Pro and Boc-[2H] Pro" Doklady Akademii Nauk. Khimiya. Mar. vol. 485. No. 1. pp. 87-90 (2019). (in Russian).
CAS Registry No. 2305269-90-. CA Index Name: tyrosine. 3-methoxy-N-[2-(1-methylethoxy)acetyl]-. Entered STN: Apr. 27, 2019.
Hoon M. et al. "The Design and evaluation of an L-Dopa-lazabemide prodrug for the treatment of Parkinson's disease" Molecules. Dec.; 22(12):2076 (2017).
Durso R, et al. "Variable absorption of carbidopa affects both peripheral and central levodopa metabolism" The Journal of Clinical Pharmacology. Aug. 40(8):854-60 (2000).
International Search Report for International Application No. PCT/IL2022/050269, dated Jun. 16, 2022 (6 pages).
Written Opinion of the International Search Authority for PCT/IL2022/050269 dated Jun. 16, 2022, 14 pages.
Shaltiel-Karyo et al., "Subcutaneous Administration of Carbidopa Enhances Oral Levodopa Pharmacokinetics: A Series of Studies Conducted in Pigs, Mice, and Healthy Volunteers" Clinical Neuropharmacology, 42(4):111-116 (2019).

METHODS FOR TREATMENT OF PARKINSON'S DISEASE

CROSS REFERENCE TO RELATED APPLICATIONS

This application claims the benefit of and priority to U.S. Provisional Patent Application No. 63/296,019, filed Jan. 3, 2022; and is a continuation-in-part of U.S. patent application Ser. No. 17/720,777, filed Apr. 14, 2022, which is a continuation of U.S. patent application Ser. No. 17/567,473, filed Jan. 3, 2022 and issued as U.S. Pat. No. 11,331,293, which is a continuation-in-part of U.S. patent application Ser. No. 17/334,554, filed May 28, 2021 and issued as U.S. Pat. No. 11,213,502, which claims the benefit of and priority to U.S. Provisional Patent Application No. 63/114,688, filed Nov. 17, 2020, the disclosure of each of which is incorporated by reference herein in its entirety.

TECHNICAL FIELD

The present invention provides a method for treatment of neurological or movement disorders such as Parkinson's disease by parenteral administration of levodopa or prodrug thereof and a dopa decarboxylase inhibitor (DDCI) or prodrug thereof, such as carbidopa, benserazide, or any combination thereof, concomitantly with oral administration of levodopa or prodrug thereof, a dopa decarboxylase inhibitor (DDCI) or prodrug thereof, such as carbidopa, benserazide, or any combination thereof.

BACKGROUND

Parkinson's disease is a degenerative condition characterized by reduced concentration of the neurotransmitter dopamine in the brain. Levodopa (L-dopa or L-3,4-dihydroxyphenylalanine) is an immediate metabolic precursor of dopamine that, unlike dopamine, is able to cross the blood-brain barrier, and is most commonly used for restoring the dopamine concentration in the brain. For the past 40 years, levodopa has remained the most effective therapy for the treatment of Parkinson's disease.

However, levodopa has a short half-life in plasma that, even under best common current standard of care, results in pulsatile dopaminergic stimulation. Long-term therapy is therefore complicated by motor fluctuations and dyskinesia that can represent a source of significant disability for certain patients. A therapeutic strategy that could ultimately deliver levodopa/dopamine to the brain in a more continuous and physiologic manner would provide the benefits of standard levodopa with reduced motor complications and is much needed by patients suffering from Parkinson's disease and other neurological or movement disorders.

SUMMARY OF INVENTION

Provided herein, inter alia, are methods and pharmaceutical compositions for the treatment of a neurological or movement disorder comprising parenteral administration of levodopa, prodrugs or salts thereof (e.g., pharmaceutically acceptable prodrugs or salts thereof), and compositions comprising the same (e.g., pharmaceutically acceptable compositions, for example, liquid pharmaceutical compositions) and a dopa decarboxylase inhibitor (DDCI), prodrugs or salts thereof (e.g., pharmaceutically acceptable prodrugs or salts thereof), and compositions comprising the same (e.g., pharmaceutically acceptable compositions, for example, liquid pharmaceutical compositions) concomitant with oral administration of an active agent selected from the group consisting of levodopa, a levodopa salt, a levodopa prodrug, a dopa decarboxylase inhibitor (DDCI), prodrugs or salts thereof (e.g., pharmaceutically acceptable salts thereof), and compositions comprising the same (e.g., pharmaceutically acceptable compositions, for example, liquid pharmaceutical compositions). Also disclosed is a kit for the administration of the described method and treatment regimens for administration of the described method specified by time course and amount of pharmaceutical composition.

Embodiments of the invention are directed to a method for treatment of Parkinson's disease in a patient in need thereof, said method comprising:
  subcutaneously administering to the patient, over a subcutaneous infusion time course of at least about 24 hours, a pharmaceutically acceptable liquid composition comprising levodopa, a levodopa salt, a levodopa prodrug, or any combination thereof, and carbidopa, a carbidopa salt, a carbidopa prodrug, or any combination thereof, in an amount to deliver about 720 mg of levodopa, the levodopa salt, the levodopa prodrug, or the combination thereof, and about 90 mg of carbidopa, the carbidopa salt, the carbidopa prodrug, or the combination thereof, to the patient over the time course of the at least about 24 hours; and
  orally administering to the patient, before or during the subcutaneous infusion time course, one or more immediate release tablet or capsule comprising 100 mg levodopa.

According to some embodiments, the pharmaceutically acceptable liquid composition further comprises arginine. According to some embodiments, the pharmaceutically acceptable liquid composition further comprises at least one antioxidant. According to some embodiments, the immediate release tablet or capsule further comprises carbidopa.

According to some embodiments, upon the subcutaneous administration and the oral administration, the plasma levodopa area under the curve (AUC) from time 0 to the end of the infusion time of the patient is higher as compared to the combination of i) a plasma levodopa AUC from time 0 to the end of the infusion time when a patient is subcutaneously administered over at least about 24 hours the pharmaceutically acceptable liquid composition alone; and ii) a plasma levodopa AUC of a patient administered with the oral levodopa alone.

Further embodiments of the invention are directed to a method for treatment of Parkinson's disease in a patient in need thereof, said method comprising:
  subcutaneously administering to the patient, over a subcutaneous infusion time course of at least about 24 hours or more, a first pharmaceutically acceptable liquid composition comprising: levodopa, carbidopa, arginine, and an antioxidant, in an amount to deliver about 720 mg of levodopa and about 90 mg of carbidopa to the patient over the course of at least about 24 hours; and
  orally administering to the patient, before or during the subcutaneous infusion time course, at least one oral dosage form comprising levodopa.

According to some embodiments, the oral dosage form includes one of: 50 mg levodopa, 75 mg levodopa, 95 mg levodopa, 100 mg levodopa, 125 mg levodopa, 145 mg levodopa, 150 mg levodopa, 195 mg levodopa, 200 mg levodopa, 245 mg levodopa, or 250 mg levodopa.

Further embodiments of the invention are directed to a method for treatment of Parkinson's disease in a patient currently being administered levodopa and carbidopa in the form of oral immediate release levodopa and carbidopa alone, and in need of further treatment, said method comprising:

subcutaneously administering to the patient, over a subcutaneous infusion time course of 24 hours a first pharmaceutically acceptable liquid composition comprising: levodopa, carbidopa, arginine, and an antioxidant, in an amount to deliver about 720 mg of levodopa and about 90 mg of carbidopa to the patient over the course of at least about 24 hours;

orally administering to the patient, before or during the subcutaneous infusion time course, at least one tablet or capsule comprising 100 mg levodopa and 25 mg carbidopa daily.

Disclosed herein is a method for treatment of a neurological or movement disorder in a patient in need thereof, said method comprising: parenterally administering to the patient a first pharmaceutical composition comprising: a) levodopa, a levodopa salt, a levodopa prodrug, or any combination thereof; and b) a dopa decarboxylase inhibitor (DDCI), a DDCI salt, a DDCI prodrug, or any combination thereof; and, concomitantly, orally administering to the patient a second pharmaceutical composition comprising an active agent selected from the group consisting of levodopa, a levodopa salt, a levodopa prodrug, a dopa decarboxylase inhibitor (DDCI), a DDCI salt, a DDCI prodrug, and any combination thereof.

In some embodiments, the method described herein includes a DDCI comprising, consisting of, or consisting essentially of carbidopa, benserazide, or any combination thereof.

In some embodiments, the method described herein includes the same DDCI in the first pharmaceutical composition as the DDCI in the second pharmaceutical composition.

In some embodiments, the method described herein includes a different DDCI in the first pharmaceutical composition as the DDCI in the second pharmaceutical composition.

In some embodiments, the method described herein includes as the second pharmaceutical composition levodopa and a DDCI.

In some embodiments, the method described herein includes the DDCI carbidopa.

In some embodiments, the method described herein includes subcutaneous, transdermal, intradermal, intravenous, intramuscular, intratracheal, intranasal, intrathecal, intragastric or intraduodenal administration of the first pharmaceutical composition.

In some embodiments, the method described herein includes subcutaneous administration of the first pharmaceutical composition.

In some embodiments, the method described herein includes the administration of the pharmaceutical composition to the patient in need thereof via one or more sites.

In some embodiments, the neurological or movement disorder pertaining to the method described herein includes Parkinson's disease; secondary parkinsonism, such as drug-induced secondary parkinsonism, neuroleptic induced parkinsonism, postencephalitic parkinsonism, and vascular parkinsonism; motor fluctuations; neurodegenerative disorders; dyskinesia; reduced dopamine levels in the brain; levodopa induced dyskinesia; rapid eye movement sleep behavior disorder (RBD); dystonia; morning akinesia; tremor symptoms, such as essential tremor and drug-induced tremor; myoclonus; chorea, such as drug induced chorea; tics, such as drug induced tics and organic tics; drug induced movement disorder; drug induced akathisia; restless legs syndrome (RLS); stiff-man syndrome; benign shuddering attacks; malignant neuroleptic syndrome; Huntington's disease; Shy-Drager syndrome; brain injury induced conditions, such as carbon monoxide or manganese intoxication; or any combination thereof; for example, provided herein are methods of treating patients suffering from includes Parkinson's disease.

Generally, physicians assess the severity of Parkinson's disease patients according to objective and subjective signs and symptoms, using, e.g., various scales, and prescribe levodopa dosing administration accordingly. One of the well-known and widely used scales for diagnosing and scaling the severity of Parkinson's disease is the Unified Parkinson's Disease Rating Scale (UPDRS). Modifications of the UPDRS may also be used to classify Parkinson's disease patients. Another known method for measuring the severity of Parkinson's disease is according to the Hoehn and Yahr (H&Y) stages, which includes a scale of 5 stages, in which stages 1-2 are considered to be mild or early-stage Parkinson's disease patients, stage 3 is considered to be moderate or mid-stage Parkinson's disease patients, and stages 4-5 are considered to be advanced Parkinson's disease patients. The daily levodopa dose may be defined and changed by the physician from time to time, according to, e.g., clinical findings as well as "trial and error" methods, according to the particular patient's condition, the response of that patient to the treatment, and the like. Further, the patient may be administered a different daily dose on different days, depending on signs and symptoms, wherein the range of the administered daily dose may be set by the physician, thereby allowing the patient flexibility in treatment. It is noted that physician generally refer to signs as being objective measure and to symptoms as being subjective ones.

According to some embodiments, provided herein are methods of treating advance-stage Parkinson's disease patients. According to some embodiments, provided herein are methods of treating advanced stage and/or moderate Parkinson's disease patients. According to some embodiments, provided herein are methods for treating patients with motor fluctuations. According to some embodiments, provided herein are methods for treating Parkinson's disease patients with motor fluctuations.

According to some embodiments, provided herein are methods of treating Parkinson's disease patients who require a dose of above about 300 mg levodopa/day, above about 400 mg levodopa/day, above about 500 mg levodopa/day, above about 600 mg levodopa/day, above about 700 mg levodopa/day, above about 800 mg levodopa/day, above about 900 mg levodopa/day, above about 1000 mg levodopa/day.

According to some embodiments, provided herein are methods of treating Parkinson's disease patients requiring an elevated dose of levodopa at a particular timepoint, e.g., in the morning, e.g., towards the end (about the last hour) of a low activity/night period, e.g., in the beginning (about the first hour) of a high activity/day period. For instance, according to some embodiments, there may be a certain rate for high activity/day hours and a different rate for low activity/night hours, wherein an elevated dose of levodopa may be administered towards the end of the low activity/night hours, at the end of the low activity/night hours, at the beginning of the high activity/day hours, and the like. Such an elevated dose may be provided by the administration of an oral dose of the second pharmaceutical composition, e.g., at the times referred to above, provided concomitantly with the substantially continuous first pharmaceutical composition.

According to some embodiments, provided herein are methods of treating patients suffering from Parkinson's disease for a period of more than about 4 years, more than about 5 years, more than about 6 years, more than about 7 years, more than about 8 years, more than about 9 years, or more than about 10 years.

According to some embodiments, provided herein are methods of treating Parkinson's disease patients suffering from at least 1 hour, at least 1.5 hours, at least 2 hours, at least 2.5 hours, at least 3 hours, of "off time" per day, wherein "off time" refers to the recurrence of Parkinson's symptoms between medication doses.

In some embodiments, the method described herein includes substantial continuous administration of the first pharmaceutical composition.

In some embodiments, the method described herein includes administration of the second pharmaceutical composition 1, 2, 3, 4, 5, 6, 7, 8, 9 or 10 times a day.

In some embodiments, the method described herein includes administration of the second pharmaceutical composition when symptoms from said neurological or movement disorder require said administration.

In some embodiments, the method described herein includes administration of the second pharmaceutical composition at predefined times, predefined intervals, or both.

In some embodiments, the method described herein includes administration of the second pharmaceutical composition more than once, wherein the administered dose is the same at all administrations.

In some embodiments, the method described herein includes administration of the second pharmaceutical composition more than once, wherein the administered dose differs in at least two administrations.

In some embodiments, the method described herein includes administration of the second pharmaceutical composition in a dose of between about 25 mg and about 400 mg levodopa or a salt or prodrug thereof, in each administration.

In some embodiments, the method described herein includes as the first pharmaceutical composition levodopa, carbidopa and arginine or any salt or prodrug thereof.

In some embodiments, the method described herein includes as the first pharmaceutical composition levodopa, carbidopa, arginine, or any salt or prodrug thereof, and at least one antioxidant.

In some embodiments, the method described herein includes as the first pharmaceutical composition levodopa, carbidopa, arginine, or any salt or prodrug thereof, and at least two antioxidants.

In some embodiments, the method described herein includes as the first pharmaceutical composition a composition that comprises levodopa, carbidopa, or any salt or prodrug thereof, and a base selected from the group consisting of arginine, lysine, NaOH, tris(hydroxymethyl)aminomethane (TRIS), and any combination thereof.

In some embodiments, the method described herein includes as the first pharmaceutical composition a composition with a pH in the range of between about 6 to about 10, in the range of between about 8 to about 10, in the range of about 8 to about 9, in the range of about 8.5 to about 9.5, in the range of between about 9 to about 10, in the range of between about 9.1 to about 9.8, or about 9.5.

In some embodiments, the method described herein includes as the first pharmaceutical composition a composition that comprises between about 1% w/v and about 40% w/v, between about 1% w/v and about 20% w/v, between about 1% w/v and about 10% w/v, between about 2% w/v and about 8% w/v, between about 4% w/v and about 8% w/v, between about 5% w/v and about 7% w/v, between about 10% and 20% w/v, between about 15% to about 25% w/v, between about 20% to about 30% w/v, between about 25% to about 35% w/v, between about 30% to about 40% w/v, about 30% w/v or about 6% w/v of levodopa, a levodopa prodrug, a levodopa salt, or any combination thereof.

In some embodiments, the method described herein includes as the first pharmaceutical composition a composition that comprises between about 0.5% w/v and about 10% w/v, between about 0.5% w/v and about 6% w/v, between about 0.5% w/v and about 4% w/v, between about 0.5% w/v and about 2% w/v, between about 0.5% w/v and about 1% w/v, about 0.75% w/v, about 1.0% w/v, about 1.3% w/v or about 1.5% w/v, of carbidopa, a carbidopa salt, a carbidopa prodrug, or any combination thereof.

In some embodiments, the method described herein includes the antioxidant that is selected from the group consisting of ascorbic acid or a salt thereof, a cysteine, such as N-acetyl cysteine, a bisulfite or a salt thereof, glutathione, a tyrosinase inhibitor, a bivalent cation, butylated hydroxy toluene (BHT), beta hydroxy acid (BHA) tocopherol, gentisic acid, tocopherol, tocopherol derivative, thioglycerol, and any combination thereof.

In some embodiments, the method described herein includes as the first pharmaceutical composition a composition that comprises between about 0.05% w/v and about 2.0% w/v, between about 0.5% w/v and about 1.5% w/v, about 0.75% w/v, about 0.9% w/v, about 1.0% w/v, about 1.1% w/v, about 1.25% w/v, of an antioxidant or a combination of antioxidants.

In some embodiments, the method described herein includes as the first pharmaceutical composition a composition that comprises between about 5% w/v and about 30% w/v, between about 10% w/v and 20% w/v, between about 20% w/v to about 30% w/v, between about 12.5% w/v and 17.5% w/v, about 15% w/v, about 20% w/v, about 25% w/v, about 24% w/v or about 15.2% w/v base.

In some embodiments, the method described herein includes administration of the first pharmaceutical composition via one or two sites.

In some embodiments, the method described herein includes administration of the first pharmaceutical composition at a volume of between about 1 ml to about 30 ml per site per day, between about 2 ml to about 20 ml per site per day, between about 3 ml to about 10 ml per site per day, between about 5 ml to about 7 ml per site per day, about 9 ml per site per day, about 10 ml per site per day, about 11 ml per site per day, about 12 ml per site per day, or about 6 ml per site per day.

Also disclosed herein is a first pharmaceutical composition comprising: levodopa, a levodopa salt, a levodopa prodrug, or any combination thereof; and a dopa decarboxylase inhibitor (DDCI), a DDCI salt, a DDCI prodrug, or any combination thereof; and, a second pharmaceutical composition comprising: levodopa, a levodopa salt, a levodopa prodrug, a dopa decarboxylase inhibitor (DDCI), a DDCI salt, a DDCI prodrug; or any combination thereof, for use as a combination in the treatment of a neurological or movement disorder, wherein the first pharmaceutical composition is formulated as a parenteral composition and the second pharmaceutical composition is formulated as an oral composition.

Also disclosed herein is a kit comprising: a first pharmaceutical composition in parenteral form comprising:

levodopa, a levodopa salt, a levodopa prodrug, or any combination thereof; and a dopa decarboxylase inhibitor (DDCI), a DDCI salt, a DDCI prodrug, or any combination thereof; a second pharmaceutical composition in oral form comprising: levodopa, a levodopa salt, a levodopa prodrug, a dopa decarboxylase inhibitor (DDCI), a DDCI salt, a DDCI prodrug; or any combination thereof; and instructions for the concomitant administration of the first pharmaceutical composition and the second pharmaceutical composition for the treatment of a neurological or movement disorder.

Disclosed herein, in other embodiments, is a method for treatment of a neurological or movement disorder in a patient in need thereof, said method comprising: subcutaneously administering to the patient, over a subcutaneous infusion time course of about 7 to about 10 hours or more (e.g., a time course of about 8 hours), a first pharmaceutically acceptable liquid composition comprising levodopa, a levodopa salt, a levodopa prodrug, or any combination thereof, and carbidopa, a carbidopa salt, a carbidopa prodrug, or any combination thereof, in an amount to deliver about 100 to 800 mg (e.g., 200 mg) of levodopa, the levodopa salt, the levodopa prodrug, or the combination thereof, and about 12 to about 50 mg of carbidopa, the carbidopa salt, the carbidopa prodrug, or the combination thereof, to the patient; and orally administering to the patient, before or during the subcutaneous infusion time course, an immediate release tablet or capsule comprising levodopa and carbidopa. Contemplated immediate release tablets may include for example 50 mg, 75 mg, 100 mg, 125 mg or 150 mg levodopa and/or may include 2.5 mg, 18.57 mg, 25 mg, 31.25 mg, 37.5 mg or 50 mg carbidopa. In some embodiments, the method described herein includes an initial and/or concurrent oral administration of the immediate release tablet or capsule with the start of the infusion time course, for example, oral administration of the immediate release tablet or capsule may occur at substantially the same time the infusion administration begins, and/or about 1, 2, 3, 4, or 5 hours after the start of the infusion time course (e.g., at about 0 hours or about 4 hours after the start of the infusion time course), and/or about 4 hours after the start of the infusion time course, and/or about 4 hours and about 8 hours after the start of the infusion time course, and/or about 1, 2, 3, 4, or 5 hours before the start of the infusion time course (e.g., at about 0 hours or about 4 hours before the start of the infusion time course).

In some embodiments, a method described herein includes the immediate release tablet or capsule that comprises 100 mg levodopa and 25 mg carbidopa.

Methods described herein may include subcutaneous administration of the first pharmaceutically acceptable liquid composition that comprises levodopa and carbidopa in an amount to deliver about 140 to 170 mg of levodopa, a levodopa salt, a levodopa prodrug, or any combination thereof, and about 16 to about 24 mg of carbidopa, a carbidopa salt, a carbidopa prodrug, or any combination thereof, to the patient. Contemplated first pharmaceutically acceptable liquid composition may include a liquid composition that comprises about 6% by weight levodopa, about 0.75% by weight carbidopa, and about 10% to about 20% by weight arginine.

In some embodiments, methods described herein may include subcutaneous administration of the first pharmaceutically acceptable liquid composition that comprises a levodopa prodrug and carbidopa, a carbidopa salt, a carbidopa prodrug, or any combination thereof in an amount to deliver about 550 to 650 mg of levodopa prodrug and about 24 to about 28 mg of carbidopa, carbidopa salt or carbidopa prodrug, to the patient. A contemplated first pharmaceutically acceptable liquid composition comprises about 30% by weight of the levodopa prodrug, about 1.3% by weight carbidopa, and about 20% to about 30% by weight arginine.

For example, a method described herein may include the concomitant subcutaneous administration of the first composition and the oral administration of the tablet or capsule, wherein the patient's levodopa area under the curve (AUC) from time 0 to the end of the infusion time is higher as compared to the combination of a patient's levodopa AUC from time 0 to the end of the infusion time of a patient who is subcutaneously administered the first composition alone and a patient's levodopa AUC when a tablet or capsule is administered alone, wherein the amount of levodopa administered concomitantly subcutaneously and orally is about the same as the combined amount of the levodopa subcutaneously alone and orally administered alone.

Also disclosed herein is a method for treatment of a neurological or movement disorder in a patient in need thereof, said method comprising: subcutaneously administering to the patient, over a subcutaneous infusion time course of about 7 to about 10 hours or more, a first pharmaceutically acceptable liquid composition comprising about 6% by weight levodopa, a levodopa salt, a levodopa prodrug, or any combination thereof, and about 0.75% by weight carbidopa, a carbidopa salt, a carbidopa prodrug, or any combination thereof, to the patient; and orally administering to the patient, before or during the subcutaneous infusion time course, an immediate release tablet or capsule comprising 50 mg, 75 mg, 100 mg, 125 mg, 150 mg, 200 mg, or 250 mg levodopa, and wherein the immediate release tablet or capsule optionally further comprises carbidopa.

Also disclosed herein is a method for treatment of a neurological or movement disorder in a patient in need thereof, said method comprising: subcutaneously administering to the patient, over a subcutaneous infusion time course of about 24 hours or more, a first pharmaceutically acceptable liquid composition comprising levodopa, a levodopa salt, a levodopa prodrug, or any combination thereof, and carbidopa, a carbidopa salt, a carbidopa prodrug, or any combination thereof, in an amount to deliver about 720 mg of levodopa, the levodopa salt, the levodopa prodrug, or the combination thereof, and about 90 mg of carbidopa, the carbidopa salt, the carbidopa prodrug, or the combination thereof, to the patient over the course of about 24 hours; and orally administering to the patient, before or during the subcutaneous infusion time course, a tablet or capsule, e.g., an immediate release or modified release, such as an extended release, tablet or capsule, comprising levodopa and carbidopa.

In some embodiments, the method disclosed herein includes administration of the subcutaneous infusion over the course of about 18 hours at a high activity rate and over the course of about 6 hours at a low activity rate, wherein about 691.2 mg levodopa, a levodopa salt, a levodopa prodrug, or any combination thereof, and about 86.4 mg carbidopa, a carbidopa salt, a carbidopa prodrug, or any combination thereof, is administered over the course of the high activity 18 hours and about 28.8 mg levodopa, a levodopa salt, a levodopa prodrug, or any combination thereof, and 3.6 mg carbidopa, a carbidopa salt, a carbidopa prodrug, or any combination thereof, is administered over the course of the low activity 6 hours.

According to some embodiments, the tablet or capsule is orally administered substantially concurrently with the start of the infusion time course. The tablet or capsule may be administered during the infusion at predefined intervals, or when desired or required, based on feedback, e.g., for the patient, caregiver, physician, sensors, and the like. The intervals at which the tablet or capsule are administered may be substantially the same, or different from one another. According to some embodiments, a tablet or capsule is orally administered about 1, 2, 3, 4, 5, 6, 7, 8, 9, 10, 11 or 12 hours after the start of the infusion time course, wherein any number of tablets or capsules may be administered, as detailed herein. According to some embodiments, the tablet or capsule comprises 100 mg levodopa and 25 mg carbidopa.

According to some embodiments, the first pharmaceutically acceptable liquid composition, which is administered according to the method of the invention for 24 hours or more, comprises about 6% by weight levodopa, a levodopa salt, a levodopa prodrug, or any combination thereof, about 0.75% by weight carbidopa, a carbidopa salt, a carbidopa prodrug, or any combination thereof, and about 10% to about 20% by weight arginine.

According to some embodiments, the first pharmaceutically acceptable liquid composition, which is administered according to the method of the invention for 24 hours or more, comprises about 30% by weight of the levodopa prodrug, about 1.0% by weight carbidopa, a carbidopa salt, a carbidopa prodrug, or any combination thereof, and about 20% to about 30% by weight arginine.

According to some embodiments, the first pharmaceutically acceptable liquid composition, which is administered according to the method of the invention for 24 hours or more, comprises about 30% by weight of the levodopa prodrug, about 1.3% by weight carbidopa, a carbidopa salt, a carbidopa prodrug, or any combination thereof, and about 20% to about 30% by weight arginine.

According to some embodiments, whether the first pharmaceutically acceptable liquid composition is administered according to the method of the invention for 24 hours or more, concomitantly with the oral administration of a tablet or capsule, as detailed herein, the patient's levodopa area under the curve (AUC) from time 0 to the end of the infusion time is higher than that compared to the combination of a patient's levodopa AUC from time 0 to the end of the infusion time when a patient is subcutaneously administered the first composition alone together with a patient's levodopa AUC when a tablet or capsule is administered alone, and when the amount of levodopa administered concomitantly subcutaneously and orally is about the same as the combined amount of the levodopa subcutaneously alone and orally administered alone.

Embodiments of the invention are directed to a method for treatment of Parkinson's disease in a patient in need thereof, wherein the method comprises:
  subcutaneously administering to the patient, over a subcutaneous infusion time course of about 24 hours or more, a first pharmaceutically acceptable liquid composition comprising: levodopa, carbidopa, arginine, and an antioxidant, in an amount to deliver about 720 mg of levodopa and about 90 mg of carbidopa to the patient over the course of about 24 hours; and
  orally administering to the patient, before or during the subcutaneous infusion time course, at least one oral dosage form comprising levodopa.

Embodiments of the invention are directed to a method for treatment of Parkinson's disease in a patient in need thereof, wherein the method comprises:
  parenterally administering a first pharmaceutical composition comprising:
    a levodopa prodrug; and
    a dopa decarboxylase inhibitor (DDCI), a DDCI salt, a DDCI prodrug, or any combination thereof; and, concomitantly,
  orally administering a morning oral dose composition comprising:
    levodopa, a levodopa salt, or a levodopa prodrug;
    a dopa decarboxylase inhibitor (DDCI), a DDCI salt, a DDCI prodrug, or any combination thereof.

Embodiments of the invention are directed to a method for treatment of Parkinson's disease in a patient in need thereof, wherein the method comprises:
  subcutaneously administering to the patient, over a subcutaneous infusion time course of about 24 hours or more, a first pharmaceutically acceptable liquid composition comprising: levodopa, carbidopa, arginine, and an antioxidant, in an amount to deliver about 720 mg of levodopa and about 90 mg of carbidopa to the patient over the course of about 24 hours; and
  orally administering to the patient, before or during the subcutaneous infusion time course, at least one oral dosage form comprising levodopa.

Embodiments of the invention are directed to a method for treatment of Parkinson's disease in a patient in need thereof, wherein the method comprises:
  subcutaneously administering to the patient, over a subcutaneous infusion time course of about 24 hours or more, a first pharmaceutically acceptable liquid composition comprising: a levodopa prodrug, carbidopa, arginine, and an antioxidant, in an amount to deliver about 900 mg of the levodopa prodrug and about 30 mg of carbidopa to the patient over the course of about 24 hours; and
  orally administering to the patient, before or during the subcutaneous infusion time course, at least one oral dosage form comprising levodopa.

According to some embodiments, the oral dosage form includes one of: about 50 mg levodopa, about 75 mg levodopa, about 95 mg levodopa, about 100 mg levodopa, about 125 mg levodopa, about 145 mg levodopa, about 150 mg levodopa, about 195 mg levodopa, about 200 mg levodopa, about 245 mg levodopa, or about 250 mg levodopa.

Embodiments of the invention are directed to a method for treatment of Parkinson's disease in a patient in need thereof, wherein the method comprises:
  subcutaneously administering to the patient, over a subcutaneous infusion time course of about 24 hours or more, a first pharmaceutically acceptable liquid composition comprising: a levodopa prodrug, carbidopa, arginine, and an antioxidant, in an amount to deliver about 1800 mg of the levodopa prodrug and about 78 mg of carbidopa to the patient over the course of about 24 hours; and
  orally administering to the patient, before or during the subcutaneous infusion time course, at least one oral dosage form comprising levodopa.

Embodiments of the invention are directed to a method for treatment of Parkinson's disease in a patient in need thereof, wherein the method comprises:
  subcutaneously administering to the patient, over a subcutaneous infusion time course of about 24 hours or more, a first pharmaceutically acceptable liquid composition comprising: a levodopa prodrug, carbidopa, arginine, and an antioxidant, in an amount to deliver about 1800 mg of the levodopa prodrug and about 60 mg of carbidopa to the patient over the course of about 24 hours; and
orally administering to the patient, before or during the subcutaneous infusion time course, at least one oral dosage form comprising levodopa.

Embodiments of the invention are directed to a method for treatment of Parkinson's disease in a patient in need thereof, wherein the method comprises:
subcutaneously administering to the patient, over a subcutaneous infusion time course of about 24 hours or more, a first pharmaceutically acceptable liquid composition comprising: a levodopa prodrug, carbidopa, arginine, and an antioxidant, in an amount to deliver about 2700 mg of the levodopa prodrug and about 90 mg of carbidopa to the patient over the course of about 24 hours; and
orally administering to the patient, before or during the subcutaneous infusion time course, at least one oral dosage form comprising levodopa.

Embodiments of the invention are directed to a method for treatment of Parkinson's disease in a patient in need thereof, wherein the method comprises:
subcutaneously administering to the patient, over a subcutaneous infusion time course of about 24 hours or more, a first pharmaceutically acceptable liquid composition comprising: a levodopa prodrug, carbidopa, arginine, and an antioxidant, in an amount to deliver about 2700 mg of the levodopa prodrug and about 117 mg of carbidopa to the patient over the course of about 24 hours; and
orally administering to the patient, before or during the subcutaneous infusion time course, at least one oral dosage form comprising levodopa.

Embodiments of the invention are directed to a method for treatment of Parkinson's disease in a patient in need thereof, wherein the method comprises:
subcutaneously administering to the patient, over a subcutaneous infusion time course of about 24 hours or more, a first pharmaceutically acceptable liquid composition comprising: a levodopa prodrug, carbidopa, arginine, and an antioxidant, in an amount to deliver about 3500 mg of the levodopa prodrug and about 120 mg of carbidopa to the patient over the course of about 24 hours; and
orally administering to the patient, before or during the subcutaneous infusion time course, at least one oral dosage form comprising levodopa.

Embodiments of the invention are directed to a method for treatment of Parkinson's disease in a patient in need thereof, wherein the method comprises:
subcutaneously administering to the patient, over a subcutaneous infusion time course of about 24 hours or more, a first pharmaceutically acceptable liquid composition comprising: a levodopa prodrug, carbidopa, arginine, and an antioxidant, in an amount to deliver about 3000 mg of the levodopa prodrug and about 130 mg of carbidopa to the patient over the course of about 24 hours; and
orally administering to the patient, before or during the subcutaneous infusion time course, at least one oral dosage form comprising levodopa.

Embodiments of the invention are directed to a method for treatment of Parkinson's disease in a patient in need thereof, wherein the method comprises:
subcutaneously administering to the patient, over a subcutaneous infusion time course of about 24 hours or more, a first pharmaceutically acceptable liquid composition comprising: a levodopa prodrug, carbidopa, arginine, and an antioxidant, in an amount to deliver about 4200 mg of the levodopa prodrug and about 150 mg of carbidopa to the patient over the course of about 24 hours; and
orally administering to the patient, before or during the subcutaneous infusion time course, at least one oral dosage form comprising levodopa.

Embodiments of the invention are directed to a method for treatment of Parkinson's disease in a patient in need thereof, wherein the method comprises:
subcutaneously administering to the patient, over a subcutaneous infusion time course of about 24 hours or more, a first pharmaceutically acceptable liquid composition comprising: a levodopa prodrug, carbidopa, arginine, and an antioxidant, in an amount to deliver about 3300 mg of the levodopa prodrug and about 143 mg of carbidopa to the patient over the course of about 24 hours; and
orally administering to the patient, before or during the subcutaneous infusion time course, at least one oral dosage form comprising levodopa.

Embodiments of the invention are directed to a method for treatment of Parkinson's disease in a patient in need thereof, wherein the method comprises:
subcutaneously administering to the patient, over a subcutaneous infusion time course of about 24 hours or more, a first pharmaceutically acceptable liquid composition comprising: a levodopa prodrug, carbidopa, arginine, and an antioxidant, in an amount to deliver about 3600 mg of the levodopa prodrug and about 156 mg of carbidopa to the patient over the course of about 24 hours; and
orally administering to the patient, before or during the subcutaneous infusion time course, at least one oral dosage form comprising levodopa.

According to some embodiments, the treatment includes the treatment of motor fluctuations.

According to further embodiments, the oral dosage form is a morning oral dose.

Further embodiments, of the invention are directed to a method for treatment of Parkinson's disease, in a patient in need thereof, wherein the method comprises:
subcutaneously administering to the patient, over a subcutaneous infusion time course of about 24 hours or more, a first pharmaceutical composition comprising a levodopa moiety and a carbidopa moiety; and, concomitantly,
orally administering to the patient, before or during the subcutaneous infusion time course, at least one oral dosage form comprising levodopa.

According to some embodiments, the first pharmaceutical composition comprises the levodopa moiety and the carbidopa moiety in a ratio of about 8:1 w/w.

According to some embodiments, the first pharmaceutical composition comprises the levodopa moiety and the carbidopa moiety in a ratio of about 30:1 w/w.

According to some embodiments, the first pharmaceutical composition comprises up to about 720 mg levodopa and up to about 90 mg carbidopa, administered over the course of about 24 hours, wherein the levodopa and carbidopa are in a ratio of about 8:1 w/w. According to some embodiments, the first pharmaceutical composition comprises about 370 mg to about 720 mg levodopa and about 46 mg to about 90 mg carbidopa, administered over the course of about 24 hours, wherein the levodopa and carbidopa are in a ratio of about 8:1 w/w.

According to some embodiments, the first pharmaceutical composition comprises up to about 4200 mg levodopa moiety and up to about 150 mg carbidopa moiety, wherein the levodopa and carbidopa moieties are in a ratio of about 30:1 w/w. According to some embodiments, the oral dosage form is a morning oral dose.

Additional embodiments of the invention are directed to a method for treatment of Parkinson's disease in a patient in need thereof, wherein the method comprises:

subcutaneously administering to the patient, over a subcutaneous infusion time course of about 24 hours or more, a first pharmaceutically acceptable liquid composition comprising: levodopa and carbidopa, in an amount to deliver levodopa and carbidopa in a ratio of about 8:1 w/w to the patient over the course of about 24 hours; and orally administering to the patient, before or during the subcutaneous infusion time course, at least one oral dosage form comprising levodopa.

Embodiments of the invention are directed to a method for treatment of Parkinson's disease in a patient in need thereof, wherein the method comprises:

subcutaneously administering to the patient, over a subcutaneous infusion time course of about 24 hours or more, a first pharmaceutically acceptable liquid composition comprising: a levodopa prodrug and carbidopa, in an amount to deliver a levodopa prodrug and carbidopa in a ratio of about 30:1 w/w to about 8:1 w/w to the patient to the patient over the course of about 24 hours; and orally administering to the patient, before or during the subcutaneous infusion time course, at least one oral dosage form comprising levodopa.

According to some embodiments, the pharmaceutically acceptable liquid composition comprising levodopa and carbidopa, in an amount to deliver about 370 to about 720 mg of levodopa and about 46 to about 90 mg of carbidopa to the patient over the course of about 24 hours.

Some embodiments of the invention are directed to a method for treatment of Parkinson's disease in a patient in need thereof, wherein the method comprises:

subcutaneously administering to the patient, over a subcutaneous infusion time course of about 24 hours or more, a first pharmaceutically acceptable liquid composition comprising: levodopa and carbidopa, in an amount to deliver about 370 to about 720 mg of levodopa and about 46 to about 90 mg of carbidopa to the patient over the course of about 24 hours; and orally administering to the patient, before or during the subcutaneous infusion time course, at least one oral dosage form comprising levodopa.

According to some embodiments, the first pharmaceutically acceptable liquid composition comprises levodopa and carbidopa in a ratio of about 8:1 w/w.

Embodiments of the invention are directed to a method for treatment of Parkinson's disease in a patient in need thereof, wherein the method comprises:

subcutaneously administering to the patient, over a subcutaneous infusion time course of about 24 hours or more, a first pharmaceutically acceptable liquid composition comprising: a levodopa moiety and a carbidopa moiety, in an amount to deliver the levodopa moiety and the carbidopa moiety in a ratio of about 30:1 w/w to the patient over the course of about 24 hours; and orally administering to the patient, before or during the subcutaneous infusion time course, at least one oral dosage form comprising levodopa.

Embodiments of the invention are directed to a method for treatment of Parkinson's disease, in a patient in need thereof, wherein the method comprises:

subcutaneously administering to the patient, over a subcutaneous infusion time course of about 24 hours or more, a first pharmaceutical composition comprising: a levodopa prodrug and a carbidopa prodrug, and, concomitantly, orally administering to the patient, before or during the subcutaneous infusion time course, at least one oral dosage form comprising levodopa, wherein up to about 4260 mg of levodopa is administered to the patient per day.

According to some embodiments, the methods provided herein may further comprise administering to the patient one or more loading dose. According to some embodiments, the loading dose is administered by subcutaneous infusion. According to some embodiments, the loading dose is administered orally.

According to some embodiments, the methods provided herein may further comprise administering to the patient one or more extra dose. According to some embodiments, the extra dose is administered by subcutaneous infusion. According to some embodiments, the extra dose is administered orally.

Also disclosed herein is a method for treatment of Parkinson's disease in a patient in need thereof, said method comprising:

subcutaneously administering to the patient, over a subcutaneous infusion time course of about 24 hours or more, a first pharmaceutically acceptable liquid composition comprising: a levodopa prodrug, and carbidopa or a carbidopa prodrug, where the levodopa prodrug is present in an amount to deliver up to about 4260 mg of levodopa to the patient over the course of about 24 hours; and orally administering to the patient, before or during the subcutaneous infusion time course, at least one oral dosage form, each comprising levodopa.

According to some embodiments, the carbidopa or carbidopa prodrug is administered in an amount to deliver up to about 220-227 mg (e.g., up to about 220 mg, up to about 221 mg, up to about 222 mg, up to about 223 mg, up to about 224 mg, up to about 225 mg, up to about 226 mg, or up to about 227 mg) of carbidopa to the patient over the course of about 24 hours. According to some embodiments, the first pharmaceutically acceptable liquid composition comprises a carbidopa prodrug and the levodopa prodrug to carbidopa prodrug is present in the composition in a ratio of about 20:1 w/w.

According to some embodiments, the first pharmaceutically acceptable liquid composition is administered to the patient at a rate of about 0.15 ml/site/hr to about 1.04 ml/site/hr.

According to some embodiments, the method further comprises administering an extra dose of a levodopa prodrug, wherein the levodopa prodrug is present in an amount to deliver from about 5 mg levodopa to about 75 mg levodopa to the patient. According to some embodiments, the extra dose of levodopa prodrug is present in an amount to deliver about 17 mg, about 25.5 mg, about 34 mg, about 42.5 mg, or about 51 mg of levodopa to the patient. According to some embodiments, 1, 2, 3, 4 or 5 extra doses may be administered to the patient over the course of 24 hours. According to some embodiments, no more than 1 extra dose may be administered over the course of 1 hour. According to some embodiments, the amount of levodopa administered to the patient, over the course of 24 hours, by extra dose(s) is between about 17 mg and about 255 mg or between about 17 and about 300 mg. It is noted that if several extra doses are administered per 24 hours, they can either be identical or different from one another in volume/amount of levodopa administered.

According to some embodiments, the method further comprises administering a loading dose of a levodopa prodrug, wherein the levodopa prodrug is present in an amount to deliver between about 50 mg to about 500 mg of levodopa to the patient in each loading dose. According to some embodiments, the method further comprises administering a loading dose of a levodopa prodrug, wherein the levodopa prodrug is present in an amount to deliver about 50 mg, about 100 mg, about 150 mg, about 200 mg, about 250 mg, about 300 mg, about 350 mg of levodopa to the patient, in each loading dose. According to some embodiments, the loading dose is administered subcutaneously. According to some embodiments, the loading dose is administered orally. According to some embodiments, the loading dose is administered orally in an amount to provide about 50 mg, about 100 mg, about 150 mg, about 200 mg, about 250 mg, about 300 mg, about 350 mg of levodopa to the patient, in each loading dose.

According to some embodiments, the oral dosage form includes one of: about 50 mg levodopa, about 75 mg levodopa, about 95 mg levodopa, about 100 mg levodopa, about 125 mg levodopa, about 145 mg levodopa, about 150 mg levodopa, about 195 mg levodopa, about 200 mg levodopa, about 245 mg levodopa, or about 250 mg levodopa. According to some embodiments, the oral dosage form further comprises a COMT inhibitor. According to some embodiments, the oral dosage form is a morning oral dose. According to some embodiments, the oral dosage form is a loading dose.

According to some embodiments, the treatment includes the treatment of motor fluctuations. According to some embodiments, the treatment includes the treatment of advanced Parkinson's disease. According to some embodiments, the treatment includes the treatment of hyperkinesia dyskinesia.

Also disclosed herein is a method for treatment of Parkinson's disease in a patient in need thereof, said method comprising:

subcutaneously administering to the patient, over a subcutaneous infusion time course of about 24 hours or more, a first pharmaceutically acceptable liquid composition comprising: a levodopa prodrug, and a carbidopa or a carbidopa prodrug, at a volume of between about 1 ml to about 30 ml per site per day to the patient over the course of about 24 hours; and orally administering to the patient, before or during the subcutaneous infusion time course, at least one oral dosage form each comprising levodopa. According to some embodiments, the volume of the first pharmaceutically acceptable liquid composition administered subcutaneously in one site, over the course of 24 hours is between about 3.6 ml and about 25 ml. According to some embodiments, the volume of the first pharmaceutically acceptable liquid composition administered subcutaneously is determined according to the amount of levodopa required for the particular patient. This volume may change according to the patient's symptoms. The volume may be changed by the patient, a caregiver, a physician, nurse, technician, or any other person with knowledge of operating the delivery system.

According to some embodiments, the levodopa prodrug is present in an amount to deliver up to about 4260 mg of levodopa to the patient. According to some embodiments, the carbidopa or carbidopa prodrug is present in an amount to deliver up to about 220 mg-227 mg of carbidopa to the patient. According to some embodiments, the first pharmaceutically acceptable liquid composition comprises a carbidopa prodrug and has the levodopa prodrug to carbidopa prodrug in a ratio of about 20:1 w/w.

According to some embodiments, the first pharmaceutically acceptable liquid composition is administered at a rate of about 0.15 ml/site/hr to about 1.04 ml/site/hr.

According to some embodiments, the method further comprises administering a bolus dose, such as a loading dose or an extra dose, of a levodopa prodrug, wherein the levodopa is present in an amount to deliver from about 5 mg levodopa to about 500 mg levodopa to the patient. According to some embodiments, the extra dose of levodopa prodrug is present in an amount to deliver about 17 mg, 25.5. mg, 34 mg, 42.5 mg, or 51 mg of levodopa to the patient. According to some embodiments, the loading dose of levodopa prodrug is present in an amount to deliver about 50 mg, 100 mg, 150 mg, 200 mg, 250 mg, 300 mg, 350 mg, 400 mg, 450 mg, or 500 mg of levodopa to the patient.

According to some embodiments, the oral dosage form includes one of: about 50 mg levodopa, about 75 mg levodopa, about 95 mg levodopa, about 100 mg levodopa, about 125 mg levodopa, about 145 mg levodopa, about 150 mg levodopa, about 195 mg levodopa, about 200 mg levodopa, about 245 mg levodopa, or about 250 mg levodopa. According to some embodiments, the oral dosage form further comprises a COMT inhibitor.

According to some embodiments, the treatment includes the treatment of motor fluctuations.

DETAILED DESCRIPTION OF THE INVENTION

Figure 1:
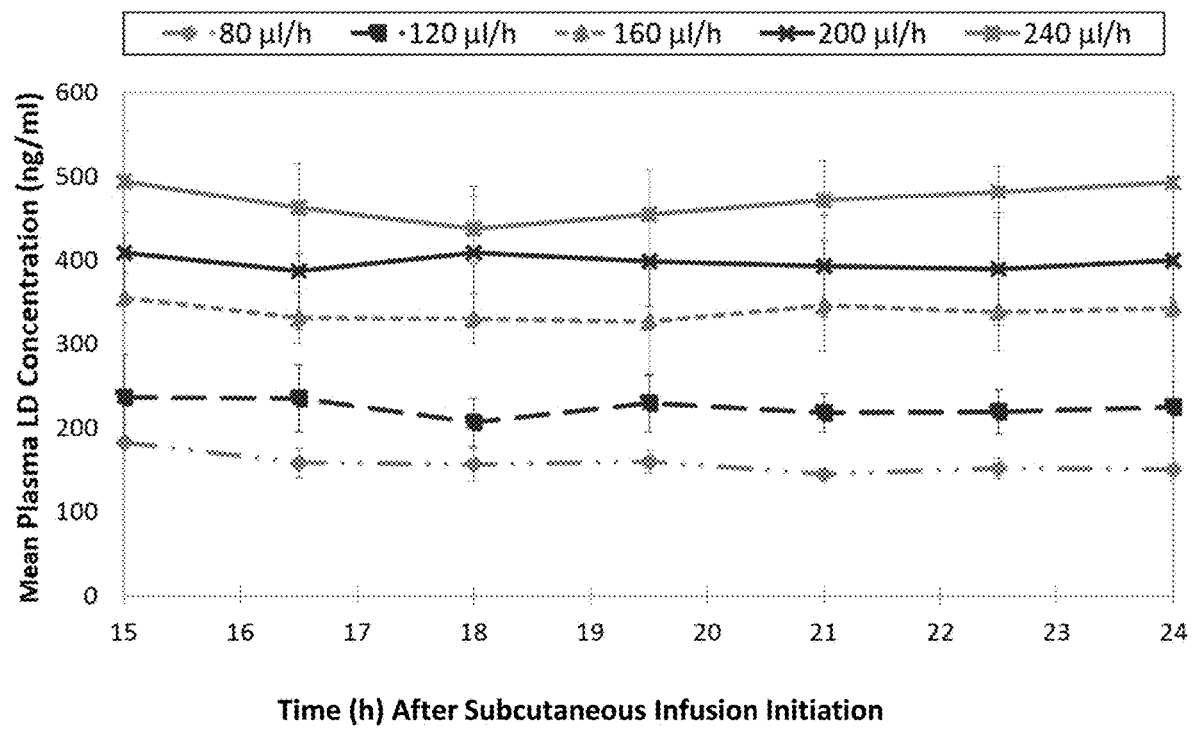
FIG. 1 provides a graph showing the mean plasma levodopa concentration of five tested groups vs the time in hours after subcutaneous infusion initiation.

The features and other details of the disclosure will now be more particularly described. Certain terms employed in the specification, examples, and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The terms "treat," "treatment," "treating," and the like are used herein to generally refer to obtaining a desired pharmacological and/or physiological effect. The effect may be therapeutic in terms of partially or completely curing a disease and/or adverse effect attributed to the disease. The term "treatment" as used herein covers any treatment of a disease in a mammal, particularly a human, and includes: (a) inhibiting the disease, i.e., preventing the disease from increasing in severity or scope; (b) relieving the disease, i.e., causing partial or complete amelioration of the disease; or (c) preventing relapse of the disease, i.e., preventing the disease from returning to an active state following previous successful treatment of symptoms of the disease or treatment of the disease.

"Preventing" includes delaying the onset of clinical symptoms, complications, or biochemical indicia of the state, disorder, disease, or condition developing in a subject that may be afflicted with or predisposed to the state, disorder, disease, or condition but does not yet experience or display clinical or subclinical symptoms of the state, disorder, disease, or condition. "Preventing" includes prophylactically treating a state, disorder, disease, or condition in, or developing in, a subject, including prophylactically treating clinical symptoms, complications, or biochemical indicia of the state, disorder, disease, or condition in or developing in a subject.

The term "pharmaceutically acceptable carrier" or "pharmaceutically acceptable excipient" as used herein interchangeably refer to any and all solvents, dispersion media, coatings, isotonic and absorption delaying agents, and the like, that are compatible with pharmaceutical administration.

The terms "pharmaceutical composition" and "pharmaceutical formulation" as used herein refer to a composition or formulation comprising at least one biologically active compound, for example, levodopa or carbidopa, or a pharmaceutically acceptable salt thereof or a prodrug thereof, formulated together with one or more pharmaceutically acceptable excipients.

The term "pharmaceutically acceptable salt(s)" as used herein refers to salts of acidic or basic groups that may be formed with the conjugates used in the compositions disclosed herein.

"Individual," "patient," or "subject" are used interchangeably and include any animal, including mammals, mice, rats, other rodents, rabbits, dogs, cats, swine, cattle, sheep, horses, or non-human primates, and humans. In some embodiments, the mammal treated in the methods of the invention is a human suffering from neurodegenerative condition, such as Parkinson's disease.

The term "about", as used herein, unless specifically mentioned otherwise, or unless a person skilled in the art would have understood otherwise, is considered to cover a range of ±10% of the listed value(s). It is further noted that any value provided may also be considered to cover a range of ±10% of that value, even without the use of the term "about". This includes the values in the examples section, which may vary according to the utensils and machinery used, the purity of the compounds, etc.

The term "up to" as used herein, unless specifically mentioned otherwise, or unless would have been understood otherwise by a person skilled in the art, when appearing as part of a range, is defined such that the range does not include "none", "nothing", "0". That is, if a component is an amount of up to a certain amount, e.g., 720 mg, 0 mg is not considered to be part of the range. Thus, if a composition comprises, e.g., up to 360 mg, up to 370 mg, up to 720 mg, of, e.g., levodopa, the composition must include more than 0 levodopa. Similarly, if a composition comprises, e.g., up to 45 mg, up to 46 mg, up to 90 mg, of, e.g., carbidopa, the composition must comprise more than 0 carbidopa.

The term "levodopa moiety", as used herein, unless specifically mentioned otherwise, or unless would have been understood otherwise by a person skilled in the art, includes any moiety including levodopa, including, e.g., levodopa itself, a levodopa prodrug, and a levodopa salt. Similarly, the term "carbidopa moiety", as used herein, unless specifically mentioned otherwise, or unless would have been understood otherwise by a person skilled in the art, includes any moiety including carbidopa, including, e.g., carbidopa itself, a carbidopa prodrug, a carbidopa salt.

The term "liquid" as used herein, unless specifically mentioned otherwise, or unless a person skilled in the art would have understood otherwise, refers to any type of fluid, including gels, aqueous and non-aqueous compositions, and the like.

The term "concomitant" as used herein, unless specifically mentioned otherwise, or unless a person skilled in the art would have understood otherwise, refers to any type of combined administration of two or more active ingredients, in the same composition, as well as the administration of those active ingredients at the same time, in separate compositions, as well as administering the two or more active ingredients sequentially, consecutively, on the same day, with a predefined period of time separating the administration of the active ingredients from one another, and the like. The term "concomitant" may further be used herein to refer to any type of combined administration of two separate pharmaceutical compositions, wherein each composition may be administered in a different administration route, at different time intervals, doses, etc. For examples, as detailed herein, one composition may be administered parenterally, e.g., subcutaneously, substantially continuously, while a second composition, administered concomitantly with the first, by oral administration, in a non-continuous manner. Further, the concomitant administration of two or more separate compositions may be dependent or independent from one another.

The terms "continuously" and "substantially continuously" as used herein, unless specifically mentioned otherwise, or unless a person skilled in the art would have understood otherwise, refer to a period of time during which a composition is administered over the entire period of time, with intermissions of less than about 24 hours, about 12 hours, about five hours, about three hours, about one hour, about 30 minutes, about 15 minutes, about five minutes or about one minute. The period of time during which a composition is administered may be at least about six hours, about eight hours, about 12 hours, about 15 hours, about 18 hours, about 21 hours, about 24 hours, three days, seven days, two weeks, a month, three months, six months, a year, two years, three years, five years, ten years, etc.

The term "physiologically acceptable pH value" and the like, as used herein, unless specifically mentioned otherwise, or unless a person skilled in the art would have understood otherwise, refers to pH values in the range of between about 4.5 to about 10. It is further noted that when pH values are provided, including in the examples, the values may be in the range of about ±0.1 and/or ±10% of the listed value(s), such that if the measured pH is 8.1, the same formulation may be prepared to provide a pH of about 8.0 or 8.2. Such differences may be due to temperature changes, various measuring devices, etc.

A neurological disorder is a disorder of the body's nervous system, and the term "movement disorder" as used herein refers to a nervous system condition that causes abnormal voluntary or involuntary movements, or slow, reduced movements. According to some embodiments, the neurological or movement disorder is Parkinson's disease; secondary parkinsonism, such as drug-induced secondary parkinsonism, neuroleptic induced parkinsonism, postencephalitic parkinsonism, and vascular parkinsonism; motor fluctuations; neurodegenerative disorders; dyskinesia; reduced dopamine levels in the brain; levodopa induced dyskinesia; rapid eye movement sleep behavior disorder (RBD); dystonia; morning akinesia; tremor symptoms, such as essential tremor and drug-induced tremor; myoclonus; chorea, such as drug induced chorea; tics, such as drug induced tics and organic tics; drug induced movement disorder; drug induced akathisia; restless legs syndrome (RLS); stiff-man syndrome; benign shuddering attacks; malignant neuroleptic syndrome; Huntington's disease; Shy-Drager syndrome; brain injury induced conditions, such as carbon monoxide or manganese intoxication; or any combination thereof. According to some embodiments, the method is directed to treating Parkinson's disease and/or motor fluctuations, including motor fluctuations stemming from Parkinson's disease, motor fluctuations in patients with Parkinson disease, and the like.

The term "dopa decarboxylase inhibitor" as used herein refers to an agent capable of inhibiting the peripheral metabolism of levodopa to dopamine by aromatic L-amino acid decarboxylase, such as carbidopa, benserazide, methyldopa, 3',4',5,7-tetrahydroxy-8-methoxyisoflavone, alpha-difluoromethyl-dopa, or any combination thereof.

The terms "morning dose" and "morning oral dose" as used herein, unless specifically mentioned otherwise, or unless would have been understood otherwise by a person skilled in the art, are interchangeable and refer to an oral dosage form comprising levodopa, which is particularly administered in the morning hours, e.g., within 1 minute, 5 minutes, 10 minutes, 15 minutes, 20 minutes, 30 minutes, 45 minutes, 1 hour, 1.5 hours, 2 hours of the patient's waking time. according to some embodiments, the morning dose refers to an oral dosage form comprising levodopa, which is administered within 1 minute, 5 minutes, 10 minutes, 15 minutes, 20 minutes, or 30 minutes of the patient's waking hours.

The term "loading dose" refers to a dose of a pharmaceutical composition comprising levodopa or a levodopa moiety, e.g., a levodopa prodrug, (e.g., a bolus dose of levodopa, a levodopa moiety such as a levodopa prodrug), that may be administered in order to quickly achieve symptomatic control or a desired therapeutic state when the patient is, for example, in an "off" state (such as when the administration of the therapeutic drug has been discontinued (off) for an extended period of time and/or the patient exhibits undesired symptoms of Parkinson's such as poor motor control, poor mobility, tremor and/or stiffness). A loading dose may be administered for example:
  prior to initiation of the continuous infusion;
  between two consecutive continuous infusion session, which are separated by a period of time, e.g., 2, 3, 4, 5 or more, hours, during which the continuous infusion was not administered,
  after a period of time during which the continuous infusion dose was relatively low, e.g., in the morning, after the night hours.

It is noted that the loading dose may be administered as an infusion bolus, or by way of oral administration of a pharmaceutical composition comprising levodopa or levodopa equivalents, in any known oral form.

The term "extra dose" refers to a dose of a pharmaceutical composition comprising levodopa, a levodopa moiety or e.g., a levodopa prodrug, (e.g., a bolus dose of levodopa, a levodopa moiety such as a levodopa prodrug), that may be administered in order to quickly achieve symptomatic control or a desired therapeutic state, as needed, for example, to manage acute "off" symptoms experienced during continuous infusion. It is noted that the extra dose may be administered as an infusion bolus, or by way of oral administration of a pharmaceutical composition comprising levodopa or levodopa equivalents, in any known oral form.

Any type of bolus dose, whether referred to herein as a loading dose, an extra dose, a bolus, or any other relevant term, may be administered 1, 2, 3, 4, 5, or more times per day or as prescribed by a physician, or as determined necessary by the patient, caregiver, or physician. The number and timing of the various bolus doses may change from time to time. The bolus doses may be administered by way of infusion, e.g., via a subcutaneous infusion pump, or by way of oral administration.

The loading dose, extra dose, or any other bolus dose may be administered subcutaneously in a volume of up to about 5 ml per dose. The loading dose, extra dose, or any other bolus dose may be administered subcutaneously at a volume of about 0.1 ml, about 0.15 ml, about 0.2 ml, about 0.25 ml, about 0.3 ml, about 0.4 ml, about 0.5 ml, about 0.6 ml, about 0.9 ml, about 1.2 ml, about 1.5 ml, about 1.8 ml, about 2.0 ml, about 2.5 ml, about 3.0 ml, about 3.5 ml, about 4.0 ml, about 4.5 ml, or about 5.0 ml per dose.

The loading dose, extra dose, or any other bolus dose may be administered subcutaneously, orally, or both subcutaneously and orally in an amount providing up to about 500 mg levodopa or levodopa equivalents per dose. The loading dose, extra dose, or any other bolus dose may be administered subcutaneously, orally, or both subcutaneously and orally, in an amount of about 5 mg, about 10 mg, about 15 mg, about 17 mg, about 20 mg, about 25.5 mg, about 30 mg, about 34 mg, about 40 mg, about 42.5 mg, about 45 mg, about 50 mg, about 51 mg, about 75 mg, about 100 mg, about 150 mg, about 200 mg, about 250 mg, about 300 mg, about 350 mg, about 400 mg, about 450 mg, or about 500 mg, per dose.

As known in the field, the levodopa equivalent amount is calculated in order to assess the levodopa dose. For example, the levodopa equivalent is calculated using a dose multiplication factor of 1 for immediate release levodopa, a dose multiplication factor of 0.75 for any of sustained release, controlled release, or prolonged release levodopa, a dose multiplication factor of 1.33 for COMT inhibitors, etc. In addition, various calculations may be relevant for various levodopa moieties, such as levodopa prodrugs. For instance, the bioavailability of the prodrug may be different than that of levodopa itself, and therefore, must be taken into account. The prodrug may not fully convert to levodopa, such that the theoretical amount of levodopa is lower than expected. This too must be taken into account in the calculations of the levodopa equivalents. The calculation of levodopa equivalents may aid in determining the daily dose, as well as the loading dose, extra dose, or any other bolus dose administered to the patient.

According to some embodiments, the morning oral dose includes one of: 25 mg levodopa, 50 mg levodopa, 75 mg levodopa, 95 mg levodopa, 100 mg levodopa, 125 mg levodopa, 145 mg levodopa, 150 mg levodopa, 195 mg levodopa, 200 mg levodopa, 245 mg levodopa, or 250 mg levodopa.

Embodiments of the invention are directed to a method for treatment of a neurological or movement disorder, such as Parkinson's disease, in a patient in need thereof, wherein the method comprises:
  parenterally administering a first pharmaceutical composition comprising:
    levodopa, a levodopa salt, a levodopa prodrug, or any combination thereof; and
    a dopa decarboxylase inhibitor (DDCI), a DDCI salt, a DDCI prodrug, or any combination thereof;

and, concomitantly,
orally administering a second pharmaceutical composition comprising:
levodopa, a levodopa salt, a levodopa prodrug;
a dopa decarboxylase inhibitor (DDCI), a DDCI salt, a DDCI prodrug; or any combination thereof.

According to some embodiments, the concomitant administration of the first pharmaceutical composition and the second pharmaceutical composition provides a synergistic effect, such that the levodopa blood levels obtained by the concomitant administration are higher than the expected additive effect when providing the first pharmaceutical composition and the second pharmaceutical composition non-concomitantly. According to some embodiments, the synergism between the first and second pharmaceutical compositions provides an elevation of between about 5% and about 50% in the levodopa blood levels, in comparison to the expected additive values. According to some embodiments, the synergism between the first and second pharmaceutical compositions provides an elevation of between about 10% and 40% in the levodopa blood levels, between about 15% and 35% in the levodopa blood levels, between about 20% and 40 in the levodopa blood levels, between about 25% and 35% in the levodopa blood levels, or about 20%, 25%, or 30% in the levodopa blood levels, in comparison to the expected additive values.

According to some embodiments, the first pharmaceutical composition comprises a levodopa moiety and a carbidopa moiety. According to some embodiments, at least one of the levodopa moiety and the carbidopa moiety in the first pharmaceutical composition is a levodopa or carbidopa prodrug. According to some embodiments, both the levodopa moiety and the carbidopa moiety in the first pharmaceutical composition are a levodopa prodrug and a carbidopa prodrug, respectively. According to some embodiments, the second pharmaceutical composition comprises levodopa and carbidopa. According to some embodiments, the second pharmaceutical composition comprises only levodopa as the active ingredient. According to some embodiments, the second pharmaceutical composition further comprises a catechol o-methyl transferase (COMT) inhibitor, such as entacapone or tolcapone.

According to some embodiments, the first pharmaceutical composition comprises levodopa and carbidopa. According to some embodiments, the second pharmaceutical composition comprises levodopa and carbidopa. According to some embodiments, the second pharmaceutical composition comprises only levodopa as the active ingredient. According to some embodiments, the second pharmaceutical composition further comprises a catechol o-methyl transferase (COMT) inhibitor, such as entacapone or tolcapone.

According to some embodiments, the first pharmaceutical composition and/or the second pharmaceutical composition comprise (1) levodopa, a levodopa salt, and/or a levodopa prodrug and/or (2) carbidopa, a carbidopa salt and/or a carbidopa prodrug. According to some embodiments the levodopa prodrug is any of the prodrugs disclosed in PCT/IL2020/050960 or PCT/IL2022/050269, which are incorporated herein, in their entirety, by reference. According to some embodiments, the levodopa prodrug and/or the carbidopa prodrug is any prodrug disclosed in PCT/JP2022/012484.

According to some embodiments, the levodopa prodrug comprises a levodopa amino acid conjugate (LDAA) of the general formula (I):

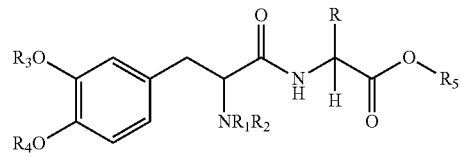

an enantiomer, diastereomer, racemate, ion, zwitterion, pharmaceutically acceptable salt thereof, or any combination thereof, wherein:
R is an amino acid side chain;
$R_1$ and $R_2$ each independently is selected from the group consisting of H, $(C_1\text{-}C_6)$alkyl, $(C_2\text{-}C_6)$alkenyl, $(C_2\text{-}C_6)$alkynyl, $C_3\text{-}C_6$cycloalkyl, phenyl, —O—C(=O)—R', —C(=O)—OR', —C(=O)—R', —C(=S)—R', —O—C(=O)—NR'R', —O—C(=S)—NR'R', or —O—C(=O)—R'';
$R_3$ and $R_4$ each independently is selected from the group consisting of H, $(C_1\text{-}C_3)$alkyl, $C_3\text{-}C_6$cycloalkyl, phenyl, or —P(=O)(OR')$_2$;
$R_5$ is selected from the group consisting of H, $(C_1\text{-}C_3)$alkyl, $C_3\text{-}C_6$cycloalkyl and phenyl;
R' is each independently selected from the group consisting of H, $(C_1\text{-}C_6)$alkyl, $(C_2\text{-}C_6)$alkenyl, $C_3\text{-}C_6$cycloalkyl, phenyl, and heteroaryl bonded to the nitrogen through a ring carbon; and
R'' is selected from the group consisting of a $(C_1\text{-}C_6)$alkyl, $(C_2\text{-}C_6)$alkenyl, and $(C_2\text{-}C_6)$alkynyl.

According to some embodiments, R is an amino acid side chain of any natural, synthetic, non-natural, or non-proteogenic amino acid, for example, the side chain of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, tryptophan, lanthionine, selenocysteine, pyrrolysine, ADDA amino acid ((2S,3S,4E,6E,8S,9S)-3-Amino-9-methoxy-2,6,8-trimethyl-10-phenyl-deca-4,6-dienoic acid), beta-alanine, 4-Aminobenzoic acid, gamma-aminobutyric acid, S-aminoethyl-L-cysteine, 2-aminoisobutyric acid, aminolevulinic acid, azetidine-2-carboxylic acid, canaline, canavanine, carboxyglutamic acid, chloroalanine, citrulline, cystine, dehydroalanine, diaminopimelic acid, dihydroxyphenylglycine, enduracididine, homocysteine, homoserine, 4-hydroxyphenylglycine, hydroxyproline, hypusine, beta-leucine, norleucine, norvaline, ornithine, penicillamine, plakohypaphorine, pyroglutamic acid, quisqualic acid, sarcosine, theanine, tranexamic acid, tricholomic acid, or any isomer thereof. In this respect it is noted that R may be either of the known isomers of lanthionine, wherein one is referred to herein as lanthionine-1 or lanthionine-peak 1, while the other is referred to herein as lanthionine-2 or lanthionine-peak 2. Further, the levodopa lanthionine conjugates may be referred to herein as LD-LA, LD-LA 1 (for the first isomer), LD-LA 2 (for the second isomer), LD-lanthionine 1 (for the first isomer), LD-lanthionine 2 (for the second isomer), and the like.

According to some embodiments, R is an amino acid side chain of arginine, tyrosine, lysine, aspartic acid, asparagine, tryptophan, glutamine, glutamic acid, glycine, or lanthionine. According to some embodiments, R is an amino acid side chain of arginine, tyrosine, lysine, lanthionine-2, tryptophan, glutamic acid or glycine. According to some embodiments, R is an amino acid side chain of arginine, tyrosine, lysine or lanthionine-2. According to some embodiments, R is an amino acid side chain of arginine, tyrosine or lysine. According to some embodiments, R is the amino acid side chain of lanthionine-2.

According to some embodiments, each one of $R_1$, $R_2$, $R_3$, $R_4$ and $R_5$ are H. According to some embodiments, R" has at least 10 carbon atoms. According to some embodiments, the pharmaceutical composition comprises a mixture of two or more LDAA compounds.

According to some embodiments, the levodopa prodrug comprises a levodopa amino acid conjugate (LDAA) of the general formula (II):

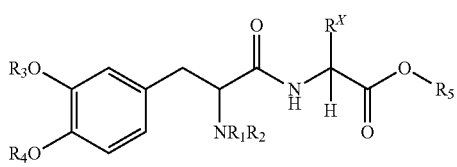

II an enantiomer, diastereomer, racemate, ion, zwitterion, pharmaceutically acceptable salt thereof, or any combination thereof, wherein
- $R^X$ is an amino acid side chain or an O-phosphorylated amino acid side chain thereof;
- R1 and R2 each independently is selected from the group consisting of H, (C1-C6)alkyl, (C2-C6)alkenyl, (C2-C6)alkynyl, C3-C6cycloalkyl, phenyl, —O—C(=O)—R', —C(=O)—OR', —C(=O)—R', —C(=S)—R', —O—C(=O)—NR'R', —O—C(=S)—NR'R', or —O—C(=O)—R";
- R3 and R4 each independently is selected from the group consisting of H, (C1-C3)alkyl, C3-C6cycloalkyl, phenyl, or —P(=O)(OR')2;
- R5 is selected from the group consisting of H, (C1-C3) alkyl, C3-C6cycloalkyl and phenyl;
- R' is each independently selected from the group consisting of H, (C1-C6)alkyl, (C2-C6)alkenyl, $C_3$-$C_6$cycloalkyl, phenyl, and heteroaryl bonded to the nitrogen through a ring carbon; and
- R" is selected from the group consisting of a (C1-C6) alkyl, (C2-C6)alkenyl, and (C2-C6)alkynyl.

According to some embodiments, the levodopa prodrug comprises a levodopa amino acid conjugate (LDAA) of the general formula (III):

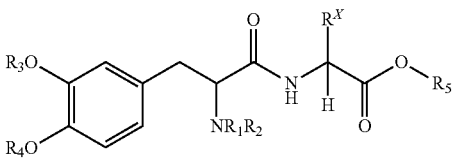

III an enantiomer, diastereomer, racemate, ion, zwitterion, pharmaceutically acceptable salt thereof, or any combination thereof, wherein
- $R^X$ is an amino acid side chain selected from the group consisting of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, tryptophan, ornithine, lanthionine and 3,4-dihydroxyphenylalanine side chain; or a O-phosphorylated amino acid side chain thereof;

- $R_1$ and $R_2$ each independently is selected from the group consisting of H, $(C_1$-$C_6)$alkyl, $(C_2$-$C_6)$alkenyl, $(C_2$-$C_6)$ alkynyl, $C_3$-$C_6$cycloalkyl, phenyl, —O—C(=O)—R', —C(=O)—OR', —C(=O)—R', —C(=S)—R', —O—C(=O)—NR'R', —O—C(=S)—NR'R', or —O—C(=O)—R";
- $R_3$ and $R_4$ each independently is selected from the group consisting of H, $(C_1$-$C_3)$alkyl, $C_3$-$C_6$cycloalkyl, phenyl, or —P(=O)(OR')$_2$;
- $R_5$ is selected from the group consisting of H, $(C_1$-$C_3)$ alkyl, $C_3$-$C_6$cycloalkyl and phenyl;
- R' is each independently selected from the group consisting of H, $(C_1$-$C_6)$alkyl, $(C_2$-$C_6)$alkenyl, $C_3$-$C_6$cycloalkyl, phenyl, and heteroaryl bonded to the nitrogen through a ring carbon; and
- R" is selected from the group consisting of a $(C_1$-$C_6)$alkyl, $(C_2$-$C_6)$alkenyl, and $(C_2$-$C_6)$alkynyl.

For example, in embodiments described herein, the amino acid side chain in $R^X$ can be:

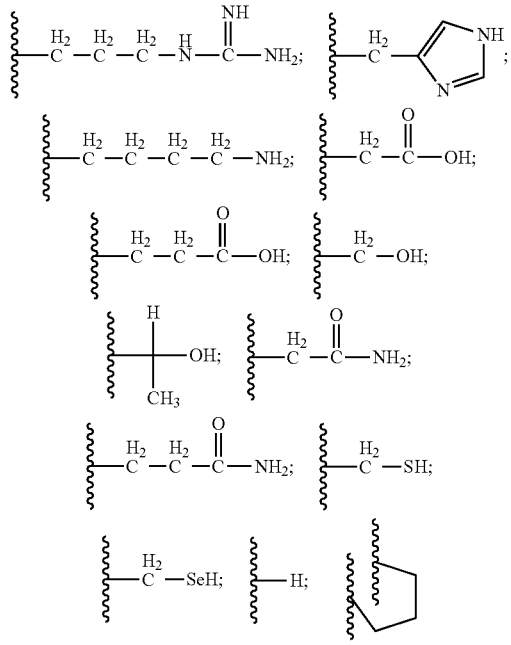

(wherein $R^X$ also forms a bond with N of the peptide bond of the compound);

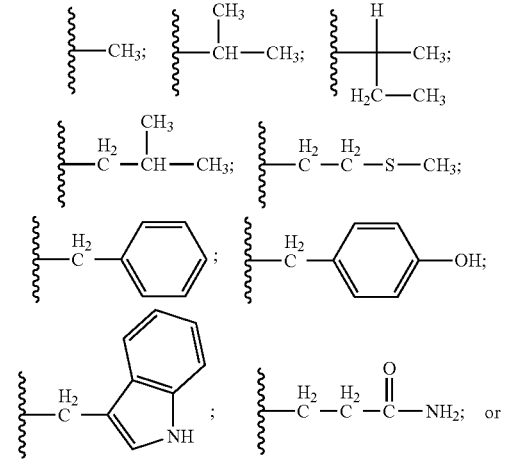

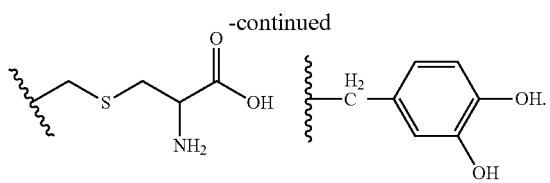

According to some embodiments of the general formula (III), $R^X$ is an amino acid side chain selected from the group consisting of arginine, lysine, serine, glycine, alanine, valine, phenylalanine, tyrosine, ornithine and 3,4-dihydroxyphenylalanine; or an O-phosphorylated amino acid side chain thereof.

According to some embodiments of the general formula (III), each one of $R_1$, $R_2$ and $R_5$ are H; $R_3$, and $R_4$ independently are H or —P(=O)(OR')$_2$; and R' is H.

According to preferable embodiments of the general formula (III), $R^X$ is an amino acid side chain selected from the group consisting of arginine, lysine, serine, glycine, alanine, valine, phenylalanine, tyrosine, ornithine and 3,4-dihydroxyphenylalanine; or an O-phosphorylated amino acid side chain thereof each one of $R_1$, $R_2$ and $R_5$ are H; $R_3$, and $R_4$ independently are H or —P(=O)(OR')$_2$; and R' is H.

According to some embodiments, the LDAA comprises a compounds represented by the formula (IV) or a pharmaceutically acceptable salt thereof:

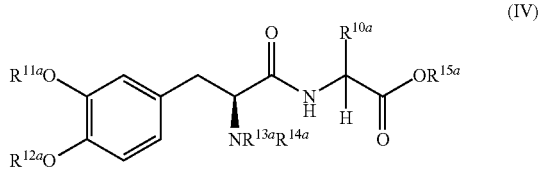

(IV)

wherein $R^{10a}$ is an amino acid side chain or an O-phosphorylated amino acid side chain thereof;
$R^{11a}$ and $R^{12a}$ are the same or different, and are each a hydrogen, an alkyl, a cycloalkyl, a phenyl, P(=O)(OR')$_2$, S(=O)(OH), or a glycosyl that may be substituted;
$R^{13a}$ and R' are the same or different, and are each a hydrogen, an alkyl, an alkenyl, an alkynyl, a cycloalkyl, a phenyl, —O—C(=O)—R', —C(=O)—OR', —C(=O)—R', —C(=S)—R', —O—C(=O)—NR'R", —O—C(=S)—NR'R", or —O—C(=O)—R"';

$R^{15a}$ is a is a hydrogen, an alkyl, a cycloalkyl or a phenyl;
R' and R" are the same or different, and are each a hydrogen, an alkyl, an alkenyl, a cycloalkyl or a phenyl, or form a group in which R' and R" together with an adjacent nitrogen atom form a heteroaryl;
and R''' is a hydrogen, an alkyl, an alkenyl or an alkynyl.

According to some embodiments, the LDAA comprises a compounds represented by the formula (V) or a pharmaceutically acceptable salt thereof:

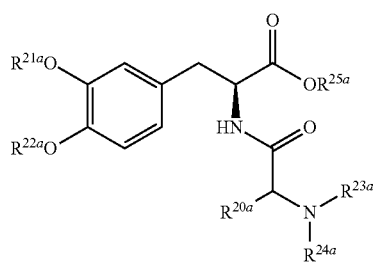

(V)

wherein $R^{20a}$ is an amino acid side chain that may be substituted;
$R^{21a}$ and $R^{22a}$ are the same or different and are each a hydrogen, an alkyl, an alkanoyl, P(=O)(OH)$_2$, S(=O)(OH) or a glycosyl that may be substituted;
and $R^{23a}$, $R^{24a}$, and $R^{25a}$ are the same or different, and are each a hydrogen or an alkyl).

In some embodiments, the LDAA is a compound represented by a formula (IV-1) or a pharmacologically acceptable salt thereof:

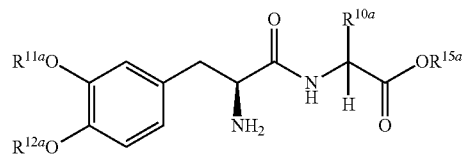

(IV-1)

wherein $R^{10a}$ is an amino acid side chain;
and $R^{11a}$ and $R^{12a}$ are the same or different and are each a hydrogen, S(=O)(OH) or a glycosyl that may be substituted, but $R^{11a}$ and $R^{12a}$ are not both each simultaneously a hydrogen).

Exemplary embodiments of the foregoing levodopa prodrugs are listed below in Tables A and B:

TABLE A

| Compound name |
| --- |
| (2S)-6-amino-2-[[(2S)-2-amino-3-(3-hydroxy-4-phosphonooxyphenyl)propanoyl]amino]hexanoic acid |
| (2S)-2-[[(2S)-2-amino-3-(3-hydroxy-4-phosphonooxyphenyl)propanoyl]amino]-3-(4-hydroxyphenyl)propanoic acid |
| (2S)-2-[[(2S)-2-amino-3-(3-hydroxy-4-phosphonooxyphenyl)propanoyl]amino]-5-carbamimidamide pentanoic acid; hydrochloride |
| (2S)-2-amino-3-(3-hydroxy-4-phosphonooxyphenyl)propionamide |
| (2S)-2-[[(2S)-2-amino-3-(3-hydroxy-4-phosphonooxyphenyl)propanoyl]amino]propanoic acid |
| 2-[[(2S)-2-amino-3-(3-hydroxy-4-phosphonooxyphenyl)propanoyl]amino]acetic acid |
| 2-[[(2S)-2-amino-3-(3-hydroxy-4-phosphonooxyphenyl)propanoyl]amino]ethanesulfonic acid |
| (2S)-2-[[(2S)-2-amino-3-(3-hydroxy-4-phosphonooxyphenyl)propanoyl]amino]-3-phenylpropanoic acid |

TABLE A-continued

| Compound name |
|---|
| (2S)-2-[[(2S)-2-amino-3-(3,4-dihydroxyphenyl)propanoyl]amino]-3-phosphonooxypropanoic acid |
| (2S)-2-[[(2S)-2-amino-3-(3-hydroxy-4-phosphonooxyphenyl)propanoyl]amino]-3-(3,4-dihydroxyphenyl)propanoic acid |
| (2S)-2-amino-6-[[(2S)-2-amino-3-(3-hydroxy-4-phosphonooxyphenyl)propanoyl]amino]hexanoic acid |
| (2S)-5-amino-2-[[(2S)-2-amino-3-(3-hydroxy-4-phosphonooxyphenyl)propanoyl]amino]pentanoic acid |
| (2S)-2-amino-5-[[(2S)-2-amino-3-(3-hydroxy-4-phosphonooxyphenyl)propanoyl]amino]pentanoic acid |
| (2S)-2-[[(2S)-2-amino-3-(3-hydroxy-4-phosphonooxyphenyl)propanoyl]amino]-3-hydroxypropanoic acid |
| (2S)-2-[[(2S)-2-amino-3-(3-hydroxy-4-phosphonooxyphenyl)propanoyl]amino]-3-methylbutanoic acid |
| (2S)-2-[[(2S)-2-amino-3-(3-hydroxy-4-phosphonooxyphenyl)propanoyl]amino]-3-(3-hydroxy-4-phosphonooxyphenyl)propanoic acid |
| (2S)-2-[[(2S)-2-amino-3-(4-hydroxy-3-phosphonooxyphenyl)propanoyl]amino]-3-(4-hydroxy-3-phosphonooxyphenyl))propanoic acid |
| (2S)-2-[[(2S)-2-amino-3-(3,4-dihydroxyphenyl)propanoyl]amino]-3-(4-phosphonooxyphenyl)propanoic acid |

TABLE B

| Structural formula | Physical property values |
|---|---|
| | MS(ESI); m/z 441.4 [M + H]+ |
| | MS(ESI); m/z 434.4 [M + H]+ |
| | MS(ESI); m/z 277.2 [M + H]+ |
| | MS(ESI); m/z 349.2 [M + H]+ |

TABLE B-continued
| Structural formula | Physical property values |
|---|---|
| 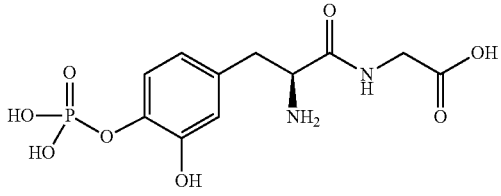 | MS(ESI); m/z 335.2 [M + H]+ |
| 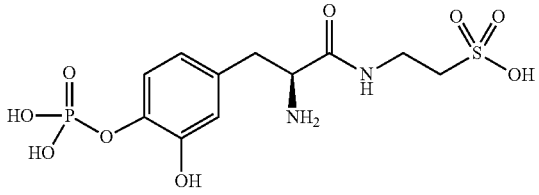 | MS(ESI); m/z 383.1 [M − H]− |
| 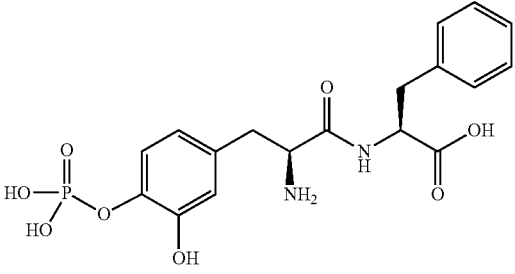 | MS(ESI); m/z 425.4 [M + H]+ |
| 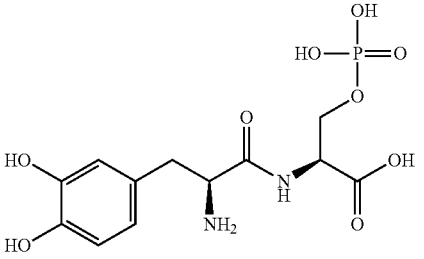 [SMILES: N[C@@H](Cc1ccc(O)c(O)c1)C(=O)N[C@@H](COP(=O)(O)O)C(=O)O] | MS(ESI); m/z 365.2 [M + H]+ |
| 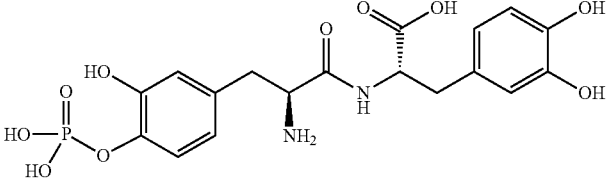 | MS(ESI); m/z 457.1 [M + H]+ |
| 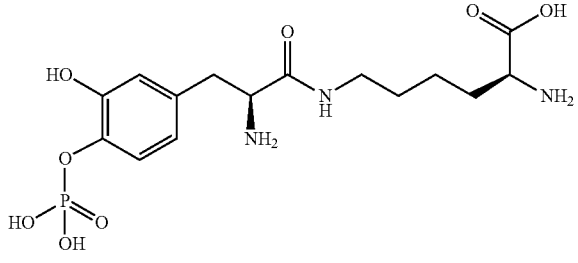 [SMILES: N[C@@H](CCCCNC(=O)[C@@H](N)Cc1ccc(OP(=O)(O)O)c(O)c1)C(=O)O] | MS(ESI); m/z 406.2 [M + H]+ |

TABLE B-continued

| Structural formula | Physical property values |
| --- | --- |
| [structure: 3-hydroxy-4-phosphonooxy-phenylalanyl-ornithine] | MS(ESI); m/z 392.2 [M + H]+ |
| [structure: 3-hydroxy-4-phosphonooxy-phenylalanyl-(β-amino)-ornithine isomer] | MS(ESI); m/z 392.0 [M + H]+ |
| [structure: 3-hydroxy-4-phosphonooxy-phenylalanyl-serine] | MS(ESI); m/z 365.1 [M + H]+ |
| [structure: 3-hydroxy-4-phosphonooxy-phenylalanyl-valine] | MS(ESI); m/z 377.1 [M + H]+ |
| [structure: bis(phosphonooxy-hydroxyphenyl) dipeptide] | MS(ESI); m/z 537.3 [M + H]+ |
| [structure: 3,4-dihydroxyphenylalanyl-(4-phosphonooxy)tyrosine] | MS(ESI); m/z 441.3 [M + H]+ |

TABLE B-continued

| Structural formula | Physical property values |
| --- | --- |
| [chemical structure] | MS (ESI); m/z 1034.4 [M + H]+ |
| [chemical structure] | MS(ESI); m/z 1025.6 [M + H]+ |
| [chemical structure] | MS(ESI); m/z 681.4 [M + H]+ |

TABLE B-continued

| Structural formula | Physical property values |
| --- | --- |
| (structure) | MS(ESI); m/z 843.4 [M + H]+ |
| (structure) | MS(ESI); m/z 829.4 [M + H]+ |
| (structure) | MS(ESI); m/z 919.5 [M + H]+ |

TABLE B-continued
| Structural formula | Physical property values |
|---|---|
| 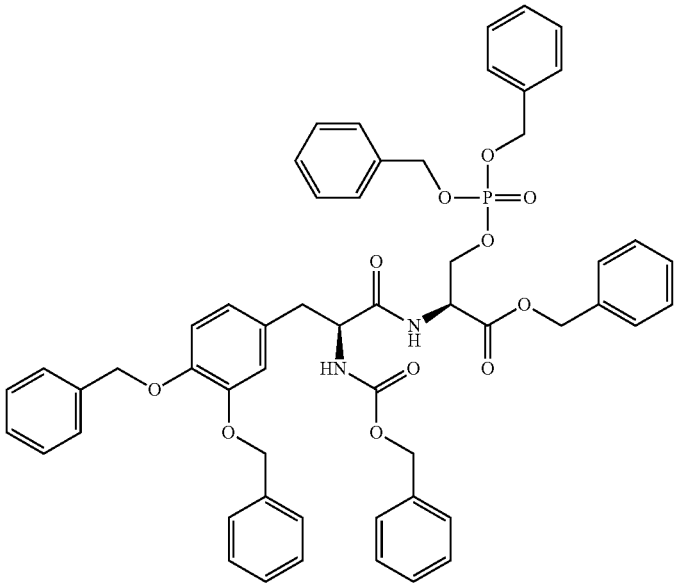 [SMILES: O=C(N[C@@H](Cc1ccc(OCc2ccccc2)c(OCc2ccccc2)c1)C(=O)N[C@@H](COP(=O)(OCc1ccccc1)OCc1ccccc1)C(=O)OCc1ccccc1)OCc1ccccc1] | MS (ESI); m/z 949.5 [M + H]+ |
| 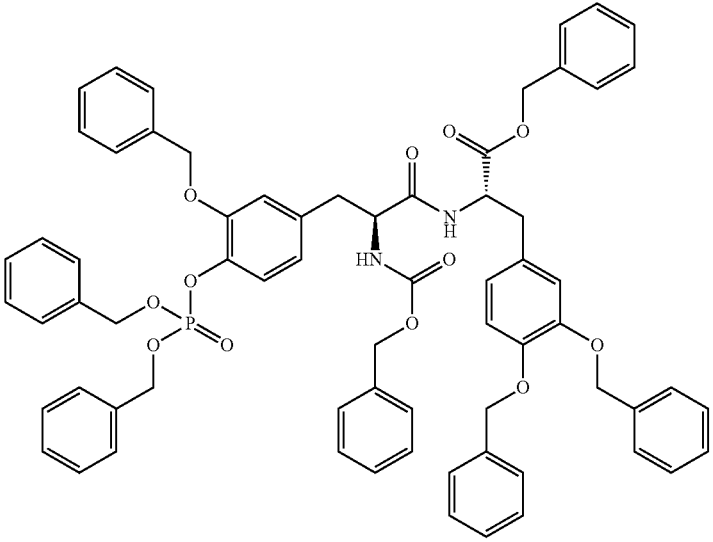 [SMILES: O=C(N[C@@H](Cc1ccc(OP(=O)(OCc2ccccc2)OCc2ccccc2)c(OCc2ccccc2)c1)C(=O)N[C@@H](Cc1ccc(OCc2ccccc2)c(OCc2ccccc2)c1)C(=O)OCc1ccccc1)OCc1ccccc1] | MS (ESI); m/z 1129.5 [M − H]− |

TABLE B-continued

| Structural formula | Physical property values |
|---|---|
| | MS (ESI); m/z 1018.4 [M − H]− |
| | MS (ESI); m/z 1018.4 [M − H]− |
| | MS (ESI); m/z 857.3 [M − H]+ |

TABLE B-continued
| Structural formula | Physical property values |
|---|---|
| 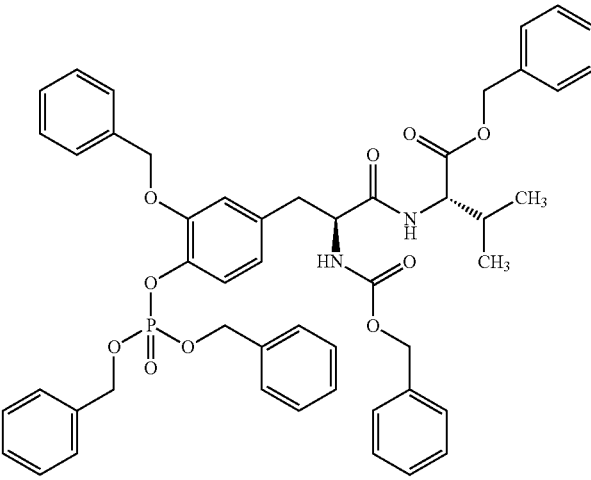 [SMILES: CC(C)[C@H](NC(=O)[C@H](Cc1ccc(OP(=O)(OCc2ccccc2)OCc2ccccc2)c(OCc2ccccc2)c1)NC(=O)OCc1ccccc1)C(=O)OCc1ccccc1] | MS (ESI); m/z 869.6 [M − H]− |
| 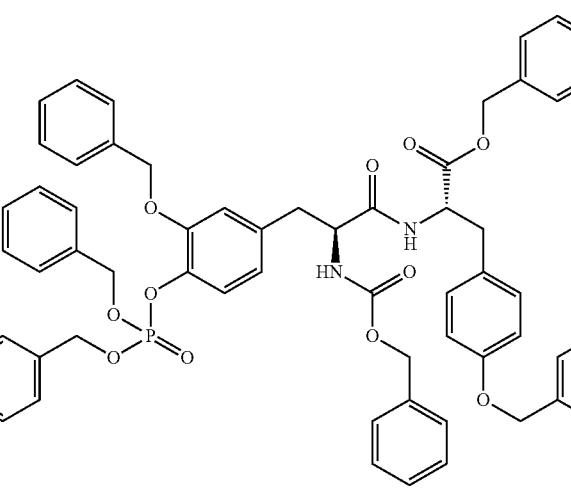 | MS (ESI); m/z 1025.6 [M + H]+ |
| 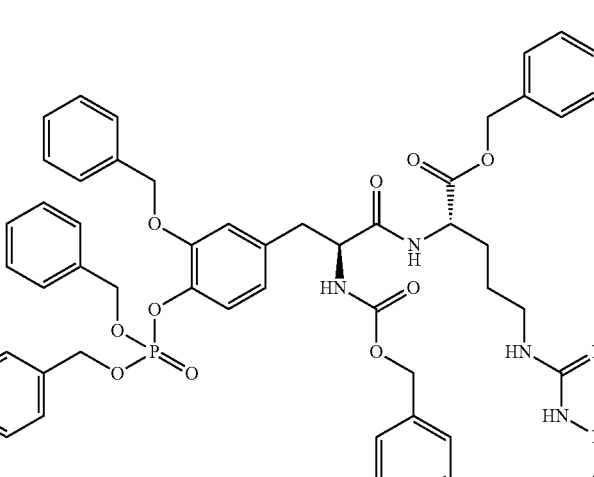 | MS(ESI); m/z 973.6[M + H]+ |

TABLE B-continued

| Structural formula | Physical property values |
|---|---|
| | MS(ESI); m/z 789.3 [M + H]+ |
| | MS(ESI); m/z 765.7 [M + H]+ |
| | MS(ESI); m/z 421.4 [M + H]+ |

TABLE B-continued

| Structural formula | Physical property values |
|---|---|
| (structure) | MS(ESI); m/z 583.5 [M + H]+ |
| (structure) | MS(ESI); m/z 659.5 [M + H]+ |
| (structure) | MS(ESI); m/z 774.4 [M + H]+ |
| (structure) | MS(ESI); m/z 781.8 [M + H]+ |

TABLE B-continued

| Structural formula | Physical property values |
|---|---|
| (structure) | MS(ESI); m/z 779.6 [M − H]− |
| (structure) | MS(ESI); m/z 689.4[M + H]+ |
| (structure) | MS(ESI); m/z 765.5[M + H]+ |

TABLE B-continued
| Structural formula | Physical property values |
|---|---|
| 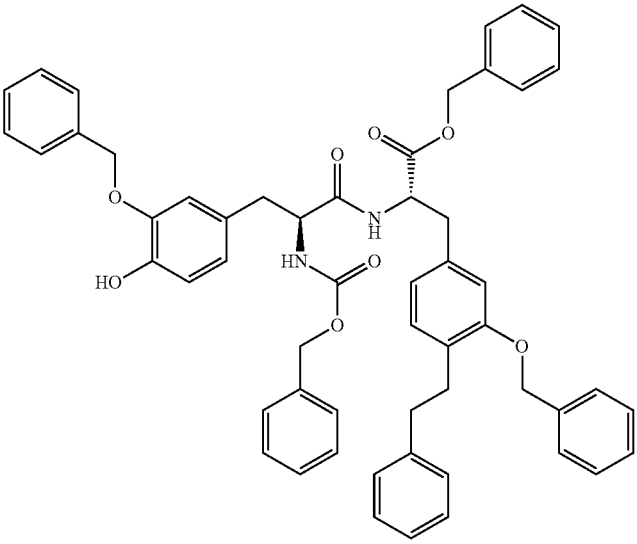 [SMILES: O=C(N[C@@H](Cc1ccc(O)c(OCc2ccccc2)c1)C(=O)N[C@@H](Cc1ccc(CCc2ccccc2)c(OCc2ccccc2)c1)C(=O)OCc1ccccc1)OCc1ccccc1] | MS(ESI); m/z 871.3 [M + H]+ |
| 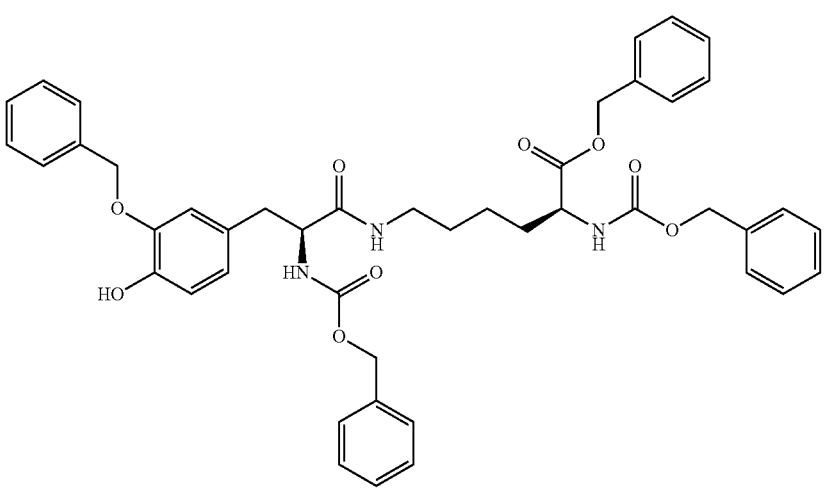 [SMILES: O=C(N[C@@H](Cc1ccc(O)c(OCc2ccccc2)c1)C(=O)NCCCC[C@H](NC(=O)OCc1ccccc1)C(=O)OCc1ccccc1)OCc1ccccc1] | MS(ESI); m/z 774.8[M + H]+ |

TABLE B-continued
| Structural formula | Physical property values |
|---|---|
| 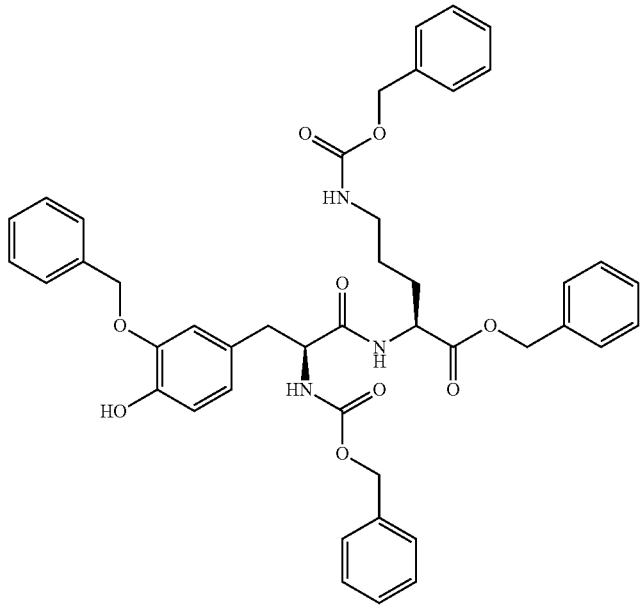 [SMILES: O=C(NCCC[C@H](NC(=O)[C@H](Cc1ccc(O)c(OCc2ccccc2)c1)NC(=O)OCc1ccccc1)C(=O)OCc1ccccc1)OCc1ccccc1] | MS(ESI); m/z 760.4 [M + H]+ |
| 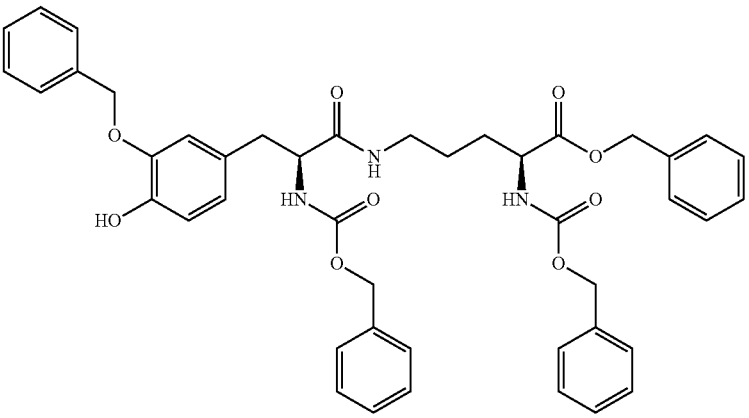 [SMILES: O=C(N[C@@H](Cc1ccc(O)c(OCc2ccccc2)c1)C(=O)NCCC[C@H](NC(=O)OCc1ccccc1)C(=O)OCc1ccccc1)OCc1ccccc1] | MS(ESI); m/z 760.4 [M + H]+ |
| 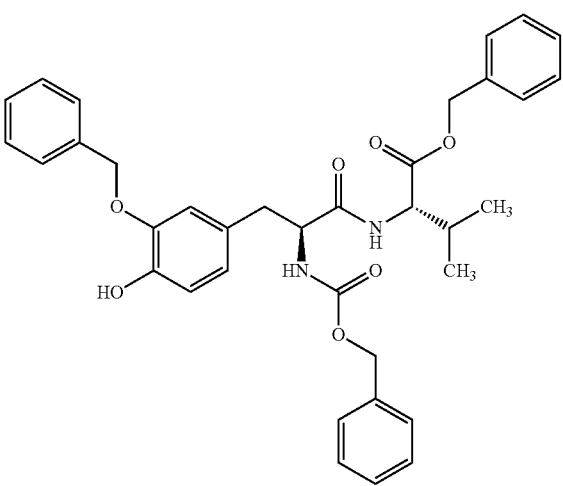 [SMILES: CC(C)[C@H](NC(=O)[C@H](Cc1ccc(O)c(OCc2ccccc2)c1)NC(=O)OCc1ccccc1)C(=O)OCc1ccccc1] | MS(ESI); m/z 611.6[M + H]+ |

TABLE B-continued

| Structural formula | Physical property values |
|---|---|
| (phosphorylated DOPA-Ala dipeptide structure) | MS (ESI); m/z 349.1 [M + H]+ |
| (phosphorylated DOPA-DOPA dipeptide structure) | MS (ESI); m/z 457.4 [M + H]+ |
| (phosphorylated DOPA N-acetyl structure) | MS (ESI); m/z 320.1 [M + H]+ |
| (phosphorylated DOPA-Val dipeptide structure) | MS (ESI); m/z 375.2 [M − H]− |
| (phosphorylated DOPA-Gly dipeptide structure) | MS (ESI); m/z 335.3 [M + H]+ |
| (phosphorylated DOPA-Glu dipeptide structure) | MS (ESI); m/z 405.0 [M − H]− |

TABLE B-continued

| Structural formula | Physical property values |
|---|---|
| (phosphorylated DOPA-ornithine structure) | MS (ESI); m/z 392.3 [M + H]+ |
| (phosphorylated DOPA-lysine structure) | MS (ESI); m/z 406.3 [M + H]+ |
| (DOPA-phosphoserine structure) | MS (ESI); m/z 365.1 [M + H]+ |
| (DOPA-phosphotyrosine structure) | MS (ESI); m/z 441.1 [M + H]+ |

TABLE B-continued
| Structural formula | Physical property values |
|---|---|
| 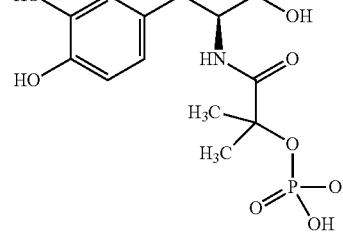 | MS (ESI); m/z 364.1 [M + H]+ |
| 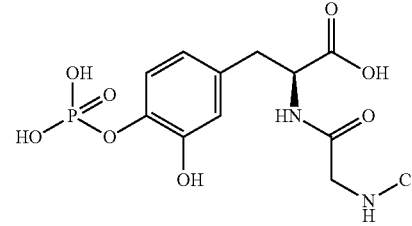 | MS (ESI); m/z 349.1 [M + H]+ |
| 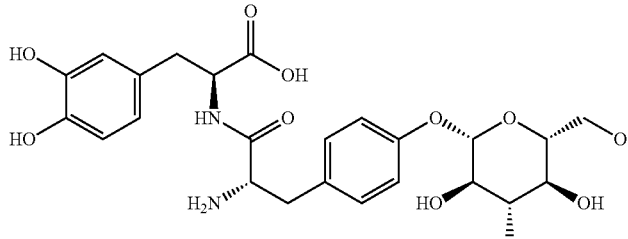 | MS (ESI); m/z 523.0 [M + H]+ |
| 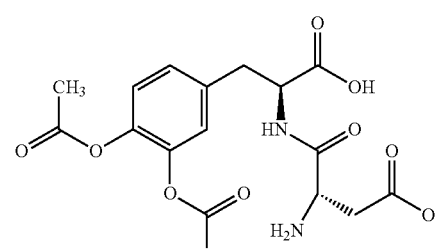 | MS (ESI); m/z 397.1 [M + H]+ |
| 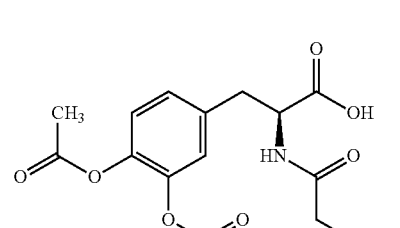 | MS (ESI); m/z 411.1 [M + H]+ |

TABLE B-continued

| Structural formula | Physical property values |
|---|---|
| (structure) | MS (ESI); m/z 324.1 [M + H]+ |
| (structure) | MS (ESI); m/z 411.1 [M + H]+ |
| (structure) | MS (ESI); m/z 495.0 [M − H]− |
| (structure) | MS (ESI); m/z 527.2 [M + H]+ |

TABLE B-continued
| Structural formula | Physical property values |
|---|---|
| 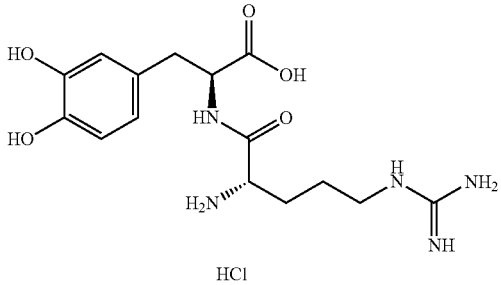 [SMILES: N=C(N)NCCC[C@H](N)C(=O)N[C@@H](Cc1ccc(O)c(O)c1)C(=O)O ; Cl] HCl | MS (ESI); m/z 354.2 [M + H]+ |
| 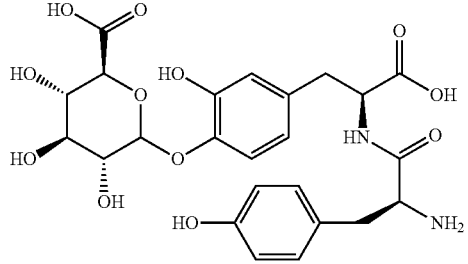 [SMILES: N[C@@H](Cc1ccc(O)cc1)C(=O)N[C@@H](Cc1ccc(OC2O[C@H](C(=O)O)[C@@H](O)[C@H](O)[C@H]2O)c(O)c1)C(=O)O] | — |
| 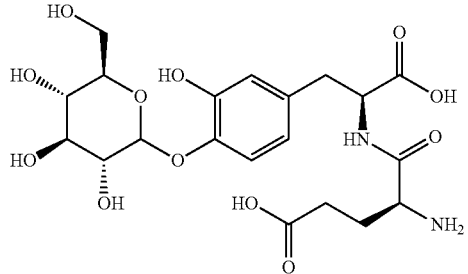 [SMILES: N[C@@H](CCC(=O)O)C(=O)N[C@@H](Cc1ccc(OC2O[C@H](CO)[C@@H](O)[C@H](O)[C@H]2O)c(O)c1)C(=O)O] | — |
| 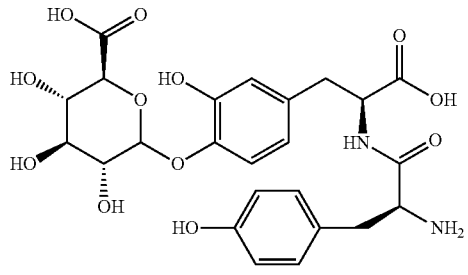 [SMILES: N[C@@H](Cc1ccc(O)cc1)C(=O)N[C@@H](Cc1ccc(OC2O[C@H](C(=O)O)[C@@H](O)[C@H](O)[C@H]2O)c(O)c1)C(=O)O] | — |
| 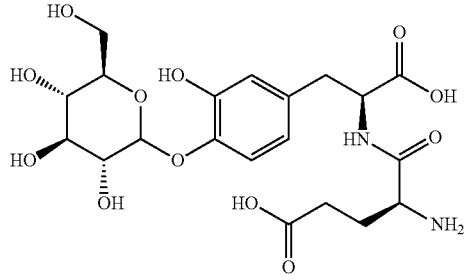 [SMILES: N[C@@H](CCC(=O)O)C(=O)N[C@@H](Cc1ccc(OC2O[C@H](CO)[C@@H](O)[C@H](O)[C@H]2O)c(O)c1)C(=O)O] | — |

TABLE B-continued

| Structural formula | Physical property values |
|---|---|
| [structure: glucuronide-O-phenyl ring with OH, CH2-CH(NH-C(O)-CH(NH2)-CH2-CH2-COOH)-COOH] | — |
| [structure: H3C-CH2-O-phenyl(OH)-CH2-CH(NH-C(O)-CH(NH2)-CH2-CH2-COOH)-COOH] | — |
| [structure: glucuronide-O-phenyl(OH)-CH2-CH(NH-C(O)-CH(NH2)-CH2-CH2-COOH)-COOH] | — |
| [structure: H3C-CH2-O-phenyl(OH)-CH2-CH(NH-C(O)-CH(NH2)-CH2-CH2-COOH)-COOH] | — |
| [structure: tribenzyl phosphate protected tyrosine derivative with Cbz-protected amino acid bearing methylenedioxy(methyl)(ethoxy) benzodioxole] | MS (ESI); m/z 929.3 [M − H]− |

TABLE B-continued

| Structural formula | Physical property values |
|---|---|
| (structure) | MS (ESI); m/z 843.7 [M + H]+ |
| (structure) | MS (ESI); m/z 1148.6 [M + H + NH2]+ |
| (structure) | MS (ESI); m/z 680.3 [M + H]+ |

TABLE B-continued

| Structural formula | Physical property values |
|---|---|
| | MS (ESI); m/z 915.7 [M − H + HCO2H]− |
| | MS (ESI); m/z 873.6 [M − H + HCO2H]− |
| | MS (ESI); m/z 989.7 [M − H]− |
| | MS (ESI); m/z 1018.4 [M − H]− |

TABLE B-continued

| Structural formula | Physical property values |
|---|---|
| | MS (ESI); m/z 1034.8 [M + H]+ |
| | MS (ESI); m/z 949.2 [M+H]+ |
| | MS (ESI); m/z 1025.7 [M + H]+ |

TABLE B-continued

| Structural formula | Physical property values |
|---|---|
| (structure) | MS (ESI); m/z 814.4 [M + H]+ |
| (structure) | MS (ESI); m/z 843.7 [M + H]+ |
| (structure) | MS (ESI); m/z 638.6 [M + H − Boc]+ |

TABLE B-continued
| Structural formula | Physical property values |
|---|---|
| 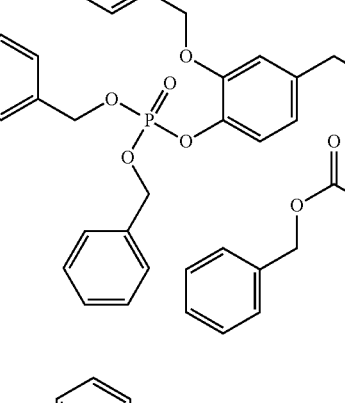 | MS (ESI); m/z 989.5 [M − H]− |
| 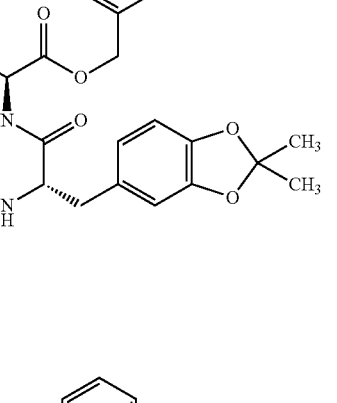 | MS (ESI); m/z 1019.3 [M − H]− |
| 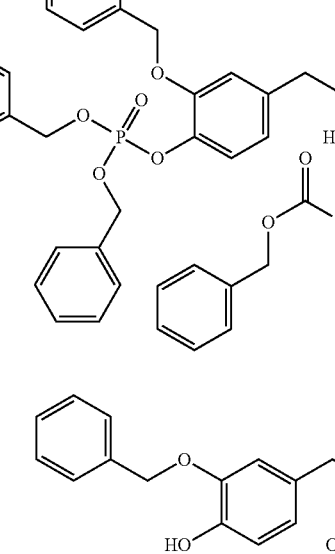 | MS (ESI); m/z 583.6 [M + H]+ |
| 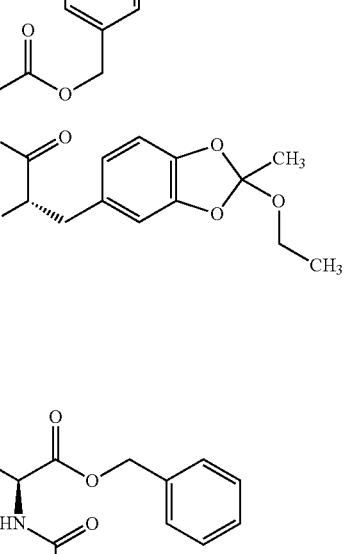 | MS (ESI); m/z 871.8 [M + H]+ |

TABLE B-continued

| Structural formula | Physical property values |
|---|---|
| (structure) | MS (ESI); m/z 611.6 [M + H]+ |
| (structure) | MS (ESI); m/z 569.5 [M + H]+ |
| (structure) | MS (ESI); m/z 731.4 [M + H]+ |
| (structure) | MS (ESI); m/z 760.2 [M + H]+ |
| (structure) | MS (ESI); m/z 774.7 [M + H]+ |

TABLE B-continued

| Structural formula | Physical property values |
| --- | --- |
| (structure) | MS (ESI); m/z 689.5 [M + H]+ |
| (structure) | MS (ESI); m/z 765.3 [M + H]+ |
| (structure) | MS (ESI); m/z 554.2 [M + H]+ |
| (structure) | MS (ESI); m/z 803.7 [M + H]+ |

TABLE B-continued
| Structural formula | Physical property values |
|---|---|
| 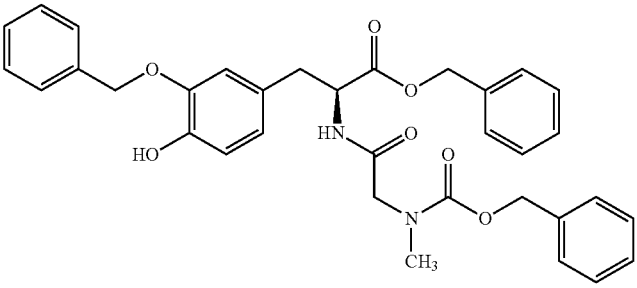 [SMILES: CN(CC(=O)N[C@@H](Cc1ccc(O)c(OCc2ccccc2)c1)C(=O)OCc1ccccc1)C(=O)OCc1ccccc1] | MS (ESI); m/z 581.3 [M − H]− |
| 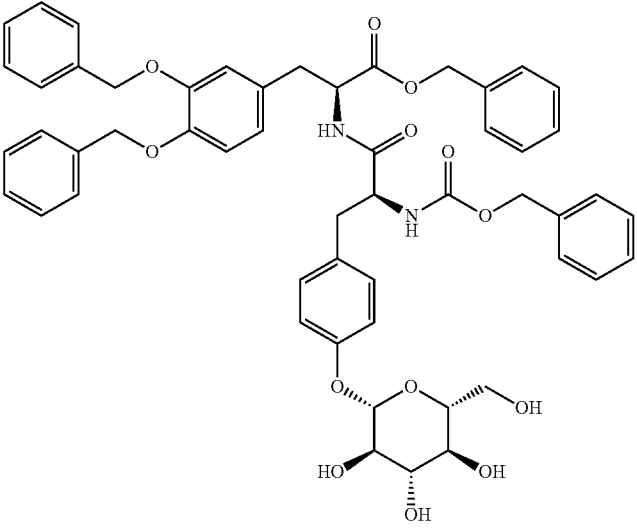 [SMILES: O=C(N[C@@H](Cc1ccc(O[C@@H]2O[C@H](CO)[C@@H](O)[C@H](O)[C@H]2O)cc1)C(=O)N[C@@H](Cc1ccc(OCc2ccccc2)c(OCc2ccccc2)c1)C(=O)OCc1ccccc1)OCc1ccccc1] | MS (ESI); m/z 927.7 [M + H]+ |
| 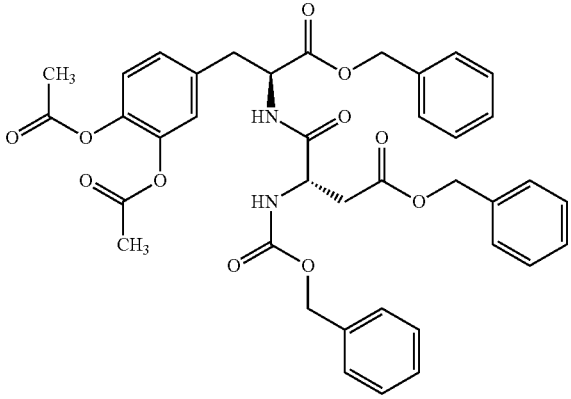 [SMILES: CC(=O)Oc1ccc(C[C@H](NC(=O)[C@H](CC(=O)OCc2ccccc2)NC(=O)OCc2ccccc2)C(=O)OCc2ccccc2)cc1OC(C)=O] | MS (ESI); m/z 711.4 [M + H]+ |
| 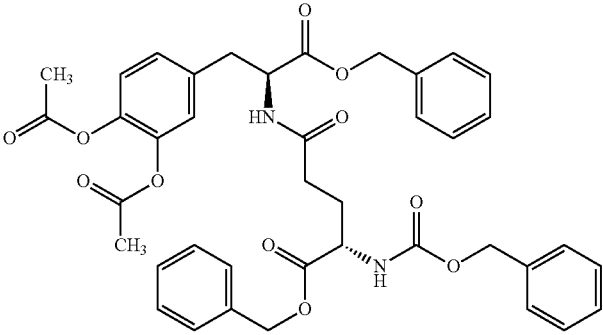 [SMILES: CC(=O)Oc1ccc(C[C@H](NC(=O)CC[C@H](NC(=O)OCc2ccccc2)C(=O)OCc2ccccc2)C(=O)OCc2ccccc2)cc1OC(C)=O] | MS (ESI); m/z 725.5 [M + H]+ |

TABLE B-continued

| Structural formula | Physical property values |
|---|---|
| (structure) | MS (ESI); m/z 725.4 [M + H]+ |
| (structure) | MS (ESI); m/z 729.3 [M − H]− |
| (structure) | MS (ESI); m/z 761.0 [M + H]+ |
| (structure) | MS (ESI); m/z 414.2 [M + H]+ |
| (structure) | MS (ESI); m/z 420.5 [M + H]+ |

TABLE B-continued

| Structural formula | Physical property values |
|---|---|
| (structure) | MS (ESI); m/z 680.3 [M + H]+ |
| (structure) | MS (ESI); m/z 468.3 [M + H]+ |
| (structure) | MS (ESI); m/z 638.3 [M + H]+ |

Further embodiments of the invention are directed to a levodopa amino acid conjugate (LDAA) selected from the group consisting of:

(2S)-2-amino-3-(3-hydroxy-4-phosphonooxyphenyl)propionamide;

2-[[(2S)-2-amino-3-(3-hydroxy-4-phosphonooxyphenyl)propanoyl]amino]ethanesulfonic acid;

(2S)-2-amino-6-[[(2S)-2-amino-3-(3-hydroxy-4-phosphonooxyphenyl)propanoyl]amino]hexanoic acid; or (2S)-2-amino-5-[[(2S)-2-amino-3-(3-hydroxy-4-phosphonooxyphenyl)propanoyl]amino]pentanoic acid.

Embodiments of the invention are directed to a levodopa-lanthionine conjugate (LD-LA) of the general formula (II-1) or (II-2):

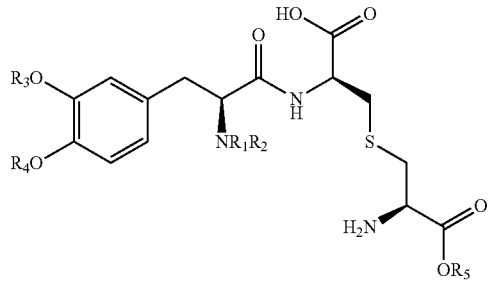

(II-1)

-continued (II-2)

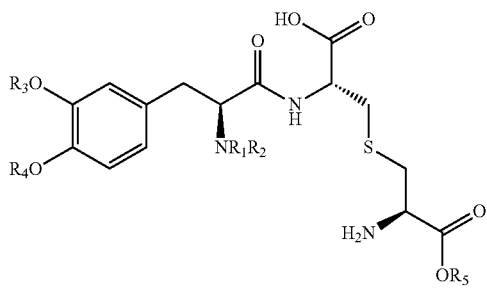

an enantiomer, diastereomer, racemate, ion, zwitterion, pharmaceutically acceptable salt thereof, or any combination thereof, wherein:

$R_1$ and $R_2$ each independently is selected from the group consisting of H, $(C_1$-$C_6)$alkyl, $(C_2$-$C_6)$alkenyl, $(C_2$-$C_6)$ alkynyl, $C_3$-$C_6$cycloalkyl, phenyl, —O—C(=O)—R', —C(=O)—OR', —C(=O)—R', —C(=S)—R', —O—C(=O)—NR'R', —O—C(=S)—NR'R', or —O—C(=O)—R";

$R_3$ and $R_4$ each independently is selected from the group consisting of H, $(C_1$-$C_3)$alkyl, $C_3$-$C_6$cycloalkyl, phenyl, or —P(=O)(OR')$_2$;

$R_5$ is selected from the group consisting of H, $(C_1$-$C_3)$ alkyl, $C_3$-$C_6$cycloalkyl and phenyl;

R' is each independently selected from the group consisting of H, $(C_1$-$C_6)$alkyl, $(C_2$-$C_6)$alkenyl, $C_3$-$C_6$cycloalkyl, phenyl, and heteroaryl bonded to the nitrogen through a ring carbon; and R" is selected from the group consisting of a $(C_1$-$C_6)$alkyl, $(C_2$-$C_6)$alkenyl, and $(C_2$-$C_6)$alkynyl.

According to some embodiments, each one of $R_1$, $R_2$, $R_3$, $R_4$ and $R_5$ are H.

According to some embodiments, the levodopa prodrug comprises a levodopa amino acid conjugate (LDAA) of the general formula (VI):

(VI)

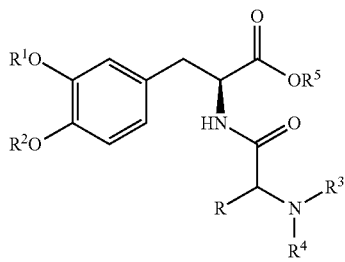

wherein R is an amino acid side chain that may be substituted;

$R^1$ and $R^2$ may be the same or different, and are each independently a hydrogen atom, a $C_1$-$C_6$ alkyl, a $C_1$-$C_6$ alkanoyl, a phosphono, a sulfino, or a glycosyl that may be substituted, provided that $R^1$ and $R^2$ are not hydrogen atom at the same time;

$R^3$ and $R^4$ may be the same or different, and are each independently a hydrogen atom or a $C_1$-$C_6$ alkyl; and $R^5$ is a hydrogen atom, provided that following compounds are excluded;

(2S)-2-[(2-aminoacetyl)amino]-3-(3,4-diacetyloxyphenyl) propanoic acid, (2S)-2-[[(2S)-2-amino-6-[(2-chlorophenyl)methoxycarbonylamino]hexanoyl]amino]-3-(3,4-dimethoxyphenyl) propanoic acid, (2S)-2-[[(2S)-2-amino-3-(3,4-dihydroxyphenyl)propanoyl] amino]-3-(4-hydroxy-3-methoxyphenyl)propanoic acid, (2S)-2-[[(2S)-2-amino-3-phenylpropanoyl]amino]-3-(3,4-dimethoxyphenyl)propanoic acid, (2S)-2-[[(2R)-2-amino-3-phenylpropanoyl]amino]-3-(3,4-diacetyloxyphenyl)propanoic acid, and (2S)-2-[[(2S)-2-amino-5-methoxy-5-oxopentanoyl]amino]-3-(3,4-dimethoxyphenyl)propanoic acid.

In certain embodiments, the levodopa prodrug comprises a levodopa amino acid conjugate (LDAA) of the general formula (VI) or a pharmaceutically acceptable salt thereof, wherein R3, R4 and R5 are hydrogen atoms. In certain embodiments, $R^1$ and $R^2$ are the same or different, and are each a hydrogen atom, an acetyl or a phosphono, provided that $R^1$ and $R^2$ are not hydrogen atom at the same time.

In certain embodiments, the disclosure further relates to a pharmaceutically acceptable salt thereof, wherein $R_3$, $R_4$ and $R_5$ are hydrogen atoms, $R^1$ is a hydrogen atom, and $R^2$ is a phosphono.

In certain embodiments, the disclosure further relates to the LDAA according to any one of the above embodiments, or a pharmaceutically acceptable salt thereof, wherein an amino acid of the amino acid side chain is a glutamic acid, valine, alanine, lysine, 3,4-dihydroxyphenylalanine or tyrosine.

In certain embodiments, the LDAA is selected from the group consisting of:

(2S)-2-[[(2S)-2-amino-3-phosphonooxypropanoyl]amino]-3-(3,4-dihydroxyphenyl)propanoic acid, (2S)-2-[[(2S)-2-amino-3-(4-phosphonooxyphenyl)propanoyl]amino]-3-(3,4-dihydroxyphenyl)propanoic acid, (2S)-2-amino-5-[[(1S)-1-carboxy-2-(3,4-diacetoxyphenyl) ethyl]amino]-5-oxo-pentanoic acid, (2 S)-3-(3,4-dihydroxyphenyl)-2-[(2-methyl-2-phosphonooxypropanoyl)amino]propanoic acid, and (2S)-2-[[(2S)-2-amino-3-[4-[(2S,3R,4S,5S,6R)-3,4,5-trihydroxy-6-(hydroxymethyl)oxan-2-yl]oxyphenyl]propanoyl]amino]-3-(3,4-dihydroxyphenyl)propanoic acid.

In certain embodiments, the LDAA is selected from the group consisting of:

(2S)-2-[[(2S)-2-aminopropanoyl]amino]-3-(3-hydroxy-4-phosphonooxyphenyl) propanoic acid, (2S)-2-[[(2S)-2-amino-3-(3,4-dihydroxyphenyl) propanoyl] amino]-3-(3-hydroxy-4-phosphonooxyphenyl) propanoic acid, (2S)-2-[[(2S)-2,6-diaminohexanoyl]amino]-3-(3-hydroxy-4-phosphonooxyphenyl) propanoic acid, and (2 S)-2-[[(2S)-2-amino-3-(4-phosphonooxyphenyl) propanoyl]amino]-3-(3,4-dihydroxyphenyl) propanoic acid, wherein the levodopa amino acid is presented using the Japanese IUPAC name.

In certain embodiments, the LDAA comprises a levodopa-lysine (LD-Lys) or levodopa-alanine (LD-Ala) conjugate of the formula (VII-1):

(VII-1)

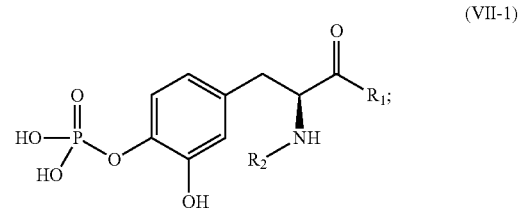

wherein one of $R_1$ or $R_2$ is lysine or alanine, wherein the other is hydrogen. According to some embodiments, $R_1$ is hydrogen and $R_2$ is lysine or alanine.

In certain embodiments, the LDAA comprises a levodopa-tyrosine (LD-Tyr) conjugate of the formula (VII-2):

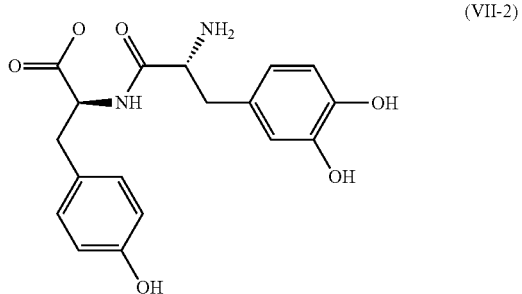 [SMILES: N[C@H](Cc1ccc(O)c(O)c1)C(=O)N[C@@H](Cc1ccc(O)cc1)C(=O)O]

(VII-2)

an enantiomer, diastereomer, racemate, ion, zwitterion, pharmaceutically acceptable salt thereof, or any combination thereof.

In some embodiments, a first pharmaceutical composition comprising a levodopa moiety, e.g., LD-Tyr may further comprise a stabilizer. In certain embodiments, the first pharmaceutical composition comprises between about 0.1% to about 30% w/v of the stabilizer. In certain embodiments, the first pharmaceutical composition comprises between about 1.5 to about 20% w/v of the stabilizer. For example, the first pharmaceutical composition can comprise between about 1.5 and about 5.0%, about 1.5 and about 10.0% w/v, about 1.5 and about 15.0% w/v, about 1.5 and about 20.0% w/v, about 1.5 and about 25.0% w/v, about 3.0 and about 5.0% w/v, about 3.0 and about 10.0% w/v, about 3.0 and about 15.0% w/v, about 3.0 and about 20.0% w/v, about 3 and about 25.0% w/v, about 3.0 and about 30.0% w/v, about 5.0 and about 10.0% w/v, about 5 and about 15.0% w/v, about 5.0 and about 20.0% w/v, about 5.0 and about 25.0% w/v, about 5.0 and about 30.0% w/v, about 7.0 and about 10.0% w/v, about 7.0 and about 15.0% w/v, about 7.0 and about 20.0% w/v, about 7.0 and about 25.0% w/v, about 7.0 and about 30.0% w/v, about 10.0 and about 15.0% w/v, about 10.0 and about 20.0% w/v, about 10 and about 25.0% w/v, about 10.0 and about 30.0% w/v, about 15.0 and about 20.0% w/v, about 15.0 and about 25.0% w/v, about 15.0 and about 30.0% w/v of the stabilizer. In certain embodiments, the first pharmaceutical composition comprises two, three, or four stabilizers in combination, wherein each individual stabilizer is present in an amount as described above, or the combination of stabilizers is present in an amount as described above.

According to certain embodiments, the stabilizer comprises a base. In other embodiments the first pharmaceutical composition comprises a stabilizer and further comprises a base, e.g., in order to provide the composition with a pre-defined pH. According to some embodiments, the base is selected from NaOH, NH$_4$OH, Ca(OH)$_2$, ammonium hydroxide, arginine, lysine, magnesium hydroxide, potassium hydroxide, meglumine, tromethamine (TRIS), triethylamine, ethylenediamine, diethylamine, ethanolamine, diisopropylethylamine, diazabicycloundecene or any combination thereof. The first pharmaceutical composition may comprise between about 0.1 to about 30.0% w/v of a base. According to some embodiments, the first pharmaceutical composition comprises between about 0.1 to about 1.0% w/v, between about 1.0 to about 2.0% w/v, between about 2.0 to about 3.0% w/v, between about 3.0 to about 4.0% w/v, between about 4.0 to about 5.0% w/v, between about 5.0 to about 6.0% w/v, between about 6.0 to about 7.0% w/v, between about 8.0 to about 9.0% w/v, between about 9.0 to about 10.0% w/v, between about 10.0 to about 11.0% w/v, between about 11.0 to about 12.0% w/v, between about 12.0 to about 13.0% w/v, between about 13.0 to about 14.0% w/v, between about 14.0 to about 15.0% w/v, between about 15.0 to about 16.0% w/v, between about 16.0 to about 17.0% w/v, between about 17.0 to about 18.0% w/v, between about 18.0 to about 19.0% w/v, between about 19.0 to about 20.0% w/v, between about 20.0 to about 21.0% w/v, between about 21.0 to about 22.0% w/v, between about 22.0 to about 23.0% w/v, between about 23.0 to about 24.0% w/v, between about 24.0 to about 25.0% w/v, between about 25.0 to about 26.0% w/v, between about 26.0 to about 27.0% w/v, between about 27.0 to about 28.0% w/v, between about 28.0 to about 29.0% w/v, between about 29.0 to about 30.0% w/v, of a base.

In certain embodiments, the stabilizer comprises a base selected from the group consisting of arginine, lysine, NaOH, NH$_4$OH, tris(hydroxymethyl)aminomethane (TRIS), ethylenediamine, diethylamine, ethanolamine, diethanolamine, meglumine, triethanolamine, and any combination thereof. In certain embodiments, the base is selected from the group consisting of arginine, lysine, NH$_4$OH, ethylenediamine, diethylamine, ethanolamine, diethanolamine, meglumine, and a combination thereof. In certain embodiments, the base is selected from the group consisting of L-Arg, diethylamine, and a combination thereof. In certain embodiments, the base is selected from the group consisting of L-Arg, ethanolamine, and a combination thereof. In certain embodiments, the first pharmaceutical composition comprises between about 0.1% to about 30.0% w/v of the base. In certain embodiments, the first pharmaceutical composition comprises between about 1.5% to about 20.0% w/v of the base. For example, the first pharmaceutical composition can comprise between about 1.5 to about 5.0% w/v, between about 1.5 to about 10.0% w/v, between about 1.5 to about 15.0% w/v, about 1.5 to about 20.0% w/v, between about 1.5 to about 25.0% w/v, between about 3.0 to about 5.0% w/v, about 3.0 to about 10.0% w/v, between about 3.0 to about 15.0% w/v, between about 3.0 and about 20.0% w/v, about 3.0 to about 25.0% w/v, between about 3.0 to about 30.0% w/v, about 5.0 to about 10.0% w/v, between about 5.0 to about 15.0% w/v, between about 5.0 to about 20.0% w/v, between about 5.0 to about 25.0% w/v, between about 5.0 to about 30.0% w/v, between about 7.0 to about 10.0% w/v, between about 7.0 to about 15.0% w/v, between about 7.0 to about 20.0% w/v, between about 7.0 to about 25.0% w/v, about 7.0 to about 30.0% w/v, between about 10.0 to about 15.0% w/v, between about 10.0 to about 20.0% w/v, between about 10.0 to about 25.0% w/v, between about 10.0 to about 30.0% w/v, between about 15.0 to about 20.0% w/v, between about 15.0 to about 25.0% w/v, between about 15.0 to about 30.0% w/v of the base. In certain embodiments, the first pharmaceutical composition comprises two, three, or four stabilizers in combination. For example, in certain embodiments, the pharmaceutical composition comprises arginine and an additional base selected from the group consisting of lysine, NH$_4$OH, ethylenediamine, diethylamine, ethanolamine, diethanolamine, meglumine. In certain embodiments, each individual stabilizer is present in an amount as described above, or the combination of stabilizers is present in an amount as described above. In certain embodiments, arginine is present in an amount of from about 7.0 to about 8.0% w/v and the additional base is present in an amount of from about 3.0 to about 8.0% w/v. In certain embodiments, the first pharmaceutical formulation comprises about 7.0 to about 8.0% (e.g., 7.2%) w/v L-Arg and about 3.0 to about 8.0% (e.g., about 5.4%) w/v diethylamine. In certain embodiments, the first pharmaceutical formulation comprises about 7.0 to about 8.0% (e.g., 7.2%) w/v L-Arg and about 2.0 to about 7.0% (e.g., about 4.5%) w/v ethanolamine.

In certain embodiments, the stabilizer includes one or more of polyethylene glycol (e.g., PEG-300, PEG-400, PEG-600), propylene glycol, choline, sodium or ammonium ions, an amino acid (e.g., Lys or His), benzyl alcohol, ethanol, group IIA metal complexes (e.g., $Ca^{2+}$ salts such as $CaCl_2$ and Ca ascorbate), citric acid, lactic acid, or acetic acid, an electrophile (e.g., a Lewis acid such as $Na^+$, $K^+$, $Ca^{2+}$, boron compounds, $Fe^{3+}$, $Al^{3+}$, $Cu^{2+}$ and α-β unsaturated carbonyls such as maleic acid), phosphate buffer, $Zn^{2+}$ ions, a reducing sugar such as glucose, sodium acetate, hydroxypropyl beta cyclodextrin, soluble beta cyclodextrin a medium chain triglyceride such as octanoic acid, mixed micelles glycocholate/lecithin, N-methyl pyrrolidone, dimethyl acetamide, soybean oil, sesame oil, castor oil, dimethyl sulfoxide, glycerine, tris buffer, ammonium acetate, or guanidine HCl. In certain embodiments, the stabilizer includes a surfactant such as those described herein, e.g., poloxamer, Tween-80, Tween-20, and Kolliphor.

In some embodiments, the stabilizer that prevents or slows precipitation of the first pharmaceutical formulation and/or that prevents or slows the accumulation of impurities in the first pharmaceutical formulation. LD-Tyr has a propensity to form a diketopiperazine (DKP) impurity as shown in the scheme below.

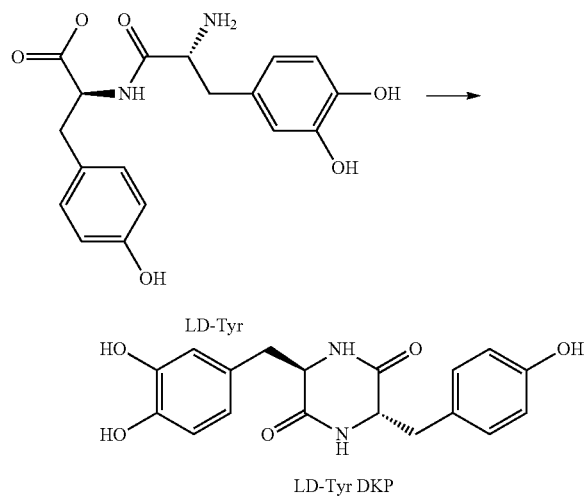

LD-Tyr

LD-Tyr DKP

Accordingly, in certain embodiments, a stabilizer as described herein is added to or is included in the first pharmaceutical composition and prevents diketopiperazine formation. Thus, in certain embodiments, the pharmaceutical composition comprises less than about 1.5% w/v LD-Tyr-diketopiperazine (LD-Tyr DKP) after two weeks at 2-8° C. In certain embodiments, the first pharmaceutical composition comprises less than about 0.8% w/v LD-Tyr-diketopiperazine after two weeks at 2-8° C. For example, the pharmaceutical composition can comprise less than about 0.8% w/v, 0.7% w/v, 0.6% w/v, 0.5% w/v, 0.4% w/v, 0.3% w/v, 0.2% w/v or 0.1% w/v LD-Tyr-diketopiperazine after two weeks at 2-8° C. In certain embodiments, the first pharmaceutical composition comprises less than about 4.0% w/v LD-Tyr-diketopiperazine after two weeks at 25° C. For example, the first pharmaceutical composition can comprise less than about 5.0% w/v, 4.5% w/v, 4.0% w/v, 3.5% w/v, 3.0% w/v, 2.5% w/v, 2.0% w/v, 1.5% w/v or 1.0% w/v LD-Tyr-diketopiperazine after two weeks at 25° C. In certain embodiments, the first pharmaceutical composition comprises no more than about 4.0% w/v LD-Tyr-diketopiperazine after two weeks at 25° C. Methods for measuring DKP are known in the art and include, for example, high-performance liquid chromatography (HPLC) and liquid chromatography-mass spectrometry (LC-MS).

According to some embodiments, the levodopa moiety compound is present in a pharmaceutically acceptable salt form. According to some embodiments, the levodopa moiety salt is selected from a trifluoroacetic acid (TFA) salt, an HCl salt, fumaric acid salt, lactate salt, maleic acid salt, gluceptic acid salt, phosphoric acid salt, sulfuric acid salt, HBr salt, nitric acid salt, acetic acid salt, propionic acid salt, hexanoic acid salt, cyclopentanepropionic acid salt, glycolic acid salt, pyruvic acid salt, lactic acid salt, hippuric acid salt, methanesulfonic acid salt, ascorbic acid salt, malonic acid salt, oxalic acid salt, maleic acid salt, tartaric acid salt, citric acid salt, succinic acid salt, benzoic acid salt, cinnamic acid salt, a sulfonic acid salt, lauryl sulfuric acid salt, gluconic acid salt, glutamic acid salt, hydroxynaphthoic acid salt, salicylic acid salt, stearic acid salt, muconic acid salt, an alkali metal salt, such as lithium salt, sodium salt or potassium salt, an alkaline earth metal salt, such as calcium salt or magnesium salt, an aluminum salt, an ethanolamine salt, diethanolamine salt, triethanolamine salt, N-methylglucamine salt, dicyclohexylamine salt, adipate salt, alginate salt, ascorbate salt, aspartate salt, benzenesulfonate salt, bisulfate salt, borate salt, butyrate salt, camphorate butyrate salt, camphorsulfonate butyrate salt, digluconate butyrate salt, dodecylsulfate butyrate salt, ethanesulfonate butyrate salt, glucoheptonate butyrate salt, glycerophosphate butyrate salt, gluconate butyrate salt, hemisulfate butyrate salt, heptanoate butyrate salt, hydroiodide butyrate salt, 2-hydroxy-ethanesulfonate butyrate salt, lactobionate butyrate salt, laurate butyrate salt, methanesulfonate butyrate salt, 2-naphthalenesulfonate butyrate salt, nicotinate butyrate salt, oleate butyrate salt, palmitate butyrate salt, pamoate butyrate salt, pectinate butyrate salt, persulfate butyrate salt, 3-phenylpropionate butyrate salt, phosphate butyrate salt, picrate butyrate salt, pivalate butyrate salt, tartrate butyrate salt, thiocyanate butyrate salt, p-toluenesulfonate butyrate salt, undecanoate butyrate salt, valerate salts, or any combination thereof.

The first pharmaceutical composition may comprise between about 2.5 to about 70% w/v of an levodopa moiety, an enantiomer, diastereomer, racemate, ion, zwitterion, pharmaceutically acceptable salt thereof, or any combination thereof, or any combination of two or more levodopa moieties, enantiomers, diastereomers, racemates, ions, zwitterions, pharmaceutically acceptable salts thereof, or any combination thereof. According to some embodiments, the first pharmaceutical composition comprises between about 2.5 to about 5% w/v, between about 5 to about 10% w/v, between about 10 to about 15% w/v, between about 15 to about 20% w/v, between about 20 to about 25% w/v, between about 25 to about 30% w/v, between about 30 to about 35% w/v, between about 35 to about 40% w/v, between about 40 to about 45% w/v, between about 45 to about 50% w/v, between about 50 to about 55% w/v, between about 55 to about 60% w/v, between about 60 to about 65% w/v, between about 65 to about 70% w/v, between about 10 to about 12.5% w/v, between about 12.5 to about 17.5% w/v, between about 17.5 to about 22.5% w/v, between about 22.5 to about 27.5% w/v, between about 27.5 to about 32.5% w/v, between about 32.5 to about 37.5% w/v, between about 37.5 to about 42.5% w/v, between about 42.5 to about 45% w/v, about 10% w/v, about 12.5% w/v, about 15% w/v, about 17.5% w/v, about 20% w/v, about 22.5% w/v, about 25% w/v, about 27.5% w/v, about 30% w/v, about 32.5% w/v, about 35% w/v, about 37.5% w/v, about 40% w/v, about 42.5% w/v, about 45% w/v, about 47.5% w/v, about 50% w/v, about 52.5% w/v, about 55% w/v, about 57.5% w/v, about 60% w/v, about 62.5% w/v, about 65% w/v, about 67.5% w/v, about 70% w/v of the levodopa moiety, an enantiomer, diastereomer, racemate, ion, zwitterion, pharmaceutically acceptable salt thereof, or any combination thereof, or any combination of two or more levodopa moieties, enantiomers, diastereomers, racemates, ions, zwitterions, pharmaceutically acceptable salts thereof, or any combination thereof.

In some embodiments, the first pharmaceutical composition comprises a carbidopa moiety, e.g., carbidopa and/or a carbidopa prodrug, wherein the carbidopa prodrug may be selected from a group consisting of any of formulas (VIII)-(XIV) or a pharmacologically acceptable salt thereof:

compounds represented by the formula (VIII):

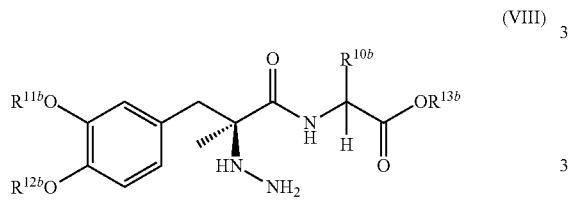

(VIII)

wherein $R^{10b}$ is an amino acid side chain;
$R^{11b}$ and $R^{12b}$ are the same or different and are each a hydrogen, an alkyl, $P(=O)(OH)_2$, $S(=O)(OH)$, or a glycosyl that may be substituted;
and $R^{13b}$ is a hydrogen or an alkyl, compounds represented by the formula (IX):

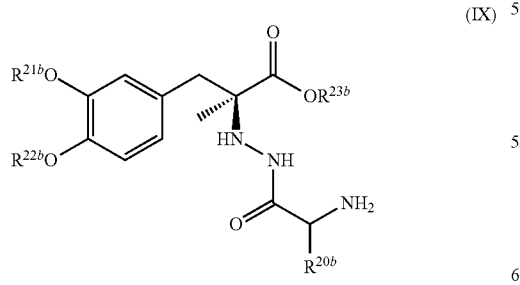

(IX)

wherein $R^{20b}$ is an amino acid side chain;
$R^{21b}$ and $R^{22b}$ are the same or different and are each a hydrogen, an alkyl, $P(=O)(OH)_2$, $S(=O)(OH)$, or a glycosyl that may be substituted;
and $R^{23b}$ is a hydrogen or an alkyl, compounds represented by the formula (X):

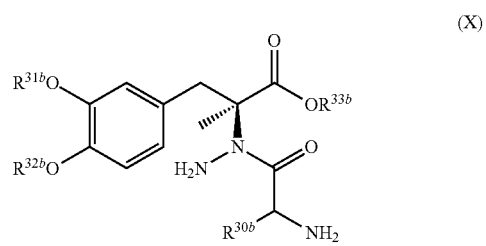

(X)

wherein $R^{30b}$ is an amino acid side chain;
$R^{31b}$ and $R^{32b}$ are the same or different and are each a hydrogen, an alkyl, $P(=O)(OH)_2$, $S(=O)(OH)$, or a glycosyl that may be substituted;
and $R^{33b}$ is a hydrogen or an alkyl, compounds represented by the formula (XI):

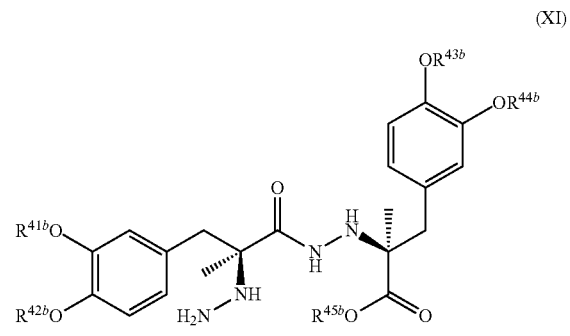

(XI)

wherein $R^{41b}$ and $R^{42b}$ are the same or different and are each a hydrogen, an alkyl, $P(=O)(OH)_2$, $S(=O)(OH)$, or a glycosyl that may be substituted;
$R^{43b}$ and $R^{44b}$ are the same or different and are each a hydrogen, an alkyl, $P(=O)(OH)_2$, $S(=O)(OH)$, or a glycosyl that may be substituted, or form a group in which $R^{43b}$ and $R^{44b}$ together form an alkylene that may be substituted;
and $R^{45b}$ is a hydrogen or an alkyl), compounds represented by the formula (XII):

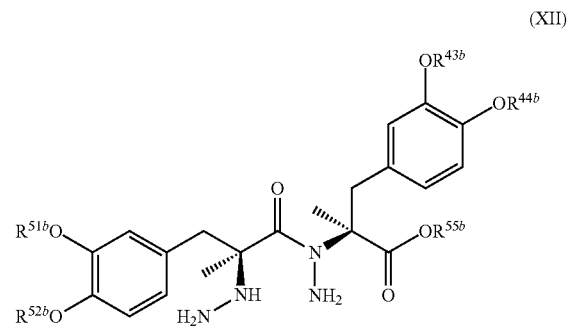

(XII)

wherein $R^{51b}$ and $R^{52b}$ are the same or different and are each a hydrogen, an alkyl, $P(=O)(OH)_2$, $S(=O)(OH)$, or a glycosyl that may be substituted;
$R^{53b}$ and $R^{54b}$ are the same or different and are each a hydrogen, an alkyl, $P(=O)(OH)_2$, $S(=O)(OH)$, or a glycosyl that may be substituted, or form a group in which $R^{53b}$ and $R^{54b}$ together form an alkylene that may be substituted;

and $R^{55b}$ is a hydrogen or an alkyl), compounds represented by the formula (XIII):

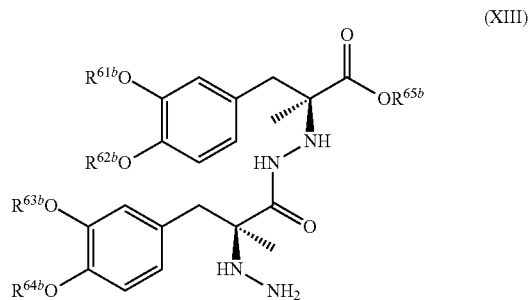

(XIII)

wherein $R^{61b}$ and $R^{62b}$ are the same or different and are each a hydrogen, an alkyl, $P(=O)(OH)_2$, $S(=O)(OH)$, or a glycosyl that may be substituted;

$R^{63b}$ and $R^{64b}$ are the same or different and are each a hydrogen, an alkyl, $P(=O)(OH)_2$, $S(=O)(OH)$, or a glycosyl that may be substituted, or form a group in which $R^{63b}$ and $R^{64b}$ together form an alkylene that may be substituted;

and $R^{65b}$ is a hydrogen or an alkyl), and compounds represented by the formula (XIV):

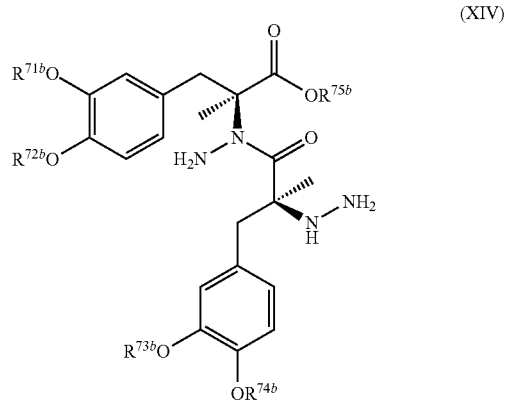

(XIV)

wherein $R^{71b}$ and $R^{72b}$ are the same or different and are each a hydrogen, an alkyl, $P(=O)(OH)_2$, $S(=O)(OH)$, or a glycosyl that may be substituted;

$R^{73b}$ and $R^{74b}$ are the same or different and are each a hydrogen, an alkyl, $(=O)(OH)_2$, $S(=O)(OH)$, or a glycosyl that may be substituted, or form a group in which $R^{73b}$ and $R^{74b}$ together form an alkylene that may be substituted;

and $R^{75b}$ is a hydrogen or an alkyl).

In some embodiments, the first pharmaceutical composition comprises a combination of any of the foregoing levodopa prodrugs and carbidopa prodrugs. In some embodiments, the first pharmaceutical composition comprises a combination of levodopa and any of the carbidopa prodrugs described herein. According to further embodiments, the first pharmaceutical composition comprises carbidopa and any of the levodopa prodrugs described herein. It is noted that the first pharmaceutical composition may comprise any number of levodopa moieties and/or carbidopa moieties. Thus, according to some embodiments, the first pharmaceutical composition comprises any combination of at least one levodopa moiety and at least one carbidopa moiety, e.g., a combination of levodopa and a carbidopa prodrug, a combination of carbidopa and a levodopa prodrug, a combination of levodopa, a levodopa prodrug, and carbidopa, a combination of a levodopa prodrug, a carbidopa prodrug and carbidopa. A combination of levodopa, carbidopa, a levodopa prodrug and a carbidopa prodrug, and the like.

In some embodiments, the first pharmaceutical composition comprises a carbidopa prodrug represented by a formula (VIII) or a pharmacologically acceptable salt thereof, wherein $R^{10b}$ is an amino acid side chain; $R^{11b}$ and $R^{12b}$ are the same or different and are each a hydrogen, an alkyl, $P(=O)(OH)_2$, $S(=O)(OH)$, or a glycosyl that may be substituted; and $R^{13b}$ is a hydrogen or an alkyl). In certain embodiments, $R^{11b}$ and $R^{12b}$ are the same or different and are each a hydrogen or $P(=O)(OH)_2$, and $R^{13b}$ is a hydrogen.

In some embodiments, the first pharmaceutical composition comprises a carbidopa prodrug represented by a formula (IX) or a pharmacologically acceptable salt thereof, wherein $R^{20b}$ is an amino acid side chain; $R^{21b}$ and $R^{22b}$ are the same or different and are each a hydrogen, an alkyl, $P(=O)(OH)_2$, $S(=O)(OH)$, or a glycosyl that may be substituted; and $R^{23b}$ is a hydrogen or an alkyl. In some embodiments, $R^{21b}$ and $R^{22b}$ are the same or different and are each a hydrogen or $P(=O)(OH)_2$, and $R^{23b}$ is a hydrogen.

In some embodiments, the first pharmaceutical composition comprises a carbidopa prodrug represented by a formula (X) or a pharmacologically acceptable salt thereof, wherein $R^{30b}$ is an amino acid side chain; $R^{31b}$ and $R^{32b}$ are the same or different and are each a hydrogen, an alkyl, $P(=O)(OH)_2$, $S(=O)(OH)$, or a glycosyl that may be substituted; and $R^{33b}$ is a hydrogen or an alkyl). In some embodiments, $R^{31b}$ and $R^{32b}$ are the same or different and are each a hydrogen or $P(=O)(OH)_2$, and $R^{33b}$ is a hydrogen.

In some embodiments, the first pharmaceutical composition comprises a carbidopa prodrug represented by a formula (XI) or a pharmacologically acceptable salt thereof, wherein $R^{41b}$ and $R^{42b}$ are the same or different and are each a hydrogen, an alkyl, $P(=O)(OH)_2$, $S(=O)(OH)$, or a glycosyl that may be substituted; $R^{43b}$ and $R^{44b}$ are the same or different and are each a hydrogen, an alkyl, $P(=O)(OH)_2$, $S(=O)(OH)$, or a glycosyl that may be substituted, or form a group in which $R^{43b}$ and $R^{44b}$ together form an alkylene that may be substituted; and $R^{45b}$ is a hydrogen or an alkyl). In some embodiments, $R^{41b}$ and $R^{42b}$ are the same or different and are each a hydrogen or $P(=O)(OH)_2$, and $R^{45b}$ is a hydrogen.

In some embodiments, the first pharmaceutical composition comprises a carbidopa prodrug represented by a formula (XII) or a pharmacologically acceptable salt thereof, wherein $R^{51b}$ and $R^{52b}$ are the same or different and are each a hydrogen, an alkyl, $P(=O)(OH)_2$, $S(=O)(OH)$, or a glycosyl that may be substituted; $R^{53b}$ and $R^{54b}$ are the same or different and are each a hydrogen, an alkyl, $P(=O)(OH)_2$, $S(=O)(OH)$, or a glycosyl that may be substituted, or form a group in which $R^{53b}$ and $R^{54b}$ together form an alkylene that may be substituted; and $R^{55b}$ is a hydrogen or an alkyl). In some embodiments, $R^{51b}$ and $R^{52b}$ are the same or different and are each a hydrogen or $P(=O)(OH)_2$, and $R^{55b}$ is a hydrogen.

In some embodiments, the first pharmaceutical composition comprises a carbidopa prodrug represented by a formula (XIII) or a pharmacologically acceptable salt thereof, wherein $R^{61b}$ and $R^{62b}$ are the same or different and are each a hydrogen, an alkyl, $P(=O)(OH)_2$, $S(=O)(OH)$, or a glycosyl that may be substituted; $R^{63b}$ and $R^{64b}$ are the same or different and are each a hydrogen, an alkyl, $P(=O)(OH)_2$, $S(=O)(OH)$, or a glycosyl that may be substituted, or form a group in which $R^{63b}$ and $R^{64b}$ together form an alkylene that may be substituted; and $R^{65b}$ is a hydrogen or an alkyl. In some embodiments, $R^{61b}$ and $R^{62b}$ are the same or different and are each a hydrogen or $P(=O)(OH)_2$, and $R^{65b}$ is a hydrogen.

In some embodiments, the first pharmaceutical composition comprises a carbidopa prodrug represented by a formula (XIV) or a pharmacologically acceptable salt thereof, wherein $R^{71b}$ and $R^{72b}$ are the same or different and are each a hydrogen, an alkyl, $P(=O)(OH)_2$, $S(=O)(OH)$, or a glycosyl that may be substituted; $R^{73b}$ and $R^{74b}$ are the same or different and are each a hydrogen, an alkyl, $P(=O)(OH)_2$, $S(=O)(OH)$, or a glycosyl that may be substituted, or form a group in which $R^{73b}$ and $R^{74b}$ together form an alkylene that may be substituted; and $R^{75b}$ is a hydrogen or an alkyl. In some embodiments, $R^{71b}$ and $R^{72b}$ are the same or different and are each a hydrogen or $P(=O)(OH)_2$, and $R^{75b}$ is a hydrogen.

In some embodiments, an alkyl refers to a linear or branched saturated hydrocarbon group having 1-6 carbon atoms ($C_{1-6}$). In particular, a group having 1-4 carbon atoms ($C_{1-4}$) is preferable. Specific examples thereof include methyl, ethyl, n-propyl, i-propyl, n-butyl, t-butyl, n-pentyl, i-pentyl, n-hexyl, and the like.

In some embodiments, an alkoxy means a monovalent group in which the above alkyl is bonded to one oxygen atom, and examples thereof include linear or branched alkyl-O— having 1-6 carbon atoms ($C_{1-6}$). Specific examples thereof include methoxy, ethoxy, n-propoxy, i-propoxy, n-butoxy, t-butoxy, and the like.

In some embodiments, an alkenyl means a linear or branched unsaturated hydrocarbon chain having 2-6 carbon atoms having one carbon-carbon double bond, and examples thereof include vinyl, propenyl, butenyl, and various branched chain isomers of these. Preferably, an alkenyl means a linear or branched unsaturated hydrocarbon chain having 2-4 carbon atoms.

In some embodiments, an alkynyl refers to a monovalent group of a linear or branched hydrocarbon chain having one or more triple bonds, and, for example, means a linear or branched alkynyl having 2-6 carbon atoms. Specific examples thereof include 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl, and the like.

In some embodiments, an alkylene refers to a linear or branched saturated hydrocarbon divalent group having 1-6 carbon atoms ($C_{1-6}$), and specific examples thereof include methylene, ethylene, trimethylene, tetramethylene, and the like.

Here, examples of the alkylene in $R^{43b}$ and $R^{44b}$, the alkylene in $R^{53b}$ and $R^{54b}$, the alkylene in $R^{63b}$ and $R^{64b}$ and the alkylene in $R^{73b}$ and $R^{74b}$ preferably include methylene and ethylene, and the alkylenes may each be substituted. Examples of such substituent groups include alkyl, alkoxy, and the like, and it may be substituted with 1-3 identical or different substituent groups.

In some embodiments, an alkanoyl refers to a monovalent group in which the above-described alkyl is bonded to a carbonyl, and examples thereof include a linear or branched alkyl-CO— having 1-6 carbon atoms ($C_{1-6}$). Specific examples thereof include acetyl, propionyl, butyryl, pivaloyl, pentanoyl, hexanoyl, heptanoyle, and the like.

In the present invention, a cycloalkyl refers to a monocyclic saturated hydrocarbon group having 3-8 carbon atoms ($C_{3-8}$). Specific examples thereof include cyclopropyl, cyclobutyl, cyclopentyl, cyclohexyl, cycloheptyl, and the like.

In some embodiments, an amino acid side chain refers to an amino acid side chain of a natural, synthetic, non-natural or non-protein-producing amino acid, and examples of the amino acid include arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, tryptophan, lanthionine, selenocysteine, pyrrolidine, ADDA amino acid ((2S, 3S, 4E, 6E, 8S, 9S)-3-amino-9-methoxy-2,6,8-trimethyl-10-phenyldeca-4,6-dienoicacid), β-alanine, 4-aminobenzoic acid, γ-aminobutyric acid, S-aminoethyl-L-cysteine, 2-aminoisobutyric acid, aminolevulinic acid, azetidine-2-carboxylic acid, canalin, canavanine, carboxyglutamic acid, chloroalanine, cystine, dehydroalanine, diaminopimelic acid, dihydroxyphenylglycine, endouracidine, homoserine, 4-phenylglycine, hydroxyproline, hypusine, β-Leucine, norleucine, norvaline, ornithine, penicillamine, placohipaphorin, pyroglutamic acid, quisqualic acid, sarcosine, theanine, tranexamic acid, trichromic acid, 3,4-dihydroxyphenylalanine, and the like. Examples of $R^{10a}$ preferably include an amino acid side chain of arginine, lysine, alanine, valine, tyrosine and 3,4-dihydroxyphenylalanine. Examples of $R^{20a}$ preferably include an amino acid side chain of glutamic acid, valine, alanine, lysine, 3,4-dihydroxyphenylalanine and tyrosine. Examples of $R^{10b}$ preferably include an amino acid side chain of tyrosine and lysine. Examples of $R^{20b}$ preferably include an amino acid side chain of alanine and lysine. Examples of $R^{30b}$ preferably include an amino acid side chain of alanine and lysine.

For example, amino acid side chains represented by $R^{10a}$, $R^{20a}$, $R^{10b}$, $R^{20b}$, and $R^{30b}$ are represented by the following.

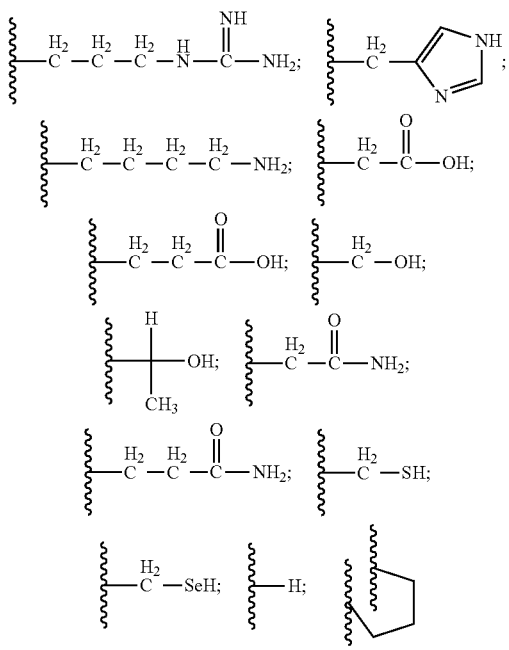

(An amino acid side chain of proline, wherein, $R^{10a}$, $R^{20a}$, $R^{10b}$, $R^{20b}$, $R^{30b}$ each form a bond with a nitrogen atom of a peptide bond of each compound);

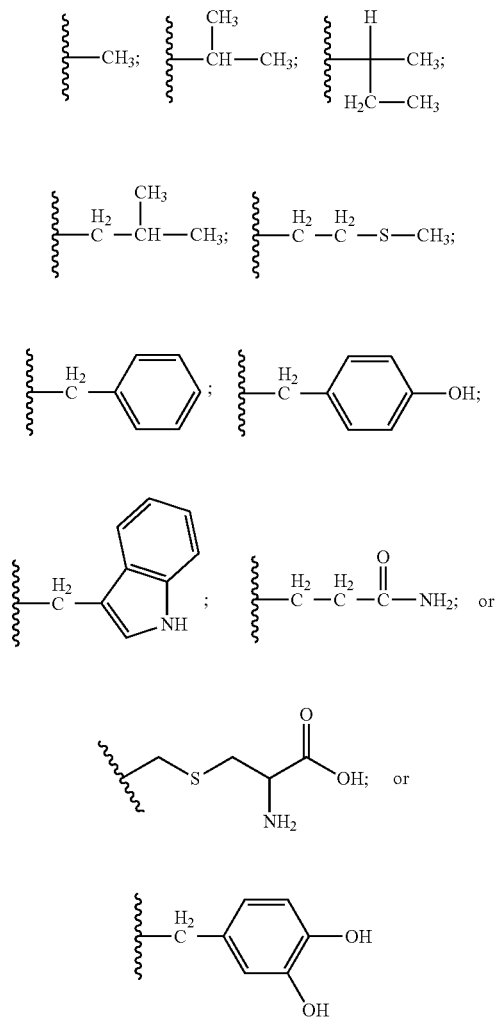

Here, the amino acid side chain in the present invention may be substituted, and examples thereof include —P(O)(OR$_6$)$_2$ (where R$_6$ is a hydrogen, an alkyl, or the like), a glucosyl group (such as [(2R, 3S, 4R, 5S, 6R)-3,4,5-trihydroxy-6-(hydroxymethyptetrahydropyran-2-yl]), a group that bonds to another adjacent group to form an alkylene group that may be substituted (examples of substituent groups include an alkyl group, an alkoxy group, and the like), and the like. Examples of substituted amino acid side chains include those in which a tyrosine side chain, a serine side chain, a threonine side chain, or an amino acid side chain having a hydroxy such as (3,4-dihydroxyphenyl)methyl is substituted, and specific examples thereof include phosphonooxymethyl, (4-phosphonooxyphenyl)methyl, [4-[(2S, 3R, 4S, 5S, 6R)-3,4,5-trihydroxy-6-(hydroxymethyptetrahydropyran-2-yl]oxyphenyl]methyl, (2,2-dimethyl-1,3-benzodioxol-5-yl)methyl, (2-ethoxy-2-methyl-1,3-benzodioxol-5-yl)methyl, and the like.

In the present invention, monosaccharides that are the source of glycosyl include aldoses such as glucose (dextrose), ribose, erythrose, xylose, arabinose, mannose, and galactose, as well as ketoses such as ribulose, psicose, fructose, sorbose, and tagatose. These monosaccharides may be of d-form, l-form or dl-form.

Monosaccharides described herein may be substituted, and examples of substituent groups include a carbonyl group, an acetylamino group, a sulfinooxy group, a phosphonooxy group, and the like. Specific examples of substituted monosaccharides include glucuronic acid, N-acetylglucosamine, α-D-Glucopyranose-6-(hydrogen sulfate), and the like.

In some embodiments, the group in which R' and R" together, and together with a nitrogen atom, form a heteroaryl refers to a 5-10-membered aromatic heterocycle group containing 1-4 heteroatoms independently selected from a group consisting of a sulfur atom, an oxygen atom, and a nitrogen atom, and a monocyclic or bicyclic heteroaryl is preferable. A 5-10-membered monocyclic heteroaryl containing 1-3 heteroatoms independently selected from a group consisting of a sulfur atom, an oxygen atom, and a nitrogen atom is more preferable. Specific examples thereof include pyrrolyl, furanyl, thienyl, imidazolyl, pyrazolyl, oxazolyl, isoxazolyl, thiazolyl, triazolyl, tetrazolyl, pyridil, pyrazinyl, pyrimidinyl, pyridadinyl, thiazinyl, triazinyl, indrill, isoindrill, indazolyl, benzoimidazolyl, benthiazolyl, benzofuranyl, quinolyl, isoquinolyl, imidazopyridyl, benzopyranyl, and the like. Pyrrolyl, furanyl, thienyl, imidazolyl, pyrazolyl, oxazolyl, isoxazolyl, thiazolyl, triazolyl, tetrazolyl, pyridil, pyrazinyl, pyrimidinyl, pyridadinyl, thiazinyl, triazinyl, and the like are preferable. In particular, pyrrolyl, thienyl, imidazolyl, pyrazolyl, oxazolyl, isoxazolyl, thiazolyl, triazolyl, pyridil, pyrazinyl, pyrimidinel, pyridadinyl, and the like are preferable.

When a compound has asymmetric carbon atoms in molecules thereof, the compound can exist as multiple stereoisomers (that is, diastereomeric isomers, and optical isomers) based on the asymmetric carbon atoms. However, the contemplated compounds include any one of these stereoisomers and mixtures thereof.

The compounds of the present invention include compounds labeled with isotopes (for example, $^3$H, $^{13}$C, $^{14}$C, $^{15}$N, $^{18}$F, $^{32}$P, $^{35}$P, $^{125}$I, and the like) and include deuterium converters.

Examples of pharmacologically acceptable salts of the compounds of the present invention include inorganic acid addition salts (such as salts of hydrochloric acid, hydrobromic acid, hydroiodic acid, sulfuric acid, phosphoric acid, and the like), organic acid addition salts (such as salts of methanesulfonic acid, benzenesulfonic acid, p-toluenesulfonic acid, formic acid, acetic acid, trifluoroacetic acid, oxalic acid, citric acid, malonic acid, fumaric acid, glutaric acid, adipic acid, maleic acid, tartrate acid, succinic acid, mandelic acid, malic acid, pantothenic acid, methyl sulfuric acid, and the like), inorganic base addition salts (such as salts of sodium, potassium, calcium, magnesium, and the like), salts of amino acids (such as salts of glutamic acid, aspartic acid, arginine, lysine, and the like), and the like.

The compounds of the present invention or pharmacologically acceptable salts thereof include any of intramolecular salts or adducts thereof, solvates or hydrates thereof, and the like. It is noted that any of the compounds disclosed herein, including any variations, such as labeled compounds, salts, hydrates, prodrugs, etc., may be included in the first pharmaceutical composition.

Exemplary embodiments of the foregoing carbidopa prodrugs are listed below in Table C:

TABLE C
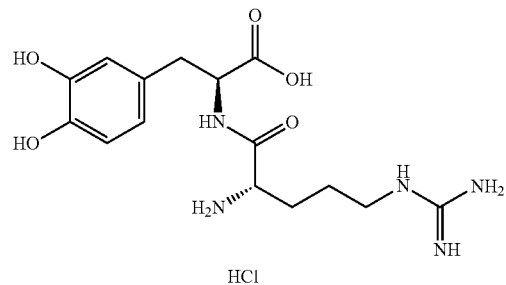 [SMILES: N=C(N)NCCC[C@H](N)C(=O)N[C@@H](Cc1ccc(O)c(O)c1)C(=O)O ; Cl]
MS (ESI); m/z 354.2 [M + H]+
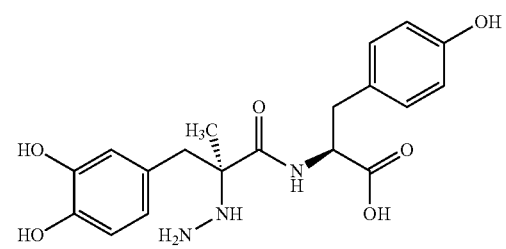 [SMILES: C[C@@](Cc1ccc(O)c(O)c1)(NN)C(=O)N[C@@H](Cc1ccc(O)cc1)C(=O)O]
MS (ESI); m/z 390.3 [M + H]+
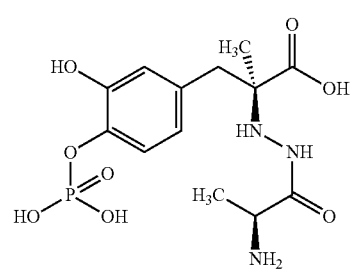 [SMILES: C[C@H](N)C(=O)NN[C@](C)(Cc1ccc(OP(=O)(O)O)c(O)c1)C(=O)O]
MS (ESI); m/z 378.0 [M + H]+
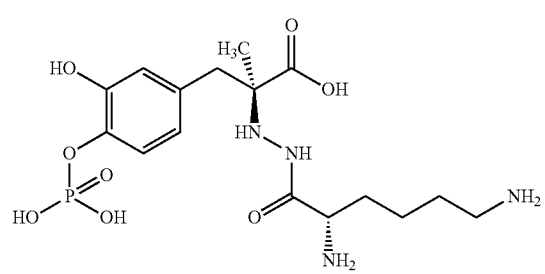 [SMILES: C[C@](Cc1ccc(OP(=O)(O)O)c(O)c1)(NNC(=O)[C@@H](N)CCCCN)C(=O)O]
MS (ESI); m/z 435.1 [M + H]+
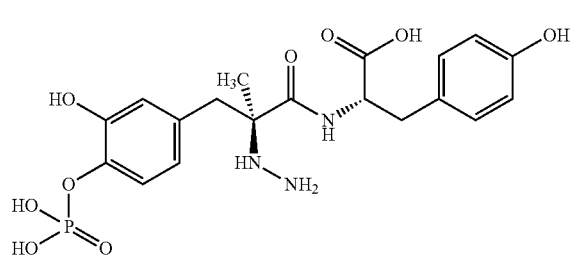 [SMILES: C[C@](Cc1ccc(OP(=O)(O)O)c(O)c1)(NN)C(=O)N[C@@H](Cc1ccc(O)cc1)C(=O)O]
MS (ESI); m/z 470.1 [M + H]+
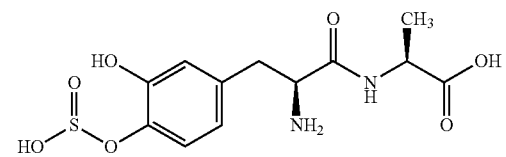 [SMILES: C[C@H](NC(=O)[C@@H](N)Cc1ccc(OS(=O)O)c(O)c1)C(=O)O]
—

TABLE C-continued
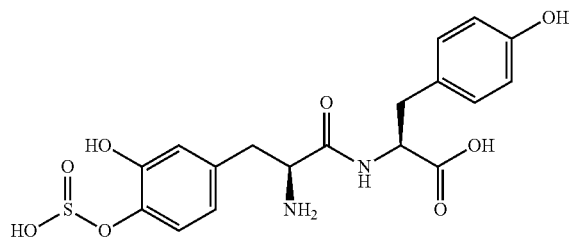 [SMILES: N[C@@H](Cc1ccc(OS(=O)O)c(O)c1)C(=O)N[C@@H](Cc1ccc(O)cc1)C(=O)O]
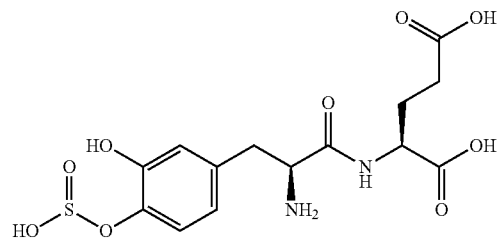 [SMILES: N[C@@H](Cc1ccc(OS(=O)O)c(O)c1)C(=O)N[C@@H](CCC(=O)O)C(=O)O]
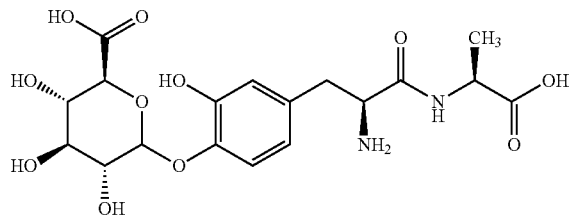 [SMILES: C[C@H](NC(=O)[C@@H](N)Cc1ccc(OC2O[C@H](C(=O)O)[C@@H](O)[C@H](O)[C@H]2O)c(O)c1)C(=O)O]
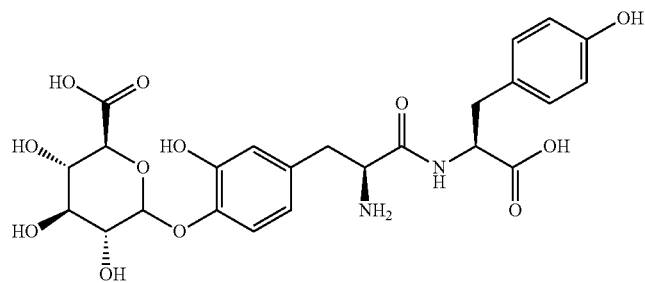 [SMILES: N[C@@H](Cc1ccc(OC2O[C@H](C(=O)O)[C@@H](O)[C@H](O)[C@H]2O)c(O)c1)C(=O)N[C@@H](Cc1ccc(O)cc1)C(=O)O]
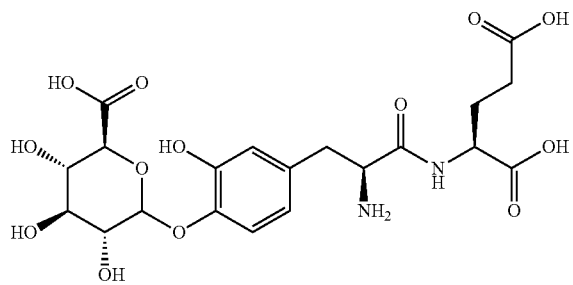 [SMILES: N[C@@H](Cc1ccc(OC2O[C@H](C(=O)O)[C@@H](O)[C@H](O)[C@H]2O)c(O)c1)C(=O)N[C@@H](CCC(=O)O)C(=O)O]
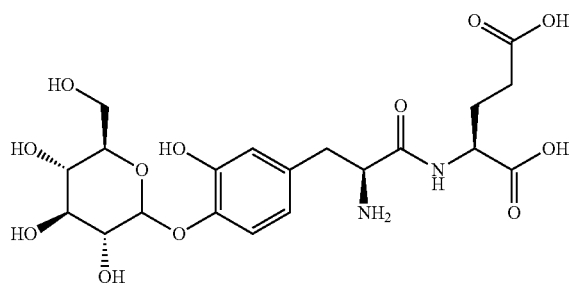 [SMILES: N[C@@H](Cc1ccc(OC2O[C@H](CO)[C@@H](O)[C@H](O)[C@H]2O)c(O)c1)C(=O)N[C@@H](CCC(=O)O)C(=O)O]

TABLE C-continued
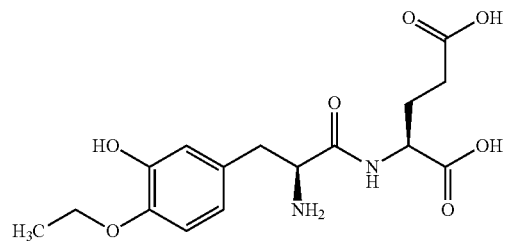 [SMILES: CCOc1ccc(C[C@H](N)C(=O)N[C@@H](CCC(=O)O)C(=O)O)cc1O] —
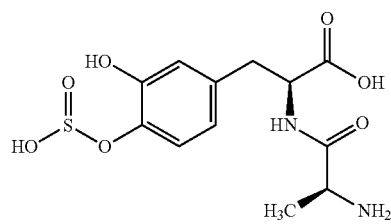 [SMILES: C[C@H](N)C(=O)N[C@@H](Cc1ccc(OS(=O)O)c(O)c1)C(=O)O] —
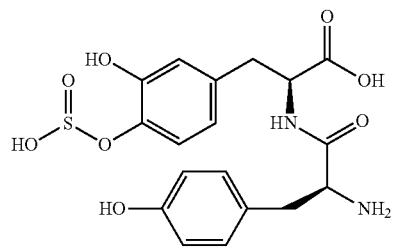 [SMILES: N[C@@H](Cc1ccc(O)cc1)C(=O)N[C@@H](Cc1ccc(OS(=O)O)c(O)c1)C(=O)O] —
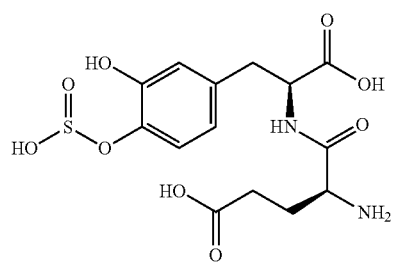 [SMILES: N[C@@H](CCC(=O)O)C(=O)N[C@@H](Cc1ccc(OS(=O)O)c(O)c1)C(=O)O] —
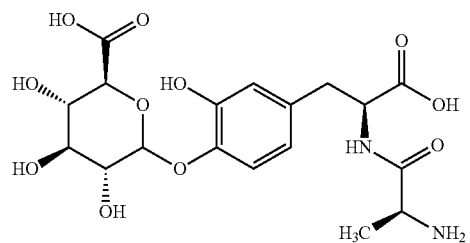 [SMILES: C[C@H](N)C(=O)N[C@@H](Cc1ccc(OC2O[C@H](C(=O)O)[C@@H](O)[C@H](O)[C@H]2O)c(O)c1)C(=O)O] —
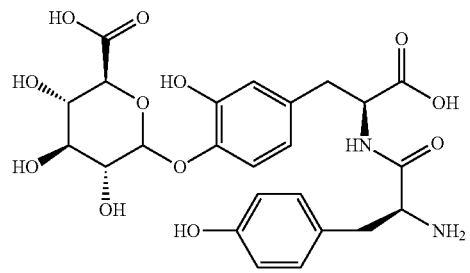 [SMILES: N[C@@H](Cc1ccc(O)cc1)C(=O)N[C@@H](Cc1ccc(OC2O[C@H](C(=O)O)[C@@H](O)[C@H](O)[C@H]2O)c(O)c1)C(=O)O] —

TABLE C-continued
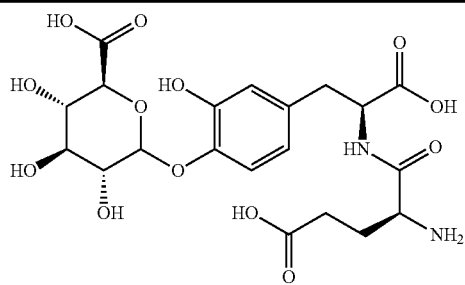
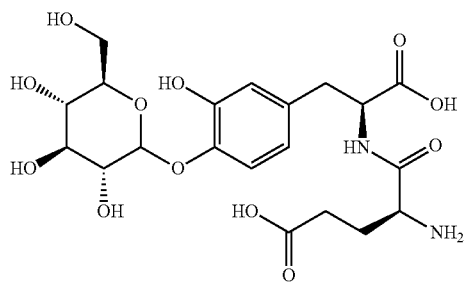 [SMILES: N[C@@H](CCC(=O)O)C(=O)N[C@@H](Cc1ccc(OC2O[C@H](CO)[C@@H](O)[C@H](O)[C@H]2O)c(O)c1)C(=O)O]
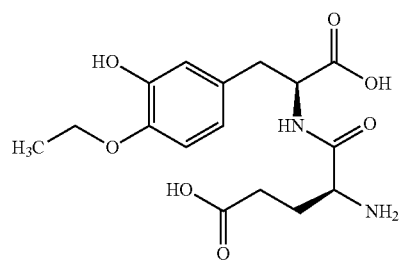 [SMILES: CCOc1ccc(C[C@H](NC(=O)[C@@H](N)CCC(=O)O)C(=O)O)cc1O]
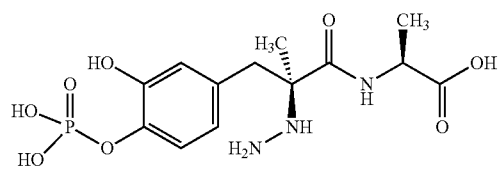 [SMILES: C[C@H](NC(=O)[C@@](C)(Cc1ccc(OP(=O)(O)O)c(O)c1)NN)C(=O)O]
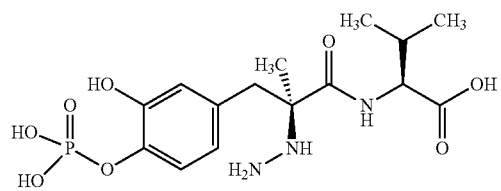 [SMILES: CC(C)[C@H](NC(=O)[C@@](C)(Cc1ccc(OP(=O)(O)O)c(O)c1)NN)C(=O)O]
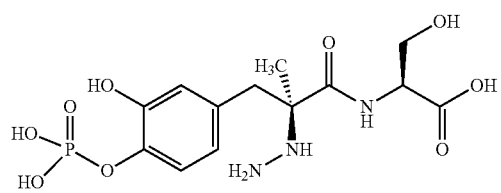 [SMILES: C[C@](Cc1ccc(OP(=O)(O)O)c(O)c1)(NN)C(=O)N[C@@H](CO)C(=O)O]
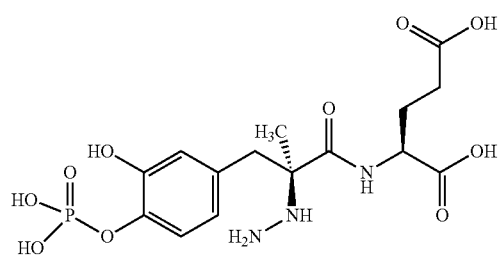 [SMILES: C[C@](Cc1ccc(OP(=O)(O)O)c(O)c1)(NN)C(=O)N[C@@H](CCC(=O)O)C(=O)O]

TABLE C-continued
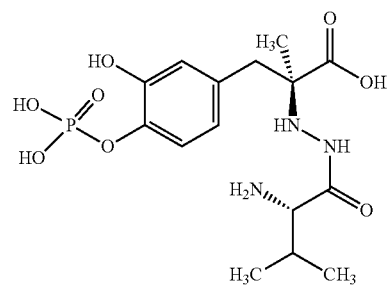 [SMILES: CC(C)[C@H](N)C(=O)NN[C@](C)(Cc1ccc(OP(=O)(O)O)c(O)c1)C(=O)O]
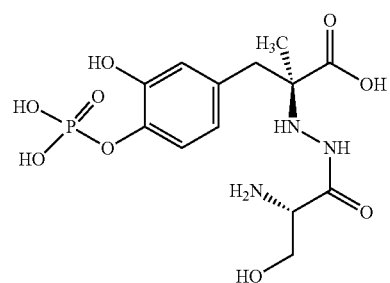 [SMILES: C[C@](Cc1ccc(OP(=O)(O)O)c(O)c1)(NNC(=O)[C@@H](N)CO)C(=O)O]
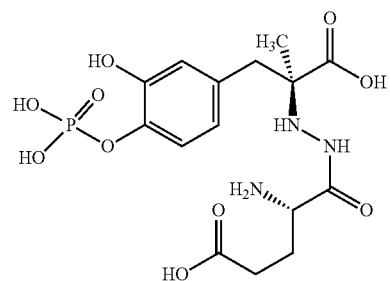 [SMILES: C[C@](Cc1ccc(OP(=O)(O)O)c(O)c1)(NNC(=O)[C@@H](N)CCC(=O)O)C(=O)O]
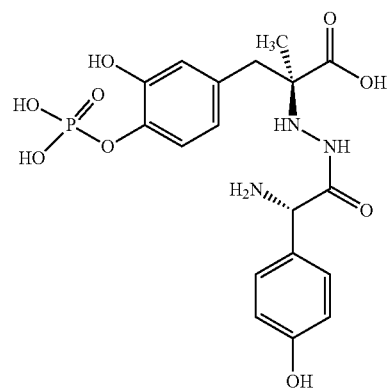 [SMILES: C[C@](Cc1ccc(OP(=O)(O)O)c(O)c1)(NNC(=O)[C@@H](N)c1ccc(O)cc1)C(=O)O]
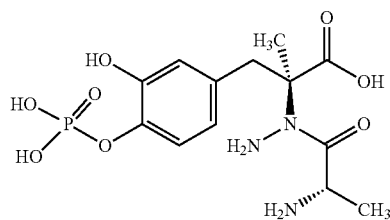 [SMILES: C[C@H](N)C(=O)N(N)[C@](C)(Cc1ccc(OP(=O)(O)O)c(O)c1)C(=O)O]

TABLE C-continued
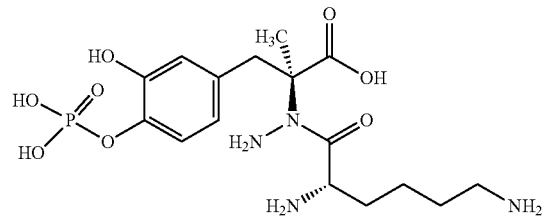 [SMILES: C[C@@](Cc1ccc(OP(=O)(O)O)c(O)c1)(C(=O)O)N(N)C(=O)[C@@H](N)CCCCN]
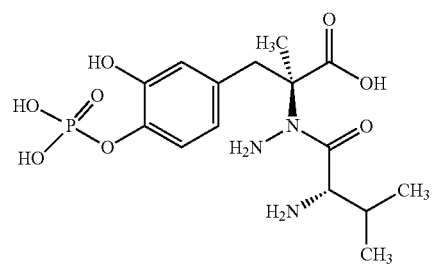 [SMILES: CC(C)[C@H](N)C(=O)N(N)[C@](C)(Cc1ccc(OP(=O)(O)O)c(O)c1)C(=O)O]
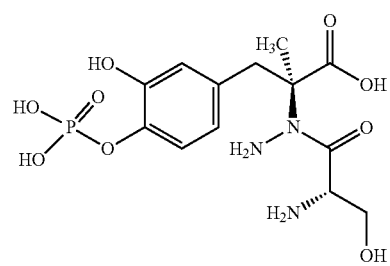 [SMILES: C[C@@](Cc1ccc(OP(=O)(O)O)c(O)c1)(C(=O)O)N(N)C(=O)[C@@H](N)CO]
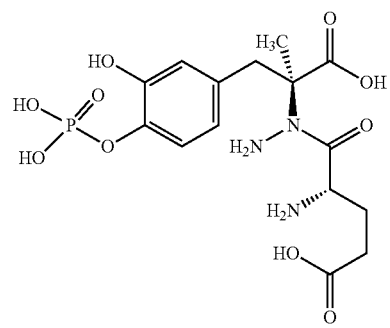 [SMILES: C[C@@](Cc1ccc(OP(=O)(O)O)c(O)c1)(C(=O)O)N(N)C(=O)[C@@H](N)CCC(=O)O]
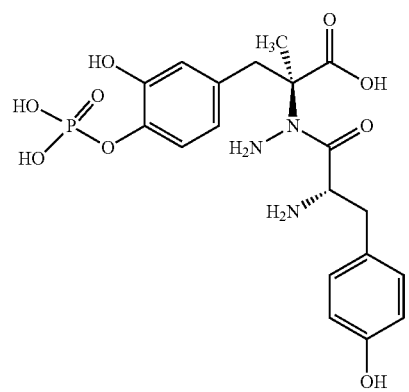 [SMILES: C[C@@](Cc1ccc(OP(=O)(O)O)c(O)c1)(C(=O)O)N(N)C(=O)[C@@H](N)Cc1ccc(O)cc1]

TABLE C-continued
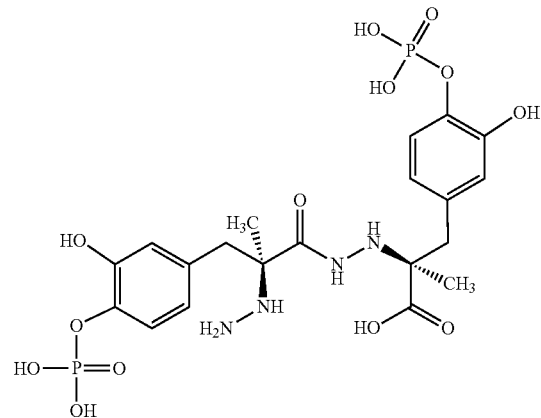
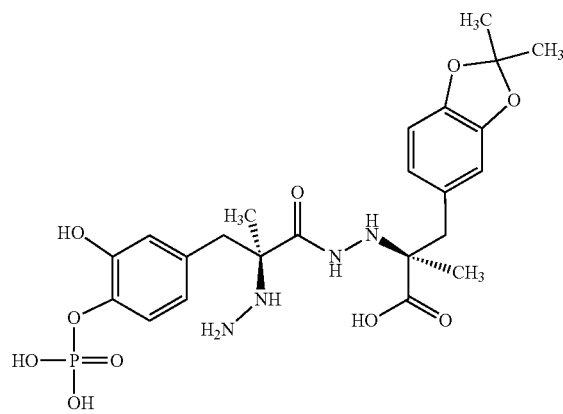
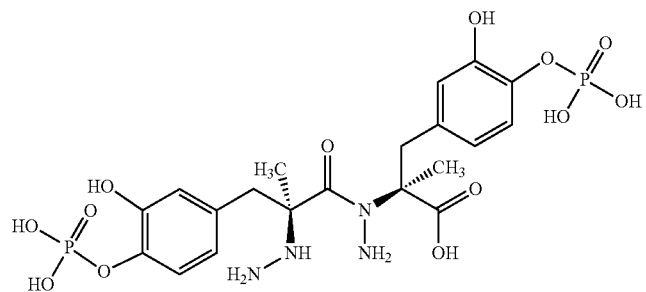
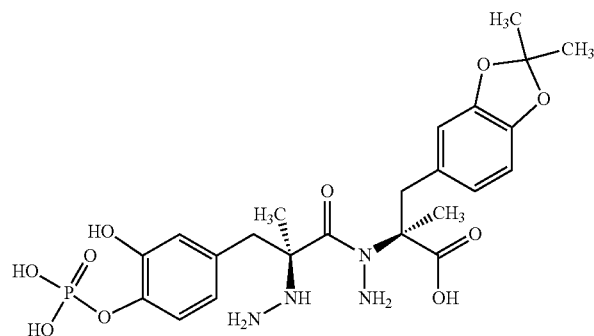

TABLE C-continued
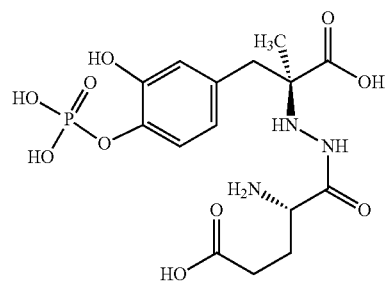 [SMILES: C[C@@](Cc1ccc(OP(=O)(O)O)c(O)c1)(NNC(=O)[C@@H](N)CCC(=O)O)C(=O)O]
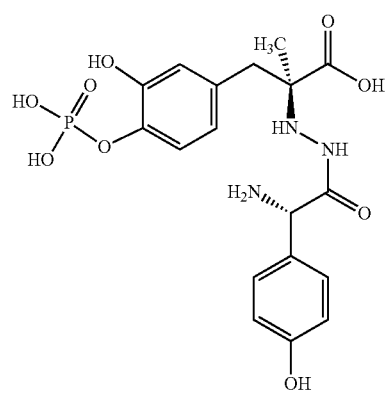 [SMILES: C[C@@](Cc1ccc(OP(=O)(O)O)c(O)c1)(NNC(=O)[C@@H](N)c1ccc(O)cc1)C(=O)O]
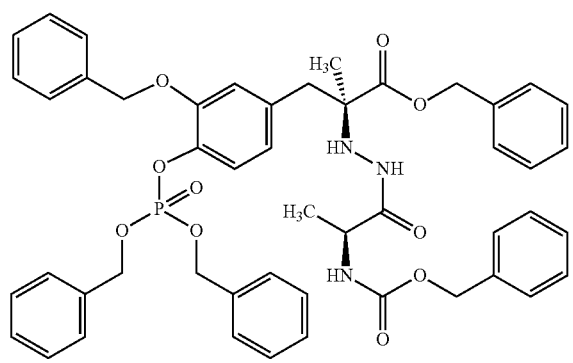 [SMILES: C[C@H](NC(=O)OCc1ccccc1)C(=O)NN[C@@](C)(Cc1ccc(OP(=O)(OCc2ccccc2)OCc2ccccc2)c(OCc2ccccc2)c1)C(=O)OCc1ccccc1]
MS (ESI); m/z 870.5 [M − H]−
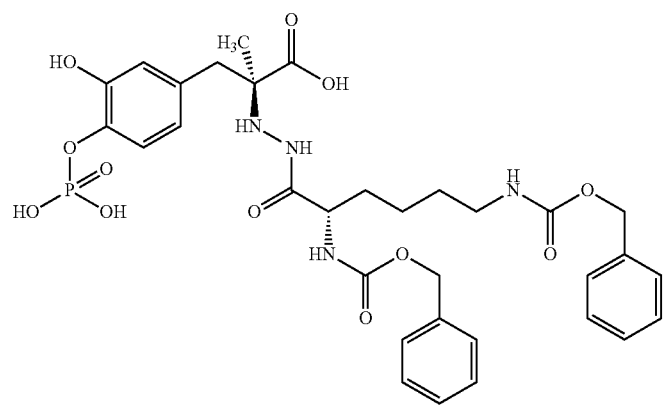 [SMILES: C[C@@](Cc1ccc(OP(=O)(O)O)c(O)c1)(NNC(=O)[C@H](CCCCNC(=O)OCc1ccccc1)NC(=O)OCc1ccccc1)C(=O)O]
MS (ESI); m/z 703.2 [M + H]+

TABLE C-continued
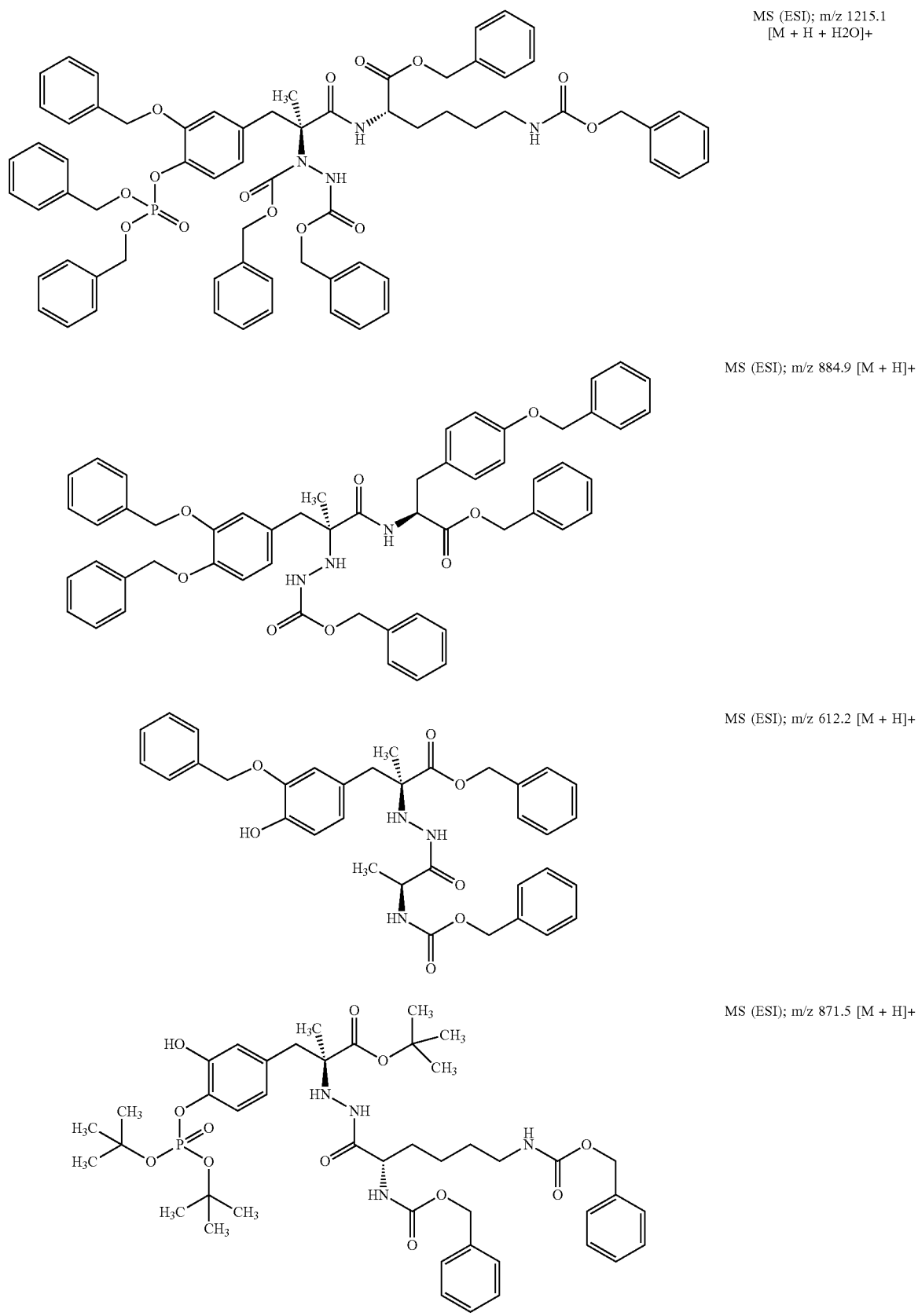
MS (ESI); m/z 1215.1 [M + H + H2O]+
MS (ESI); m/z 884.9 [M + H]+
MS (ESI); m/z 612.2 [M + H]+
MS (ESI); m/z 871.5 [M + H]+

According to some embodiments, the DDCI is carbidopa, a carbidopa prodrug, a carbidopa salt, benserazide, a benserazide prodrug, a benserazide salt, or any combination thereof. According to some embodiments, the DDCI is carbidopa. According to some embodiments, the DDCI is a carbidopa prodrug, e.g., selected from the carbidopa prodrugs disclosed herein. The DDCI in the first pharmaceutical composition may be the same or different as the DDCI in the second pharmaceutical composition. Further, the levodopa moiety in each of the first and second pharmaceutical compositions may be the same or different. That is, while according to some embodiments, both the first pharmaceutical composition and the second pharmaceutical composition comprise levodopa, according to other embodiments the first pharmaceutical composition may comprise one type of levodopa moiety, e.g., a levodopa prodrug and/or a levodopa salt, while the second pharmaceutical composition comprises a different type of levodopa moiety, e.g., levodopa. It is further noted that the concentration or amount of each moiety within the first pharmaceutical composition may be different than the concentration or amount of that moiety within the second pharmaceutical composition.

According to some embodiments, the carbidopa prodrug in the first pharmaceutical composition is selected from compounds of Formula (XV)

Formula (XV)

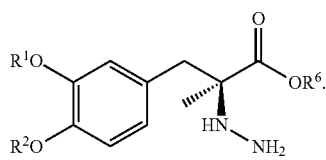

or a pharmaceutically acceptable salt thereof, wherein $R^1$ and $R^2$ are each independently selected from the group consisting of hydrogen, —P(O)(OH)$_2$ and —R$^5$—O—P(O)(OH)$_2$; $R^5$ is a $C_1$-$C_4$-alkyl; $R^6$ is hydrogen or a $C_1$-$C_4$-alkyl, and provided that at least one of $R^1$ and $R^2$ is —P(O)(OH)$_2$ or —R$^5$—O—P(O)(OH)$_2$.

According to some embodiments, the carbidopa prodrug included in the first pharmaceutical composition is a compound selected from any of the formulae below or pharmaceutically acceptable salts thereof:

Formula (XV-a)

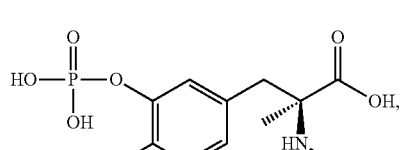

Formula (XV-b)

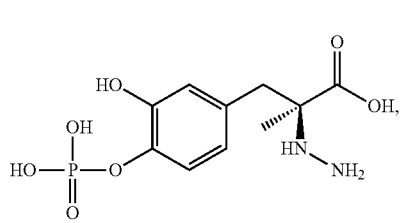

Formula (XV-c)

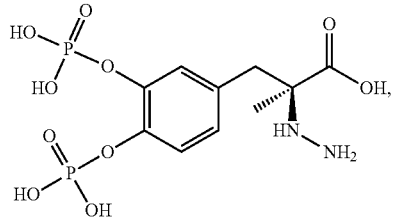

Formula (XV-d)

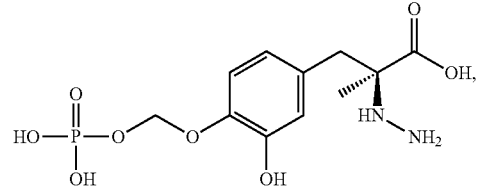

Formula (XV-e)

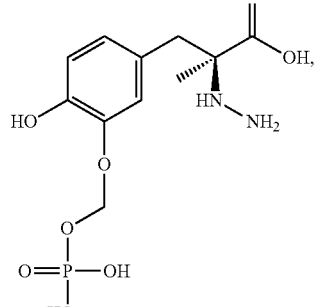

Formula (XV-f)

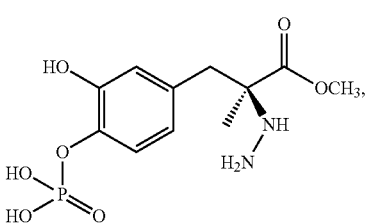

According to some embodiments, the levodopa prodrug included in the first pharmaceutical composition is selected from a compound of Formula (XVI):

Formula (XVI)

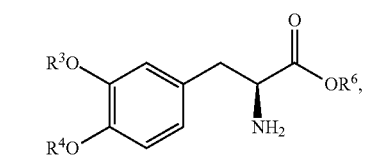

or a pharmaceutically acceptable salt thereof, wherein $R^3$ and $R^4$ are each independently selected from the group consisting of hydrogen, —P(O)(OH)$_2$ and —R$^5$—O—P(O)(OH)$_2$; $R^5$ is a $C_1$-$C_4$-alkyl; $R^6$ is hydrogen or a $C_1$-$C_4$-alkyl, and provided that at least one of $R^3$ and $R^4$ is —P(O)(OH)$_2$ or —R$^5$—O—P(O)(OH)$_2$.

According to some embodiments, the levodopa prodrug included in the first pharmaceutical composition is a compound selected from any of the formulae below or pharmaceutically acceptable salts thereof:

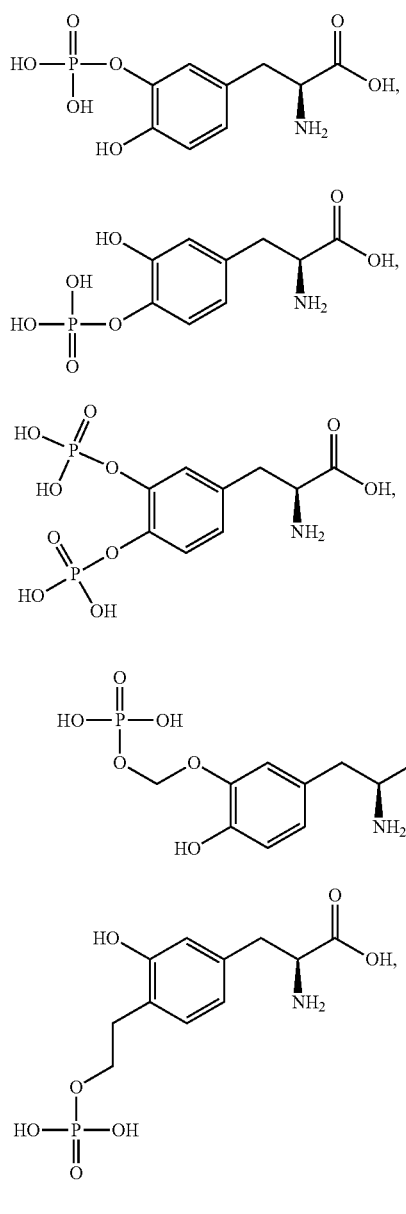

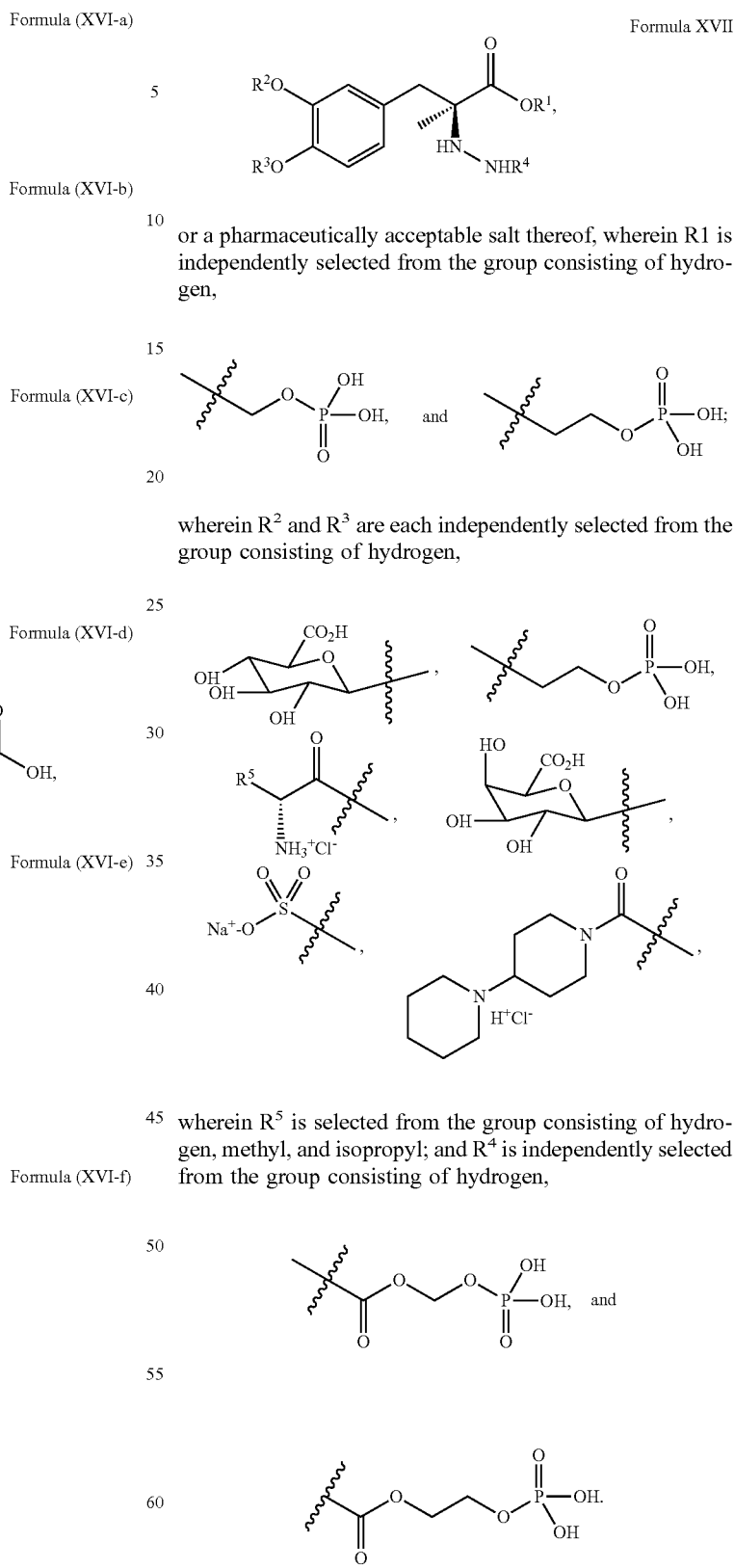

or a pharmaceutically acceptable salt thereof, wherein R1 is independently selected from the group consisting of hydrogen, wherein $R^2$ and $R^3$ are each independently selected from the group consisting of hydrogen, wherein $R^5$ is selected from the group consisting of hydrogen, methyl, and isopropyl; and $R^4$ is independently selected from the group consisting of hydrogen, According to some embodiments, the carbidopa prodrug in the first pharmaceutical composition is selected from compounds of Formula XVII:

According to some embodiments, the carbidopa prodrug included in the first pharmaceutical composition is a compound selected from any of the formulae below:

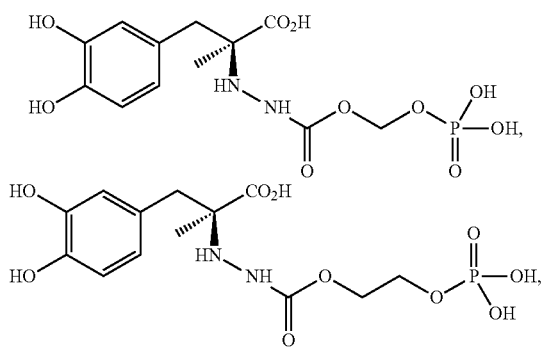

or a pharmaceutically acceptable salt thereof.

According to some embodiments, the levodopa prodrug in the first pharmaceutical composition is selected from compounds of Formula XVIII:

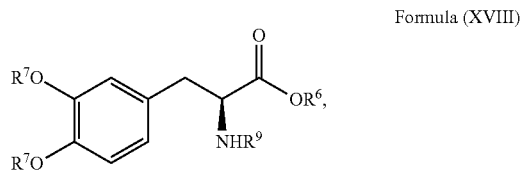

Formula (XVIII)

or a pharmaceutically acceptable salt thereof, wherein $R^6$ is independently selected from the group consisting of hydrogen,

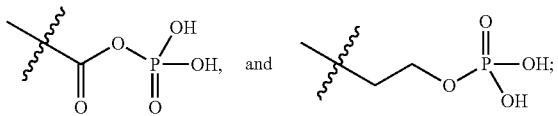 [SMILES: *C(=O)OP(=O)(O)O ; *CCOP(=O)(O)O]

$R^7$ and $R^8$ are each independently selected from the group consisting of hydrogen,

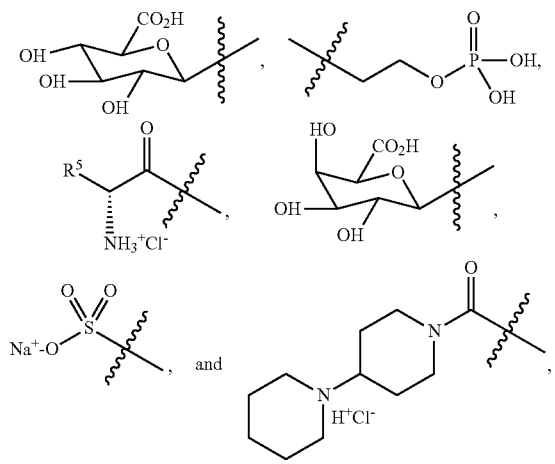

wherein $R^5$ is selected from the group consisting of hydrogen, methyl and isopropyl; and $R_9$ is independently selected from the group consisting of hydrogen,

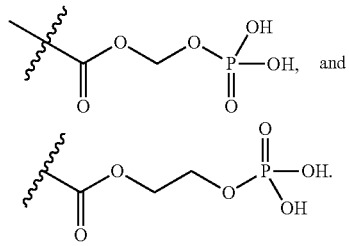

According to some embodiments, the levodopa prodrug included in the first pharmaceutical composition is a compound selected from any of the formulae below:

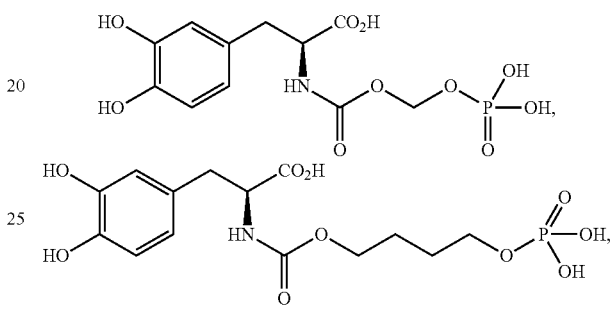

or a pharmaceutically acceptable salt thereof.

According to some embodiments the first pharmaceutical composition may be administered by any parenteral administration route, e.g., subcutaneously, transdermally, intradermally, intravenously, intramuscularly, intratracheally, intranasally, intrathecally, intragastrically or intraduodenally. According to some embodiments the first pharmaceutical composition is administered subcutaneously. According to some embodiments, the first pharmaceutical composition is liquid. According to some embodiments, the first pharmaceutical composition is aqueous.

According to some embodiments, the first pharmaceutical composition is administered substantially continuously. According to some embodiments, the first pharmaceutical composition is administered subcutaneously via a designated pump device.

Embodiments of a designated pump may be, for example, any of the pump embodiments disclosed in U.S. Pat. Nos. 10,603,430, 10,463,787, 10,463,572, US 2020/0093984 WO2019/008529, USD 887,577, USD 921,187, USD 921, 188, USD 865,665, USD 868,689, USD 921,189, USD 921,190, USD 935,478, US 2020/0368448, USD 29/779, 154, USD 29/779,153, USD 29/811,491, USD 29/842,699, USD 29/842,700, USD 29/842,701, USD 29/842,702, USD 29/842,703, USD 29/842,704, USD 29/846,963, 63/316, 641, 63/352,362 all of which are incorporated herein by reference in their entirety.

According to some embodiments, the method of the invention comprises administering the first pharmaceutical composition at one site, two sites, or three or more sites, wherein the position of the sites may be changed at any appropriate, possibly pre-determined, intervals. Once administered via a specific site, according to some embodiments, the administration via the same site, or the vicinity of that site, may be only after a, possibly predefined, period of time. According to some embodiments, the position of any one of the sites is changed after 12, 24, 36, 48, 60 or 72 hours. According to some embodiments, the position of any one of the sites is changed after up to 24, up to 48, or up to 72 hours. According to some embodiments, the position of the site is changed after 4, 5, 6 or 7 days. According to some embodiments, the position of the site is changed after two, three or four weeks. According to some embodiments, the position of the site is changed when required or desired, e.g., according to subjective data received from the patient and/or according to objective data received, e.g., from sensors located at, or in the vicinity of, the injection site(s).

According to some embodiments, each infusion site should be positioned at least 3 cm, 5 cm, 7 cm or 10 cm from the navel. According to some embodiments, any new infusion site selected should be distanced by at least 1 cm, 1.5 cm, 2 cm, 2.5 cm, 5 cm, 7.5 cm, or 10 cm from any previous site that was used in the past 5, 7, 10, 12, 15 or 20 days.

According to some embodiments, the administrated volume and/or the administration rate is identical in all or at least two of the sites. According to other embodiments, the administration rate and/or administrated volume differ from site to site. Each site may be controlled independently or otherwise, all sites may be controlled dependently on one another.

According to some embodiments, the method of the invention comprises subcutaneously administering the first pharmaceutical composition of the invention over the course of about 5 to about 24 hours or more, for example, from about 5 to about 12 hours or more, from about 7 to about 10 hours or more, or for example, about 8 hours or about 24 hours.

According to some embodiments, the dose of the carbidopa moiety in the first pharmaceutical composition is between about 10 mg and about 25 mg per administration, between about 10 mg and about 50 mg per administration, between about 10 mg and about 75 mg per administration, between about 12 mg and about 25 mg per administration, between about 12 mg and about 50 mg per administration, between about 12 mg and about 75 mg per administration, between about 15 mg and about 25 mg per administration, between about 15 mg and about 50 mg per administration, between about 15 mg and about 75 mg per administration, between about 25 mg and about 50 mg per administration, between about 25 mg and about 75 mg per administration, between about 50 mg and about 75 mg per administration, between about 75 mg and about 100 mg per administration, between about 100 mg and about 125 mg per administration, between about 125 mg and about 150 mg per administration, or between about 150 mg and about 175 mg per administration. According to some embodiments, the dose of the carbidopa moiety in the first pharmaceutical composition is about 90 mg, for example, administered over the course of about 5 to about 24 hours or more. According to some embodiments, the dose of the carbidopa moiety in the first pharmaceutical composition is between about 46 mg and about 90 mg per administration. According to some embodiments, the dose of the carbidopa moiety in the first pharmaceutical composition is about 90 mg, for example, administered over the course of about 24 hours. According to some embodiments, the dose of the carbidopa moiety in the first pharmaceutical composition is between about 46 mg to about 90 mg, for example, administered over the course of about 24 hours. According to some embodiments, the dose of the carbidopa moiety in the first pharmaceutical composition is about 24 mg to 28 mg, for example, administered over the course of about 7 to about 10 hours or more. According to some embodiments, the dose of the carbidopa moiety in the first pharmaceutical composition is about 78 mg, for example, administered over the course of about 24 hours. According to some embodiments, the dose of the carbidopa moiety in the first pharmaceutical composition is about 117 mg, for example, administered over the course of about 24 hours. According to some embodiments, the dose of the carbidopa moiety in the first pharmaceutical composition is about 130 mg, for example, administered over the course of about 24 hours. According to some embodiments, the dose of the carbidopa moiety in the first pharmaceutical composition is about 143 mg, for example, administered over the course of about 24 hours. According to some embodiments, the dose of the carbidopa moiety in the first pharmaceutical composition is about 156 mg, for example, administered over the course of about 24 hours. According to some embodiments, the dose of the carbidopa moiety in the first pharmaceutical composition is about 225 mg, for example, administered over the course of about 24 hours.

According to some embodiments, the dose of the levodopa moiety in the first pharmaceutical composition is between about 1000 mg and 4000 mg per administration, between about 10 mg and about 800 mg per administration, between about 10 mg and about 25 mg per administration, between about 25 mg and about 50 mg per administration, between about 50 mg and about 75 mg per administration, between about 75 mg and about 100 mg per administration, between about 100 mg and about 150 mg per administration, between about 150 mg and about 200 mg per administration, between about 200 mg and about 250 mg per administration, between about 250 mg and about 300 mg per administration, between about 300 mg and about 350 mg per administration, between about 350 mg and about 400 mg per administration, between about 400 mg and about 450 mg per administration, between about 450 mg and about 500 mg per administration, between about 500 mg and 800 mg per administration, between about 600 mg and about 800 mg per administration, between about 700 mg and about 800 mg per administration, or about 720 mg per administration. In certain embodiments, the dose of the levodopa moiety in the first pharmaceutical composition is between about 370 mg to about 720 mg. In certain embodiments, the dose is administered over the course of about 5 to about 24 (e.g., about 7 to about 10, or about 8 hours, or about 24 hours) hours or more. According to some embodiments, the dose of the levodopa moiety in the first pharmaceutical composition is about 720 mg, for example, administered over the course of about 24 hours. According to some embodiments, the dose of the levodopa moiety in the first pharmaceutical composition is between about 370 mg about 720 mg, for example, administered over the course of about 24 hours. According to some embodiments, the dose of the levodopa moiety in the first pharmaceutical composition is between about 360 mg about 720 mg, for example, administered over the course of about 24 hours. According to some embodiments, the dose of the levodopa moiety in the first pharmaceutical composition is about 720 mg at the most. According to some embodiments, the dose of the levodopa moiety in the first pharmaceutical composition is between about 550 mg to about 650 mg, for example, administered over the course of about 7 to about 10 hours or more. According to some embodiments, the dose of the levodopa moiety in the first pharmaceutical composition is about 1800 mg, for example, administered over the course of about 24 hours. According to some embodiments, the dose of the levodopa moiety in the first pharmaceutical composition is about 2700 mg, for example, administered over the course of about 24 hours. According to some embodiments, the dose of the levodopa moiety in the first pharmaceutical composition is about 3000 mg, for example, administered over the course of about 24 hours. According to some embodiments, the dose of the levodopa moiety in the first pharmaceutical composition is about 3300 mg, for example, administered over the course of about 24 hours. According to some embodiments, the dose of the levodopa moiety in the first pharmaceutical composition is about 3600 mg, for example, administered over the course of about 24 hours. According to some embodiments, the dose of the levodopa moiety in the first pharmaceutical composition is such that about 4260 mg, for example, of levodopa are delivered over the course of about 24 hours.

In certain embodiments, the first pharmaceutical composition is administered in an amount to deliver up to about 4260 mg of levodopa and up to about 220 mg-227 mg of carbidopa to the patient over the course of about 24 hours. For example, the carbidopa or carbidopa prodrug is present in an amount to deliver up to about 220 mg-227 mg, about 220 mg-226 mg, about 220 mg-225 mg, about 220 mg-224 mg, about 220 mg-223 mg, about 220 mg-222 mg, about 221 mg-227 mg, about 221 mg-226 mg, about 221 mg-225 mg, about 221 mg-224 mg, about 221 mg-223 mg, about 221 mg-222 mg, about 222 mg-227 mg, about 222 mg-226 mg, about 222 mg-225 mg, about 222 mg-224 mg, about 222 mg-223 mg, about 223 mg-227 mg, about 223 mg-226 mg, about 223 mg-225, about 223 mg-224 of carbidopa to the patient. In certain embodiments, the first pharmaceutical composition is administered in an amount to deliver from about 500 to about 700 mg of levodopa and about 12 to about 50 mg of carbidopa to the patient. In certain embodiments, the first pharmaceutical composition is administered in an amount to deliver from about 550 to about 650 mg of levodopa and about 24 to about 28 mg of carbidopa to the patient. In certain embodiments, the first pharmaceutical composition is administered in an amount to deliver from about 100 to about 200 mg of levodopa and about 12 to about 50 mg of carbidopa to the patient. In certain embodiments, the first pharmaceutical composition is administered in an amount to deliver from about 140 to about 170 mg of levodopa and about 16 to about 24 mg of carbidopa to the patient. In certain embodiments, the dose is administered over the course of about 5 to about 24 (e.g., about 7 to about 10) hours or more. In certain embodiments, the first pharmaceutical composition is administered in an amount to deliver from about 650 mg to about 800 mg, e.g., about 720 mg of levodopa and about 80 mg to about 100 mg, e.g., about 90 mg, carbidopa to the patient over the course of about 24 hours. According to some embodiments, the dose of the carbidopa moiety in the first pharmaceutical composition is between about 46 mg about 90 mg, for example, administered over the course of about 24 hours. According to some embodiments, the dose of the carbidopa moiety in the first pharmaceutical composition is between about 45 mg about 90 mg, for example, administered over the course of about 24 hours. According to some embodiments, the dose of the carbidopa moiety in the first pharmaceutical composition is about 90 mg at the most. According to some embodiments, the dose of the carbidopa moiety in the first pharmaceutical composition is about 24 mg to 28 mg, for example, administered over the course of about 7 to about 10 hours or more. According to some embodiments, the dose of the carbidopa moiety in the first pharmaceutical composition is about 78 mg, for example, administered over the course of about 24 hours. According to some embodiments, the dose of the carbidopa moiety in the first pharmaceutical composition is about 117 mg, for example, administered over the course of about 24 hours. According to some embodiments, the dose of the carbidopa moiety in the first pharmaceutical composition is about 130 mg, for example, administered over the course of about 24 hours. According to some embodiments, the dose of the carbidopa moiety in the first pharmaceutical composition is about 143 mg, for example, administered over the course of about 24 hours. According to some embodiments, the dose of the carbidopa moiety in the first pharmaceutical composition is about 156 mg, for example, administered over the course of about 24 hours.

According to some embodiments, the first pharmaceutical composition comprises levodopa and carbidopa in a ratio of about 8:1 w/w. According to some embodiments, the first pharmaceutical composition is administered in an amount to deliver about 720 mg LD and about 90 mg CD per day, about 360 mg LD and about 45 mg CD per day, about 370 mg LD and about 46 mg CD per day, wherein the levodopa and carbidopa are in a ratio of about 8:1 w/w.

According to some embodiments, the first pharmaceutical composition is administered in an amount to deliver more than 0 mg and up to about 720 mg LD and more than 0 mg and up to about 90 mg CD per day, wherein the ratio of LD/CD administered is about 8:1 w/w. According to some embodiments, the first pharmaceutical composition is administered in an amount to deliver between about 8 mg to about 720 mg LD and about 1 mg to about 90 mg CD per day, at a ratio of about 8:1 w/w LD/CD. According to some embodiments, the first pharmaceutical composition is administered in an amount to deliver between about 360 mg to about 720 mg LD and about 45 mg to about 90 mg CD per day, at a ratio of about 8:1 w/w LD/CD. According to some embodiments, the first pharmaceutical composition is administered in an amount to deliver between about 370 mg to about 720 mg LD and about 46 mg to about 90 mg CD per day, at a ratio of about 8:1 w/w LD/CD. According to some embodiments, the first pharmaceutical composition is administered in an amount to deliver between about 370 mg to about 720 mg LD and about 46 mg to about 90 mg CD per day, at a ratio of about 8:1 w/w LD/CD.

According to some embodiments, the first pharmaceutical composition comprises up to about 60 mg/ml levodopa. According to some embodiments, the first pharmaceutical composition comprises up to about 7.5 mg/ml carbidopa. According to some embodiments, the first pharmaceutical composition comprises up to about 60 mg/ml levodopa and up to about 7.5 mg/ml carbidopa, wherein the levodopa and carbidopa and in a ratio of about 8:1 w/w.

According to some embodiments, the first pharmaceutical composition is administered in an amount to deliver more than 0 mg and up to about 2700 mg LD-Tyr and more than 0 mg and up to about 117 mg carbidopa per day, wherein the ratio of LD-Tyr/CD administered is about 23:1 w/w. According to some embodiments, the first pharmaceutical composition is administered in an amount to deliver more than 0 mg and up to about 3000 mg LD-Tyr and more than 0 mg and up to about 117 mg carbidopa per day, wherein the ratio of LD-Tyr/CD administered is about 26:1 w/w. According to some embodiments, the first pharmaceutical composition is administered in an amount to deliver more than 0 mg and up to about 3300 mg LD-Tyr and more than 0 mg and up to about 117 mg carbidopa per day, wherein the ratio of LD-Tyr/CD administered is about 28:1 w/w. According to some embodiments, the first pharmaceutical composition is administered in an amount to deliver more than 0 mg and up to about 3600 mg LD-Tyr and more than 0 mg and up to about 117 mg carbidopa per day, wherein the ratio of LD-Tyr/CD administered is about 31:1 w/w. According to some embodiments, the first pharmaceutical composition is administered in an amount to deliver more than 0 mg and up to about 2400 mg LD-Tyr and more than 0 mg and up to about 117 mg carbidopa per day, wherein the ratio of LD-Tyr/CD administered is about 21:1 w/w. According to some embodiments, the first pharmaceutical composition is administered in an amount to deliver more than 0 mg and up to about 2700 mg LD-Tyr and more than 0 mg and up to about 90 mg carbidopa per day, wherein the ratio of LD-Tyr/CD administered is about 30:1 w/w. According to some embodiments, the first pharmaceutical composition is administered in an amount to deliver more than 0 mg and up to about 3000 mg LD-Tyr and more than 0 mg and up to about 90 mg carbidopa per day, wherein the ratio of LD-Tyr/CD administered is about 33:1 w/w. According to some embodiments, the first pharmaceutical composition is administered in an amount to deliver more than 0 mg and up to about 3300 mg LD-Tyr and more than 0 mg and up to about 90 mg carbidopa per day, wherein the ratio of LD-Tyr/CD administered is about 37:1 w/w. According to some embodiments, the first pharmaceutical composition is administered in an amount to deliver more than 0 mg and up to about 3600 mg LD-Tyr and more than 0 mg and up to about 90 mg carbidopa per day, wherein the ratio of LD-Tyr/CD administered is about 40:1 w/w. According to some embodiments, the first pharmaceutical composition is administered in an amount to deliver more than 0 mg and up to about 2400 mg LD-Tyr and more than 0 mg and up to about 90 mg carbidopa per day, wherein the ratio of LD-Tyr/CD administered is about 27:1 w/w. According to some embodiments, the first pharmaceutical composition is administered in an amount to deliver more than 0 mg and up to about 2700 mg LD-Tyr and more than 0 mg and up to about 75 mg carbidopa per day, wherein the ratio of LD-Tyr/CD administered is about 36:1 w/w. According to some embodiments, the first pharmaceutical composition is administered in an amount to deliver more than 0 mg and up to about 3000 mg LD-Tyr and more than 0 mg and up to about 75 mg carbidopa per day, wherein the ratio of LD-Tyr/CD administered is about 40:1 w/w. According to some embodiments, the first pharmaceutical composition is administered in an amount to deliver more than 0 mg and up to about 3300 mg LD-Tyr and more than 0 mg and up to about 75 mg carbidopa per day, wherein the ratio of LD-Tyr/CD administered is about 44:1 w/w. According to some embodiments, the first pharmaceutical composition is administered in an amount to deliver more than 0 mg and up to about 3600 mg LD-Tyr and more than 0 mg and up to about 75 mg carbidopa per day, wherein the ratio of LD-Tyr/CD administered is about 48:1 w/w. According to some embodiments, the first pharmaceutical composition is administered in an amount to deliver more than 0 mg and up to about 2400 mg LD-Tyr and more than 0 mg and up to about 75 mg carbidopa per day, wherein the ratio of LD-Tyr/CD administered is about 32:1 w/w.

According to some embodiments, the first pharmaceutical composition comprises about 300 mg/ml LD-Tyr. According to some embodiments, the first pharmaceutical composition comprises about 13 mg/ml carbidopa. According to some embodiments, the first pharmaceutical composition comprises up to about 300 mg/ml levodopa and up to about 13 mg carbidopa, wherein the levodopa and carbidopa are in a ratio of about 23:1 w/w. According to some embodiments, the first pharmaceutical composition comprises about 300 mg/ml LD-Tyr. According to some embodiments, the first pharmaceutical composition comprises about 10 mg/ml carbidopa. According to some embodiments, the first pharmaceutical composition comprises up to about 300 mg/ml levodopa and up to about 10 mg carbidopa, wherein the levodopa and carbidopa are in a ratio of about 30:1 w/w.

According to some embodiments, the first pharmaceutical composition comprises up to about 720 mg levodopa. According to some embodiments, the first pharmaceutical composition comprises up to about 90 mg carbidopa. According to some embodiments, the first pharmaceutical composition comprises up to about 720 mg levodopa and up to about 90 mg carbidopa, wherein the levodopa and carbidopa and in a ratio of about 8:1 w/w.

According to some embodiments, the first pharmaceutical composition is administered in an amount to deliver about 720 mg, about 660-670 mg, about 620-630 mg, about 560-570 mg, about 510-520 mg, about 470-480 mg, about 410-420 mg, or about 370-380 mg of levodopa per day. According to some embodiments, the first pharmaceutical composition is administered in an amount to deliver about 90 mg, about 85-90 about 80-85 mg, about 75-80 mg, about 70-75 mg, about 65-70 mg, about 60-65, about 55-60 mg, about 50-55 mg, or about 45-50 mg of carbidopa per day. According to some embodiments, the first pharmaceutical composition is administered in an amount to deliver about 720 mg levodopa and about 90 mg carbidopa, about 660-670 mg levodopa and about 80-85 mg carbidopa, about 610-620 mg levodopa and about 75-80 mg carbidopa, about 560-570 mg levodopa and about 70-75 mg carbidopa, about 510-520 mg levodopa and about 60-70 mg carbidopa, about 470-480 mg levodopa and about 55-60 mg carbidopa, about 410-420 mg levodopa and about 50-55 mg carbidopa, or about 370-380 mg of levodopa and about 45-50 mg carbidopa per day, wherein the levodopa and carbidopa are administered at a ratio of about 8:1 w/w.

According to some embodiments, the first pharmaceutical composition comprises a levodopa moiety and a carbidopa moiety in a ratio of between about 2:1 w/w to about 40:1 w/w. According to some embodiments, the first pharmaceutical composition comprises a levodopa moiety and a carbidopa moiety in a ratio of between about 2:1 w/w to about 4:1 w/w. According to some embodiments, the first pharmaceutical composition comprises a levodopa moiety and a carbidopa moiety in a ratio of between about 4:1 w/w to about 6:1 w/w. According to some embodiments, the first pharmaceutical composition comprises a levodopa moiety and a carbidopa moiety in a ratio of between about 6:1 w/w to about 8:1 w/w. According to some embodiments, the first pharmaceutical composition comprises a levodopa moiety and a carbidopa moiety in a ratio of between about 8:1 w/w to about 10:1 w/w. According to some embodiments, the first pharmaceutical composition comprises a levodopa moiety and a carbidopa moiety in a ratio of between about 10:1 w/w to about 15:1 w/w. According to some embodiments, the first pharmaceutical composition comprises a levodopa moiety and a carbidopa moiety in a ratio of between about 15:1 w/w to about 20:1 w/w. According to some embodiments, the first pharmaceutical composition comprises a levodopa moiety and a carbidopa moiety in a ratio of between about 20:1 w/w to about 25:1 w/w. According to some embodiments, the first pharmaceutical composition comprises a levodopa moiety and a carbidopa moiety in a ratio of between about 25:1 w/w to about 30:1 w/w. According to some embodiments, the first pharmaceutical composition comprises a levodopa moiety and a carbidopa moiety in a ratio of between about 30:1 w/w to about 35:1 w/w. According to some embodiments, the first pharmaceutical composition comprises a levodopa moiety and a carbidopa moiety in a ratio of between about 35:1 w/w to about 40:1 w/w. According to some embodiments, the first pharmaceutical composition comprises a levodopa moiety and a carbidopa moiety in a ratio of about 20:1 w/w.

According to some embodiments, the first pharmaceutical composition is administered in an amount to deliver about 100 mg, about 200 mg, about 240 mg, about 480 mg, about 720 mg, about 960 mg, about 1200 mg, about 1440 mg, about 1680 mg, about 1920 mg, about 2160 mg, about 2400 mg, about 2640 mg, about 2880 mg, about 3120 mg, about 3360 mg, about 3600 mg, about 3840 mg, about 4080 mg, about 4320 mg, about 4560 mg, about 4800 mg, about 5040 mg, about 5280 mg, about 5520 mg, about 5760 mg, about 6000 mg, of a levodopa moiety over the course of about 24 hours. According to some embodiment the first pharmaceutical composition is administered in an amount to deliver between about 100 mg to about 6000 mg of a levodopa moiety over the course of about 24 hours. According to some embodiment the first pharmaceutical composition is administered in an amount to deliver between about 240 mg to about 4800 mg of a levodopa moiety over the course of about 24 hours. According to some embodiment the first pharmaceutical composition is administered in an amount to deliver between about 8 mg to about 1600 mg of a levodopa moiety over the course of about 24 hours. According to some embodiment the first pharmaceutical composition is administered in an amount to deliver between about 8 mg to about 3200 mg of a levodopa moiety over the course of about 24 hours. According to some embodiment the first pharmaceutical composition is administered in an amount to deliver between about 8 mg to about 3440 mg of a levodopa moiety over the course of about 24 hours.

According to some embodiments, the first pharmaceutical composition is administered in an amount to deliver about 5 mg, about 6 mg, about 10 mg, about 12 mg, about 24 mg, about 36 mg, about 48 mg, about 60 mg, about 72 mg, about 84 mg, about 96 mg, about 108 mg, about 120 mg, about 132 mg, about 144 mg, about 156 mg, about 168 mg, about 180 mg, about 192 mg, about 204 mg, about 216 mg, about 228 mg, about 240 mg, about 252 mg, about 264 mg, about 276 mg, about 288 mg, or about 300 mg of a carbidopa moiety over the course of about 24 hours. According to some embodiments, the first pharmaceutical composition is administered in an amount to deliver between about 12 mg to about 240 mg of a carbidopa moiety over the course of about 24 hours. According to some embodiments, the first pharmaceutical composition is administered in an amount to deliver between about 1 mg to about 300 mg of a carbidopa moiety over the course of about 24 hours.

According to some embodiment the first pharmaceutical composition is administered in an amount to deliver between about 240 mg to about 4800 mg of a levodopa moiety and between about 12 mg to about 240 mg of a carbidopa moiety over the course of about 24 hours.

According to some embodiments, the method of the invention comprises subcutaneously administering between about 1 to about 30 ml of the first pharmaceutical composition of the invention over the course of 24 hours. According to some embodiments, the method of the invention comprises subcutaneously administering between about 1 to about 120 ml of the first pharmaceutical composition of the invention over the course of 24 hours. According to some embodiments, the method of invention comprises subcutaneously administering between about 1 ml to about 2 ml, between about 2 ml to about 3 ml, between about 3 ml to about 4 ml, between about 4 ml to about 5 ml, between about 5 ml to about 6 ml, between about 6 ml to about 7 ml, between about 7 ml to about 8 ml, between about 8 ml to about 9 ml, between about 9 ml to about 10 ml, between about 10 ml to about 11 ml, between about 11 ml to about 12 ml, between about 12 ml to about 13 ml, between about 13 ml to about 14 ml, between about 14 ml to about 15 ml between about 15 ml to about 16 ml, between about 16 ml to about 17 ml, between about 17 ml to about 18 ml, between about 18 ml to about 19 ml, between about 19 ml to about 20 ml, between about 20 ml to about 21 ml, between about 21 ml to about 22 ml, between about 22 ml to about 23 ml, between about 23 ml to about 24 ml, between about 24 ml to about 25 ml, between about 25 ml to about 26 ml, between about 26 ml to about 27 ml, between about 27 ml to about 28 ml, between about 28 ml to about 29 ml, between about 29 ml to about 30 ml, between about 30 ml to about 40 ml, between about 40 ml to about 50 ml, between about 50 ml to about 60 ml, between about 60 ml to about 70 ml, between about 70 ml to about 80 ml, between about 80 ml to about 90 ml, between about 90 ml to about 100 ml, between about 100 ml to about 110 ml, between about 110 ml to about 120 ml, of the first pharmaceutical composition over the course of 24 hours. According to some embodiments, the method of the invention comprises subcutaneously administering about 9 ml of the first pharmaceutical composition of the invention over the course of about 24 hours. According to some embodiments, the method of the invention comprises subcutaneously administering about 10 ml of the first pharmaceutical composition of the invention over the course of about 24 hours. According to some embodiments, the method of the invention comprises subcutaneously administering about 11 ml of the first pharmaceutical composition of the invention over the course of about 24 hours. According to some embodiments, the method of the invention comprises subcutaneously administering about 12 ml of the first pharmaceutical composition of the invention over the course of about 24 hours. According to some embodiments, the method of the invention comprises subcutaneously administering about 20 ml of the first pharmaceutical composition of the invention over the course of about 24 hours. According to some embodiments, the method of the invention comprises subcutaneously administering up to about 12 ml of the first pharmaceutical composition of the invention over the course of about 24 hours. According to some embodiments, the method of the invention comprises subcutaneously administering up to about 20 ml of the first pharmaceutical composition of the invention over the course of about 24 hours. According to some embodiments, the method of the invention comprises subcutaneously administering up to about 9 ml of the first pharmaceutical composition of the invention over the course of about 24 hours. According to some embodiments, the method of the invention comprises subcutaneously administering up to about 10 ml of the first pharmaceutical composition of the invention over the course of about 24 hours. According to some embodiments, the method of the invention comprises subcutaneously administering up to about 11 ml of the first pharmaceutical composition of the invention over the course of about 24 hours. According to some embodiments, the method of the invention comprises subcutaneously administering up to about 120 ml of the first pharmaceutical composition of the invention over the course of about 24 hours.

According to some embodiments, the first pharmaceutical composition is administered at a volume of between about 1 ml to about 30 ml per site per day, between about 2 ml to about 20 ml per site per day, between about 3 ml to about 10 ml per site per day, between about 5 ml to about 7 ml per site per day, or about 6 ml per site per day. According to some embodiments, the first pharmaceutical composition is administered at a volume of between about 1 ml to about 2.5 ml per site per day, between about 2.5 ml to about 5.0 ml per site per day, between about 5.0 ml to about 7.5 ml per site per day, between about 7.5 ml to about 10 ml per site per day, between about 10 ml to about 12.5 ml per site per day, between about 12.5 ml to about 15 ml per site per day, between about 15 ml to about 17.5 ml per site per day, between about 17.5 ml to about 20 ml per site per day, between about 20 ml to about 22.5 ml per site per day, between about 22.5 ml to about 25 ml per site per day, between about 25 ml to about 27.5 ml per site per day, between about 27.5 ml to about 30 ml per site per day. According to some embodiments, the first pharmaceutical composition is administered at a volume of about 6 ml per site per day. According to some embodiments, the first pharmaceutical composition is administered at a volume of about 9 ml per site per day. According to some embodiments, the first pharmaceutical composition is administered at a volume of about 4.5 ml per site per day. According to some embodiments, the first pharmaceutical composition is administered at a volume of about 10 ml per site per day. According to some embodiments, the first pharmaceutical composition is administered at a volume of about 5 ml per site per day. According to some embodiments, the first pharmaceutical composition is administered at a volume of about 11 ml per site per day. According to some embodiments, the first pharmaceutical composition is administered at a volume of about 5.5 ml per site per day. According to some embodiments, the first pharmaceutical composition is administered at a volume of about 12 ml per site per day. According to some embodiments, the first pharmaceutical composition is administered at a volume of about 6 ml per site per day.

It is noted that the administration rate may be constant over the course of 24 hours or may change over the course of 24 hours. For instance, according to some embodiments, there may be a certain rate for high activity/day hours and a different rate for low activity/night hours. The high activity/day hours may be, e.g., about 15, about 16, about 17, about 18 or about 19 hours, while the low activity night hours may be about 9, about 8, about 7, about 6 or about 5 hours, respectively. According to some embodiments, the high activity/day rate is implemented for about 18 hours, while the low activity/night rate is implemented for about 6 hours. According to some embodiments, the high activity/day rate is implemented for about 16 hours, while the low activity/night rate is implemented for about 8 hours. According to some embodiments, the administration rate is at least partially determined by input received from the patient, a caregiver, at least one sensor and the like. According to some embodiments, the administration rate may be elevated when necessary or decreased when necessary according to a predefined pattern that may be set periodically, e.g., by a caregiver or the patient. According to other embodiments, the administration rate may be altered, e.g., elevated or decreased, in an on-line manner, for example, according input received from the patient, a caregiver, or at least one sensor, indicating that a change in administration rate is required or beneficial. For instance, if the patient wishes to rest at a certain point during the day, the rate may be decreased from day to night rate, e.g., by a command provided by the patient. In addition, a caregiver may give a command to the system in view of the patient, e.g., resting during the day. Further, a sensor may alert the system that the patient has gone to sleep (or fallen asleep) and decrease the administration rate accordingly. Sensors may also provide sleep pattern data, allowing the system to be notified in advance of the patient awaking from sleep, and in response, e.g., elevating the administration rate. The patient's monitored condition may also cause the administration rate to be altered, e.g., lapsing into an "off episode" and the like, may cause the administration rate to be raised.

The administration rate may be between about 0.01 mL/site/hour to about 1.2 mL/site/hour. According to some embodiments, the administration rate is between about 0.15-1.04 mL/site/hr. According to some embodiments, the administration rate is between about 0.01-0.02 mL/site/hour. According to some embodiments, the administration rate is between about 0.02-0.03 mL/site/hour. According to some embodiments, the administration rate is between about 0.03-0.04 mL/site/hour. According to some embodiments, the administration rate is between about 0.04-0.05 mL/site/hour. According to some embodiments, the administration rate is between about 0.05-0.06 mL/site/hour. According to some embodiments, the administration rate is between about 0.06-0.07 mL/site/hour. According to some embodiments, the administration rate is between about 0.07-0.08 mL/site/hour. According to some embodiments, the administration rate is between about 0.08-0.09 mL/site/hour. According to some embodiments, the administration rate is between about 0.09-0.1 mL/site/hour. According to some embodiments, the administration rate is between about 0.1-0.15 mL/site/hour. According to some embodiments, the administration rate is between about 0.15-0.2 mL/site/hour. According to some embodiments, the administration rate is between about 0.17-0.2 mL/site/hour. According to some embodiments, the administration rate is between about 0.2-0.24 mL/site/hour. According to some embodiments, the administration rate is between about 0.2-0.25 mL/site/hour. According to some embodiments, the administration rate is between about 0.24-0.27 mL/site/hour. According to some embodiments, the administration rate is between about 0.25-0.3 mL/site/hour. According to some embodiments, the administration rate is between about 0.27-0.3 mL/site/hour. According to some embodiments, the administration rate is between about 0.3-0.34 mL/site/hour. According to some embodiments, the administration rate is between about 0.3-0.35 mL/site/hour. According to some embodiments, the administration rate is between about 0.34-0.37 mL/site/hour. According to some embodiments, the administration rate is between about 0.35-0.4 mL/site/hour. According to some embodiments, the administration rate is between about 0.37-0.4 mL/site/hour. According to some embodiments, the administration rate is between about 0.4-0.44 mL/site/hour. According to some embodiments, the administration rate is between about 0.4-0.45 mL/site/hour. According to some embodiments, the administration rate is between about 0.44-0.47 mL/site/hour. According to some embodiments, the administration rate is between about 0.45-0.5 mL/site/hour. According to some embodiments, the administration rate is between about 0.47-0.51 mL/site/hour. According to some embodiments, the administration rate is between about 0.5-0.55 mL/site/hour. According to some embodiments, the administration rate is between about 0.51-0.54 mL/site/hour. According to some embodiments, the administration rate is between about 0.54-0.57 mL/site/hour. According to some embodiments, the administration rate is between about 0.55-0.6 mL/site/hour. According to some embodiments, the administration rate is between about 0.57-0.61 mL/site/hour. According to some embodiments, the administration rate is between about 0.6-0.65 mL/site/hour. According to some embodiments, the administration rate is between about 0.61-0.64 mL/site/hour. According to some embodiments, the administration rate is between about 0.64-0.68 mL/site/hour. According to some embodiments, the administration rate is between about 0.65-0.7 mL/site/hour. According to some embodiments, the administration rate is between about 0.68-0.71 mL/site/hour. According to some embodiments, the administration rate is between about 0.7-0.75 mL/site/hour. According to some embodiments, the administration rate is between about 0.71-0.74 mL/site/hour. According to some embodiments, the administration rate is between about 0.74-0.78 mL/site/hour. According to some embodiments, the administration rate is between about 0.75-0.8 mL/site/hour. According to some embodiments, the administration rate is between about 0.78-0.81 mL/site/hour. According to some embodiments, the administration rate is between about 0.8-0.85 mL/site/hour. According to some embodiments, the administration rate is between about 0.81-0.84 mL/site/hour. According to some embodiments, the administration rate is between about 0.84-0.88 mL/site/hour. According to some embodiments, the administration rate is between about 0.85-0.9 mL/site/hour. According to some embodiments, the administration rate is between about 0.88-0.91 mL/site/hour. According to some embodiments, the administration rate is between about 0.9-0.95 mL/site/hour. According to some embodiments, the administration rate is between about 0.91-0.94 mL/site/hour. According to some embodiments, the administration rate is between about 0.94-0.98 mL/site/hour. According to some embodiments, the administration rate is between about 0.95-1.0 mL/site/hour. According to some embodiments, the administration rate is between about 0.98-1.01 mL/site/hour. According to some embodiments, the administration rate is between about 1.0-1.05 mL/site/hour. According to some embodiments, the administration rate is between about 1.01-1.04 mL/site/hour. According to some embodiments, the administration rate is about 1.04 mL/site/hour. According to some embodiments, the administration rate is between about 1.05-1.1 mL/site/hour. According to some embodiments, the administration rate is between about 1.1-1.15 mL/site/hour. According to some embodiments, the administration rate is between about 1.15-1.2 mL/site/hour.

According to some embodiments, the administration rate in the low activity/night hours is between about 0.01-0.15 mL/site/hour. According to some embodiments, the administration rate in the low activity/night hours is between about 0.01-0.02 mL/site/hour. According to some embodiments, the administration rate in the low activity/night hours is between about 0.02-0.03 mL/site/hour. According to some embodiments, the administration rate in the low activity/night hours is between about 0.03-0.04 mL/site/hour. According to some embodiments, the administration rate in the low activity/night hours is between about 0.04-0.05 mL/site/hour. According to some embodiments, the administration rate in the low activity/night hours is between about 0.05-0.06 mL/site/hour. According to some embodiments, the administration rate in the low activity/night hours is between about 0.06-0.07 mL/site/hour. According to some embodiments, the administration rate in the low activity/night hours is between about 0.07-0.08 mL/site/hour. According to some embodiments, the administration rate in the low activity/night hours is between about 0.08-0.09 mL/site/hour. According to some embodiments, the administration rate in the low activity/night hours is between about 0.09-0.1 mL/site/hour. According to some embodiments, the administration rate in the low activity/night hours is between about 0.1-0.11 mL/site/hour. According to some embodiments, the administration rate in the low activity/night hours is between about 0.11-0.12 mL/site/hour. According to some embodiments, the administration rate in the low activity/night hours is between about 0.12-0.13 mL/site/hour. According to some embodiments, the administration rate in the low activity/night hours is between about 0.13-0.14 mL/site/hour. According to some embodiments, the administration rate in the low activity/night hours is between about 0.14-0.15 mL/site/hour. According to some embodiments, the administration rate in the low activity/night hours is about 0.04 mL/site/hour. According to some embodiments, the administration rate in the low activity/night hours is about 0.08 mL/site/hour.

According to some embodiments, the administration rate in the high activity/day hours is between about 0.15-1.0 mL/site/hour. According to some embodiments, the administration rate in the high activity/day hours is between about 0.15-0.2 mL/site/hour. According to some embodiments, the administration rate in the high activity/day hours is between about 0.2-0.25 mL/site/hour. According to some embodiments, the administration rate in the high activity/day hours is between about 0.25-0.3 mL/site/hour. According to some embodiments, the administration rate in the high activity/day hours is between about 0.3-0.35 mL/site/hour. According to some embodiments, the administration rate in the high activity/day hours is between about 0.35-0.4 mL/site/hour. According to some embodiments, the administration rate in the high activity/day hours is between about 0.4-0.45 mL/site/hour. According to some embodiments, the administration rate in the high activity/day hours is between about 0.45-0.5 mL/site/hour. According to some embodiments, the administration rate in the high activity/day hours is between about 0.5-0.55 mL/site/hour. According to some embodiments, the administration rate in the high activity/day hours is between about 0.55-0.6 mL/site/hour. According to some embodiments, the administration rate in the high activity/day hours is between about 0.6-0.65 mL/site/hour. According to some embodiments, the administration rate in the high activity/day hours is between about 0.65-0.7 mL/site/hour. According to some embodiments, the administration rate in the high activity/day hours is between about 0.7-0.75 mL/site/hour. According to some embodiments, the administration rate in the high activity/day hours is between about 0.75-0.8 mL/site/hour. According to some embodiments, the administration rate in the high activity/day hours is between about 0.8-0.85 mL/site/hour. According to some embodiments, the administration rate in the high activity/day hours is between about 0.85-0.9 mL/site/hour. According to some embodiments, the administration rate in the high activity/day hours is between about 0.9-0.95 mL/site/hour. According to some embodiments, the administration rate in the high activity/day hours is between about 0.95-1.0 mL/site/hour. According to some embodiments, the administration rate in the high activity/day hours is between about 1.0-1.05 mL/site/hour. According to some embodiments, the administration rate in the high activity/day hours is between about 1.05-1.1 mL/site/hour. According to some embodiments, the administration rate in the high activity/day hours is between about 1.1-1.15 mL/site/hour. According to some embodiments, the administration rate in the high activity/day hours is between about 1.15-1.2 mL/site/hour. According to some embodiments, the administration rate in the high activity/day hours is about 0.32 mL/site/hour. According to some embodiments, the administration rate in the high activity/day hours is between about 0.32 mL/hour and about 0.64 mL/hour. According to some embodiments, the administration rate in the high activity/day hours is about 0.64 mL/hour, about 0.59 mL/hour, about 0.55 mL/hour, about 0.5 mL/hour, about 0.45 mL/hour, about 0.41 mL/hour, about 0.36 mL/hour, or about 0.32 mL/hour.

As mentioned above, while the low and high rates are referred to as night and day rates, respectively, they may be used irrespective of the time of day; rather, of the condition of the patient and the like, e.g., low activity and high activity. Further, the rate may be altered gradually, and may be set at any appropriate value, not necessarily bound to one particular high rate and one particular low rate.

According to some embodiments, the first composition is administered over the course of about 12 to about 20 hours (e.g., about 18 hours) at a high activity rate and about 4 to about 12 hours (e.g., about 6 hours) at a low activity rate, wherein about 500 mg to about 800 mg (e.g., about 700 mg or about 691.2 mg) levodopa and about 60 mg to about 100 mg (e.g., about 80 mg or about 86.4 mg) is administered over the course of the high activity and about 20 mg to about 40 mg (e.g., about 30 mg or about 28.8 mg) levodopa and about 2 mg to about 5 mg (e.g., about 3 mg or about 3.6 mg) carbidopa is administered over the course of the low activity. According to some embodiments, the high activity rate and/or the low activity rate may be a consecutive time period in the course of 24 hours. According to other embodiments, the high activity rate and/or the low activity rate may be administered at several, non-consecutive time periods over the course of 24 hours.

It is further noted that the administrated volume and/or administration rate may be constant throughout the treatment, or may vary during different hours of the day, between different days, weeks or months of treatment, and the like. According to some embodiments, the patient is monitored, e.g., independently, by a caretaker, or electronically, e.g., by sensors, possibly found in a dedicated device, e.g., a watch-like device, patch-like sensor, the administration pump, and the like. According to such embodiments, the administration volume and/or rate are determined according to data received from such monitoring.

In certain embodiments, levodopa or a levodopa prodrug is administered over the course of about 12 to about 20 hours (e.g., about 16 hours) at a high activity rate, in an amount to deliver less than about 400 mg, from about 400 mg to about 499 mg, from about 500 mg to about 599 mg, from about 600 mg to about 699 mg, from about 700 mg to about 799 mg, from about 800 mg to about 899 mg, from about 900 mg to about 999 mg, from about 1000 mg to about 1099 mg, from about 1100 mg to about 1199 mg, from about 1200 mg to about 1299 mg, from about 1300 mg to about 1399 mg, from about 1400 mg to about 1499 mg, from about 1500 mg to about 1599 mg, from about 1600 mg to about 1699 mg, from about 1700 mg to about 1799 mg, from about 1800 mg to about 1899 mg, from about 1900 mg to about 1999 mg, from about 2000 mg to about 2099 mg, from about 2100 mg to about 2199 mg, from about 2200 mg to about 2299 mg, from about 2300 mg to about 2399 mg, from about 2400 mg to about 2499 mg, from about 2500 mg to about 2599 mg, from about 2600 mg to about 2699 mg, from about 2700 mg to about 2799 mg, from about 2800 mg to about 2899 mg, from about 2900 mg to about 2999 mg, from about 3000 mg to about 3099 mg, or more than about 3100 mg levodopa, a levodopa prodrug, or a levodopa equivalent to a patient over the course of about 12 to about 20 hours (e.g., about 16 hours).

Some embodiments are directed to a method for administering a bolus subcutaneous injection of the first pharmaceutical composition of the invention. According to some embodiments, the bolus injection comprises between about 0.5 to about 2.0 mL/Kg of the first pharmaceutical composition. According to some embodiments, the bolus injection comprises between about 0.5 to about 0.75 mL/Kg of the first pharmaceutical composition. According to some embodiments, the bolus injection comprises between about 0.75 to about 1.0 mL/Kg of the first pharmaceutical composition. According to some embodiments, the bolus injection comprises between about 1.0 to about 1.25 mL/Kg of the first pharmaceutical composition. According to some embodiments, the bolus injection comprises between about 1.25 to about 1.5 mL/Kg of the first pharmaceutical composition. According to some embodiments, the bolus injection comprises between about 1.5 to about 1.75 mL/Kg of the first pharmaceutical composition. According to some embodiments, the bolus injection comprises between about 1.75 to about 2.0 mL/Kg of the first pharmaceutical composition. According to some embodiments, the bolus injection comprises between about 0.75 to about 1.25 mL/Kg of the first pharmaceutical composition. According to some embodiments, the bolus injection comprises about 1.0 mL/Kg of the first pharmaceutical composition.

The bolus subcutaneous injection may be administered at any time point in relation to any possible continuous subcutaneous administrations, e.g., prior to, during, or after the continuous administration. The bolus subcutaneous injection may be administered at any time point during the day. The bolus subcutaneous injection may be administered once a day, once every two, three, four five or six days, once a week, or more. The bolus subcutaneous injection may be administered when required/desired, according to feedback received from the patient, caretaker, physician, sensors, and the like, and/or according to a predefined regimen. The bolus subcutaneous injection may be administered over between about five minutes to about 40 minutes, between about five minutes to about 10 minutes, between about 10 minutes to 15 minutes, between about 15 minutes to 20 minutes, between about 20 minutes to 25 minutes, between about 25 minutes to 30 minutes, between about 30 minutes to 35 minutes, between about 35 minutes to 40 minutes.

According to some embodiments, the administered dose may be doubled, tripled or more, by using more than one pump, more than one injection site for each pump, and the like.

According to some embodiments, the first pharmaceutical composition is administered for a defined period of time, e.g., days, weeks, months, or years. According to some embodiments, the first pharmaceutical composition is administered endlessly, for the treatment of a chronic condition.

According to some embodiments, the first pharmaceutical composition comprises between about 1% w/v and about 40% w/v of levodopa, a levodopa prodrug, a levodopa salt, or any combination thereof. According to some embodiments, the first pharmaceutical composition comprises between about 1% w/v and about 5% w/v, between about 5% w/v and about 10% w/v, between about 10% w/v and about 15% w/v, between about 15% w/v and about 20% w/v, between about 20% w/v and about 25% w/v, between about 25% w/v and about 30% w/v, between about 30% w/v and about 35% w/v, between about 35% w/v and about 40% w/v, between about 2% w/v and about 10% w/v, between about 4% w/v and about 8% w/v, between about 5% w/v and about 7% w/v, about 6% w/v of levodopa, a levodopa prodrug, a levodopa salt, or any combination thereof.

According to some embodiments, the first pharmaceutical composition comprises between about 0.5% w/v and about 10% w/v of carbidopa, a carbidopa salt, a carbidopa prodrug, or any combination thereof. According to some embodiments, the first pharmaceutical composition comprises between about 0.5% w/v and about 1% w/v, between about 1% w/v and about 1.5% w/v, between about 1.5% w/v and about 2% w/v, between about 2% w/v and about 2.5% w/v, between about 2.5% w/v and about 3% w/v, between about 3% w/v and about 3.5% w/v, between about 3.5% w/v and about 4% w/v, between about 4% w/v and about 4.5% w/v, between about 4.5% w/v and about 5% w/v, between about 5% w/v and about 5.5% w/v, between about 5.5% w/v and about 6% w/v, between about 6% w/v and about 6.5% w/v, between about 6.5% w/v and about 7% w/v, between about 7% w/v and about 7.5% w/v, between about 7.5% w/v and about 8% w/v, between about 8% w/v and about 8.5% w/v, between about 8.5% w/v and about 9% w/v, between about 9% w/v and about 9.5% w/v, between about 9.5% w/v and about 10% w/v, about 0.75% w/v of carbidopa, a carbidopa salt, a carbidopa prodrug, or any combination thereof.

For example, provided herein is a first pharmaceutical composition suitable for parenteral (e.g., subcutaneous) administration, includes about 4-10% by weight levodopa, a levodopa salt, a levodopa prodrug, or any combination thereof, about 0.5 to about 2% by weight carbidopa, a carbidopa salt, a carbidopa prodrug, or any combination thereof, and about 10% to about 20% by weight arginine. Another exemplary first pharmaceutical composition provided herein includes about 6% by weight levodopa, a levodopa salt, a levodopa prodrug, or any combination thereof, about 0.75% by weight carbidopa, a carbidopa salt, a carbidopa prodrug, or any combination thereof, and about 10% to about 20% by weight arginine. According to some embodiments, the arginine may be replaced, at least partially, by lysine.

According to some embodiments, the first pharmaceutical composition comprises between about 0.05% w/v and about 2.0% w/v, between about 0.05% w/v and about 0.1% w/v, between about 0.1% w/v and about 0.2% w/v, between about 0.2% w/v and about 0.3% w/v, between about 0.3% w/v and about 0.4% w/v, between about 0.4% w/v and about 0.5% w/v, between about 0.5% w/v and about 0.6% w/v, between about 0.6% w/v and about 0.7% w/v, between about 0.7% w/v and about 0.8% w/v, between about 0.8% w/v and about 0.9% w/v, between about 0.9% w/v and about 1.0% w/v, between about 1% w/v and about 1.1% w/v, between about 1.1% w/v and about 1.2% w/v, between about 1.2% w/v and about 1.3% w/v, between about 1.3% w/v and about 1.4% w/v, between about 1.4% w/v and about 1.5% w/v, between about 1.5% w/v and about 1.6% w/v, between about 1.6% w/v and about 1.7% w/v, between about 1.7% w/v and about 1.8% w/v, between about 1.8% w/v and about 1.9% w/v, between about 1.9% w/v and about 2.0% w/v, between about 0.75% w/v and about 1.25% w/v, about 0.75% w/v, about 0.8% w/v, about 0.85% w/v, about 0.9% w/v, about 0.95% w/v, about 1.0% w/v of an antioxidant or a combination of antioxidants.

According to some embodiments, the antioxidant is selected from the group consisting of ascorbic acid or a salt thereof, a cysteine, such as N-acetyl cysteine, a bisulfite or a salt thereof, glutathione, a tyrosinase inhibitor, a bivalent cation, butylated hydroxy toluene (BHT), beta hydroxy acid (BHA) tocopherol, gentisic acid, tocopherol, tocopherol derivative, thioglycerol, and any combination thereof. According to some embodiments, the antioxidant is ascorbic acid. According to some embodiments, the antioxidant is N-acetyl cysteine (NAC). According to some embodiments, the first pharmaceutical composition comprises a combination of ascorbic acid and NAC. For example, provided herein is a first pharmaceutical composition, suitable for e.g., subcutaneous administration, that includes about 0.1% to about 10% by weight ascorbic acid or a pharmaceutically acceptable salt thereof, about 0.01% to about 1% by weight of a component selected from the group consisting of: NAC, L-cysteine and pharmaceutically acceptable salts thereof about 2% to about 16% by weight levodopa or an ester thereof and about 0.6% to about 2% by weight carbidopa or an ester thereof.

According to some embodiments, the first pharmaceutical composition comprises a base. According to some embodiments the base is selected from the group consisting of arginine, lysine, NaOH, tris(hydroxymethyl)aminomethane (TRIS), NH$_4$OH, ethylenediamine, diethylamine, ethanolamine, diethanolamine, meglumine, and any combination thereof. According to some embodiments, the base is arginine. According to some embodiments, the base is lysine.

According to some embodiments, the first pharmaceutical composition comprises between about 5% w/v and about 30% w/v or a base. According to some embodiments, the first pharmaceutical composition comprises between about 5% w/v and about 10% w/v, between about 10% w/v and about 15% w/v, between about 15% w/v and about 20% w/v, between about 20% w/v and about 25% w/v, between about 25% w/v and about 30% w/v, between about 12.5% w/v and 17.5% w/v, or about 15% w/v, about 20% w/v, about 25% w/v, about 24% w/v, about 15.2% w/v base.

According to some embodiments, the first pharmaceutical composition further comprises a catechol-O-methyltransferase (COMT) inhibitor. According to some embodiments, the COMT inhibitor is selected from entacapone, tolcapone, opicapone or any combination thereof. According to some embodiments, the first pharmaceutical composition comprises between about 0.1 to about 5.0% w/v of a COMT inhibitor. According to some embodiments, the first pharmaceutical composition comprises between about 0.1 to about 1.0% w/v of a COMT inhibitor. According to some embodiments, the first pharmaceutical composition comprises between about 1.0 to about 2.0% w/v of a COMT inhibitor. According to some embodiments, the first pharmaceutical composition comprises between about 2.0 to about 3.0% w/v of a COMT inhibitor. According to some embodiments, the first pharmaceutical composition comprises between about 3.0 to about 4.0% w/v of a COMT inhibitor. According to some embodiments, the first pharmaceutical composition comprises between about 4.0 to about 5.0% w/v of a COMT inhibitor. According to some embodiments, the first pharmaceutical composition may be administered concomitantly with a COMT inhibitor.

According to some embodiments, the first pharmaceutical composition further comprises a monoamine oxidase (MAO) inhibitor. The MAO inhibitor may be a MAO-A inhibitor or a MAO-B inhibitor. According to some embodiments, the first pharmaceutical composition comprises between about 0.1 to about 5.0% w/v of a MAO inhibitor. According to some embodiments, the first pharmaceutical composition comprises between about 0.1 to about 1.0% w/v of a MAO inhibitor. According to some embodiments, the first pharmaceutical composition comprises between about 1.0 to about 2.0% w/v of a MAO inhibitor. According to some embodiments, the first pharmaceutical composition comprises between about 2.0 to about 3.0% w/v of a MAO inhibitor. According to some embodiments, the first pharmaceutical composition comprises between about 3.0 to about 4.0% w/v of a MAO inhibitor. According to some embodiments, the first pharmaceutical composition comprises between about 4.0 to about 5.0% w/v of a MAO inhibitor. According to some embodiments, the MAO inhibitor is selected from moclobemide, rasagiline, selegiline, safinamide, or any combination thereof. According to some embodiments, the first pharmaceutical composition may be administered concomitantly with a MAO inhibitor.

According to some embodiments, the first pharmaceutical composition comprises a surfactant. According to some embodiments, the surfactant is selected from Tween-80, Tween-60, Tween-40, Tween-20, Tween-65, Tween-85, Span 20, Span 40, Span 60, Span 80, Span 85, polyoxyl 35 castor oil (Cremophor EL), polyoxyethylene hydroxystearate (macrogol 660), or Poloxamer 188 (Pluronic® F-68), or any combination thereof. The first pharmaceutical composition of the invention may include between about 0.1 to about 3.0% w/v of a surfactant or combination of two or more surfactants. According to some embodiments, the first pharmaceutical composition comprises between about 0.1 to about 0.2% w/v, between about 0.2 to about 0.3% w/v, between about 0.3 to about 0.4% w/v, between about 0.4 to about 0.5% w/v, between about 0.5 to about 0.6% w/v, between about 0.6 to about 0.7% w/v, between about 0.7 to about 0.8% w/v, between about 0.8 to about 0.9% w/v, between about 0.9 to about 1.0% w/v, between about 1.0 to about 1.5% w/v, between about 1.5 to about 2.0% w/v, between about 2.0 to about 2.5% w/v, between about 2.5 to about 3.0% w/v of a surfactant or combination of two or more surfactants.

The first pharmaceutical composition may further comprise an additional pharmaceutically acceptable excipient, such as N-methylpyrrolidone (NMP), polyvinylpyrrolidone (PVP), propylene glycol, a preservative, a pharmaceutically acceptable vehicle, a stabilizer, a dispersing agent, a suspending agent, an amino sugar, a calcium chelator, protease inhibitors, or any combination thereof. The first pharmaceutical composition of the invention may comprise between about 5.0 to about 80.0% w/v or an additional pharmaceutically acceptable excipient, e.g., a solvent, such as NMP or a buffer or any other co-solvent. For example, provided here in, is a pharmaceutically acceptable first composition that includes about 6% by weight levodopa, about 0.75% by weight carbidopa, about 10% to about 20% by weight arginine, about 0.5% by weight of L-cysteine or NAC, and/or about 0.5% by weight ascorbic acid or a salt thereof. An exemplary pharmaceutical first composition (e.g., formulation A) may include about 6% by weight levodopa, about 0.75% by weight carbidopa, and about 14% to about 16% by weight arginine. Another exemplary pharmaceutical composition may include about 6% by weight levodopa, about 0.75% by weight carbidopa, about 14% to about 16% by weight arginine, about 0.5% ascorbic acid and about 0.5% NAC.

According to some embodiments, the first pharmaceutical composition of the invention comprises between about 5.0 to about 10.0% w/v, between about 10.0 to about 15.0% w/v, between about 15.0 to about 20.0% w/v, between about 20.0 to about 25.0% w/v, between about 25.0 to about 30.0% w/v, between about 30.0 to about 35.0% w/v, between about 35.0 to about 40.0% w/v, between about 40.0 to about 45.0% w/v, between about 45.0 to about 50.0% w/v, between about 50.0 to about 55.0% w/v, between about 55.0 to about 60.0% w/v, between about 60.0 to about 65.0% w/v, between about 65.0 to about 70.0% w/v, between about 70.0 to about 75.0% w/v, between about 75.0 to about 80.0% w/v of a solvent, e.g., NMP, a buffer or any other co-solvent.

According to some embodiments, the first pharmaceutical composition further comprises a buffer. According to some embodiments, the buffer is selected from citrate buffer, citric acid buffer, sodium acetate buffer, acetic acid buffer, tartaric acid buffer, phosphate buffer, succinic acid buffer, Tris buffer, glycine buffer, hydrochloric acid buffer, potassium hydrogen phthalate buffer, sodium buffer, sodium citrate tartrate buffer, sodium hydroxide buffer, sodium dihydrogen phosphate buffer, disodium hydrogen phosphate buffer, tromethamine (TRIS), or any combination thereof. The first pharmaceutical composition may comprise between about 0.1 to about 30.0% w/v of a buffer. According to some embodiments, the first pharmaceutical composition comprises between about 0.1 to about 1.0% w/v, between about 1.0 to about 2.0% w/v, between about 2.0 to about 3.0% w/v, between about 3.0 to about 4.0% w/v, between about 4.0 to about 5.0% w/v, between about 5.0 to about 6.0% w/v, between about 6.0 to about 7.0% w/v, between about 8.0 to about 9.0% w/v, between about 9.0 to about 10.0% w/v, between about 10.0 to about 15.0% w/v, between about 15.0 to about 20.0% w/v, between about 20.0 to about 25.0% w/v, between about 25.0 to about 30.0% w/v of a buffer.

According to some embodiments, the first pharmaceutical compositions further comprises an acid or a base, e.g., in order to provide a composition with a pre-defined pH. According to some embodiments, the acid is selected from HCl, HBr, methanesulfonic acid, ascorbic acid, acetic acid, citric acid, or any combination thereof. According to some embodiments, the base is selected from NaOH, $Ca(OH)_2$, ammonium hydroxide, arginine, lysine, magnesium hydroxide, potassium hydroxide, meglumine, tromethamine (TRIS), triethylamine, diisopropylethylamine, diazabicycloundecene or any combination thereof. The first pharmaceutical compositions may comprise between about 0.1 to about 30.0% w/v of a base or acid. According to some embodiments, the first pharmaceutical composition comprises between about 0.1 to about 1.0% w/v, between about 1.0 to about 2.0% w/v, between about 2.0 to about 3.0% w/v, between about 3.0 to about 4.0% w/v, between about 4.0 to about 5.0% w/v, between about 5.0 to about 6.0% w/v, between about 6.0 to about 7.0% w/v, between about 8.0 to about 9.0% w/v, between about 9.0 to about 10.0, between about 10.0 to about 11.0, between about 11.0 to about 12.0, between about 12.0 to about 13.0, between about 13.0 to about 14.0, between about 14.0 to about 15.0, between about 15.0 to about 16.0, between about 16.0 to about 17.0, between about 17.0 to about 18.0, between about 18.0 to about 19.0, between about 19.0 to about 20.0, between about 20.0 to about 21.0, between about 21.0 to about 22.0, between about 22.0 to about 23.0, between about 23.0 to about 24.0, between about 24.0 to about 25.0, between about 25.0 to about 26.0, between about 26.0 to about 27.0, between about 27.0 to about 28.0, between about 28.0 to about 29.0, between about 29.0 to about 30.0, of a base or acid.

It is noted that any one, or any combination, of any of the components disclosed herein may be added to the liquid pharmaceutical composition of the invention.

The pH of the first pharmaceutical composition of the invention may be between about 4.5 to about 10 at about 25° C. According to some embodiments, the pH of the first pharmaceutical compositions is between about 4.5 to about 5 at about 25° C. According to some embodiments, the pH of the first pharmaceutical compositions is between about 5 to about 6 at about 25° C. According to some embodiments, the pH of the first pharmaceutical compositions is between about 6 to about 7 at about 25° C. According to some embodiments, the pH of the first pharmaceutical compositions is between about 7 to about 8 at about 25° C. According to some embodiments, the pH of the first pharmaceutical compositions is between about 8 to about 9 at about 25° C. According to some embodiments, the pH of the first pharmaceutical compositions is between about 9 to about 10 at about 25° C. According to some embodiments, the pH of the first pharmaceutical compositions is between about 4.5 to about 5.5 at about 25° C. According to some embodiments, the pH of the first pharmaceutical compositions is between about 5.5 to about 6.5 at about 25° C. According to some embodiments, the pH of the first pharmaceutical compositions is between about 6.5 to about 7.5 at about 25° C. According to some embodiments, the pH of the first pharmaceutical compositions is between about 7.5 to about 8.5 at about 25° C. According to some embodiments, the pH of the first pharmaceutical compositions is between about 8.5 to about 9.5 at about 25° C. According to some embodiments, the pH of the first pharmaceutical compositions is between about 9.5 to about 10 at about 25° C. According to some embodiments, the pH of the first pharmaceutical compositions is about 9.5 at about 25° C. According to some embodiments, an acid or a base is added to the first pharmaceutical composition in order to provide a composition with a predefined pH value. According to some embodiments, the acid is selected from HCl, HBr, methanesulfonic acid, ascorbic acid, acetic acid, citric acid, or any combination thereof. According to some embodiments, the base is selected from NaOH, arginine, lysine, an amine base, any of the bases mentioned herein, and any combination thereof.

According to some embodiments, the first pharmaceutical composition comprises the following:

| Formulation Composition | Nominal concentration (mg/ml) |
|---|---|
| LD-Tyrosine | 300.00 |
| Carbidopa | 13.00 |
| L-Arginine | 240.00 |
| EtOH | 155.50 |
| NAC | 10.00 |
| WFI | q.s | wherein the L-arginine may be replaced, at least partially, by lysine. Further, the concentration of the arginine (and/or lysine) may be reduced from 240 mg/ml to about 230 mg/ml, about 220 mg/ml, about 210 mg/ml, about 200 mg/ml, about 190 mg/ml, about 180 mg/ml, about 170 mg/ml, about 160 mg/ml or about 150 mg/ml. In addition, the concentration of the carbidopa may be changed to about 7.5 mg/ml, about 8.0 mg/ml, about 8.5 mg/ml, about 9.0 mg/ml, about 9.5 mg/ml, about 10 mg/ml, about 11 mg/ml, about 12 mg/ml, about 14 mg/ml, or about 15 mg/ml.

According to some embodiments, the second pharmaceutical composition is administered when desired and/or required, e.g., when symptoms from said neurological or movement disorder require such administration, or according to a predefined treatment protocol. The assessment of the timing for administering the second pharmaceutical composition may be performed by a caretaker, a physician, the patient to whom the composition is being administered, or any combination thereof, resulting from consultation and/or joint decision making, and the like. According to some embodiments, a system supported by any type of sensors may provide data for determining the need for administering the second pharmaceutical composition. That data may be delivered to a caretaker, a physician, the patient, or any combination thereof, via any means, such as an electronic device, e.g., a smartphone, dedicated console, tablet, email, dedicated or known application, and the like.

According to some embodiments, the second pharmaceutical composition is administered at predefined times, predefined intervals, or both, set, e.g., according to treatment protocols or according to data received from the patient, caregiver, physician, sensors, and the like. The predetermined times and/or intervals may be reset at any time point, e.g., in view of data received from the patient, caretaker, sensors, physician assessment, and the like.

According to some embodiments, the second pharmaceutical composition is orally administered substantially concurrently with the start of the infusion time course. According to some embodiments, the second pharmaceutical composition is orally administered about 1, 2, 3, 4, or 5 hours after the start of the infusion time course. It is noted that the "start of the infusion time course" may be a daily time, wherein the cycle of the infusion, e.g., when new vials are introduced into the system, when a cartridge is replaced, when an infusion set is replaced, and the like.

According to some embodiments, the orally administered second pharmaceutical composition is a morning oral dose. According to some embodiments, the morning oral dose comprises levodopa, a levodopa salt, a levodopa prodrug, or any combination thereof. According to some embodiments, the morning oral dose includes one of: 25 mg levodopa, 50 mg levodopa, 75 mg levodopa, 95 mg levodopa, 100 mg levodopa, 125 mg levodopa, 145 mg levodopa, 150 mg levodopa, 195 mg levodopa, 200 mg levodopa, 245 mg levodopa, or 250 mg levodopa.

According to some embodiments, the morning oral dose comprises (a) levodopa, a levodopa salt, a levodopa prodrug; (b) a dopa decarboxylase inhibitor (DDCI), a DDCI salt, a DDCI prodrug, or (c) any combination thereof.

According to some embodiments the second pharmaceutical composition is administered up to 20 times a day. According to some embodiments, the second pharmaceutical composition is administered about 1, 2, 3, 4, 5, 6, 7, 8, 9, 10, 11 or 12 times a day. According to some embodiments, the second pharmaceutical composition is administered between about 3 and 7 times a day. According to some embodiments, the second pharmaceutical composition is administered between about 4 and 6 times a day. According to some embodiments, the second pharmaceutical composition is administered at a frequency of between about 30 minutes to about 24 hours. According to some embodiments, the second pharmaceutical composition is administered at a frequency of between about 30 minutes to about one hour, between about one hour to two hours, between about two hours to three hours, between about three hours to about four hours, between about four hours to about five hours, between about five hours to about six hours, between about six hours to seven five hours, between about seven hours to about eight hours, between about eight hours to about nine hours, between about nine hours to about 10 hours, between about 10 hours to about 11 hours, between about 11 hours to about 12 hours, between about 12 hours to about 13 hours, between about 13 hours to about 14 hours, between about 14 hours to about 15 hours, between about 15 hours to about 16 hours, between about 16 hours to about 17 hours, between about 17 hours to about 18 hours, between about 18 hours to about 19 hours, between about 19 hours to about 20 hours, between about 20 hours to about 21 hours, between about 21 hours to about 22 hours, between about 22 hours to about 23 hours, between about 23 hours to about 24 hours.

The intervals between one administration to the next may differ as well, depending, e.g., on the patient's/caretaker's/physician's observations and assessment, on data received from any type of appropriate sensor, on a predefined treatment protocol, any combination thereof, and the like.

According to some embodiments, the administered dose of the levodopa moiety in the second pharmaceutical composition is the same each time it is administered. According to some embodiments, the dose of the levodopa moiety in the second pharmaceutical composition may differ between different administrations. According to some embodiments, the dose of the levodopa moiety in the second pharmaceutical composition is between about 10 mg per day and about 3000 mg per day, between about 10 mg per day and about 50 mg per day, between about 50 mg per day and about 100 mg per day, between about 100 mg per day and about 150 mg per day, between about 150 mg per day and about 250 mg per day, between about 250 mg per day and about 350 mg per day, between about 350 mg per day and about 500 mg per day, between about 500 mg per day and about 750 mg per day, between about 750 mg per day and about 1000 mg per day, between about 1000 mg per day and about 1250 mg per day, between about 1250 mg per day and about 1500 mg per day, between about 1500 mg per day and about 1750 mg per day, between about 1750 mg per day and about 2000 mg per day, between about 2000 mg per day and about 2250 mg per day, between about 2250 mg per day and about 2500 mg per day, between about 2500 mg per day and about 2750 mg per day, or between about 2750 mg per day and about 3000 mg per day. According to some embodiments, the dose of the levodopa moiety in the second pharmaceutical composition is between about 100 mg per day to about 1800 mg per day. According to some embodiments, the dose of the levodopa moiety in the second pharmaceutical composition is between about 350 mg per day to about 700 mg per day.

It is noted that an administered dose is defined according to the time in which the composition is administered to the patient, and therefore, if several tablets, e.g., 4 tablets, each comprising 100 mg of levodopa are administered to the patient at practically the same time, the administered dose of the levodopa in the second pharmaceutical composition would be considered to be 400 mg in such an instance. Further, the dose per day may consist of several administered doses, not necessarily identical to one another, e.g., a patient may be administered 100 mg at 8 am, 200 mg at 10 am, 100 mg at 3 pm and 75 mg at 7 pm, such that the dose of the levodopa moiety in the second pharmaceutical composition would be considered to be 475 mg per day.

According to some embodiments, the dose of the levodopa moiety in the second pharmaceutical composition is between about 10 mg and about 500 mg per administration, between about 10 mg and about 25 mg per administration, between about 25 mg and about 50 mg per administration, between about 50 mg and about 75 mg per administration, between about 75 mg and about 100 mg per administration, between about 100 mg and about 150 mg per administration, between about 150 mg and about 200 mg per administration, between about 200 mg and about 250 mg per administration, between about 250 mg and about 300 mg per administration, between about 300 mg and about 350 mg per administration, between about 350 mg and about 400 mg per administration, between about 400 mg and about 450 mg per administration, between about 450 mg and about 500 mg per administration. According to some embodiments, the dose differs between different administrations. According to other embodiments, the dose remains constant for at least two administrations, e.g., over the course of 24 hours, three days, one week, and the like.

In certain embodiments, the dose of the levodopa moiety in the second pharmaceutical composition is about 50 mg, 75 mg, 100 mg, 125 mg, 150 mg, 200 mg, or 250 mg levodopa, e.g., in an immediate release tablet or capsule. According to some embodiments, the dose of the levodopa moiety in the second pharmaceutical composition is about 95 mg, about 145 mg, about 195 mg, or about 245 mg levodopa, e.g., in an extended release form, e.g., a tablet or capsule.

As mentioned above, the levodopa moiety in the second pharmaceutical composition may be levodopa, a levodopa salt, a levodopa prodrug or any combination thereof. According to some embodiments, the levodopa moiety in the second pharmaceutical composition is levodopa. According to some embodiments, the levodopa moiety in the second pharmaceutical composition is a levodopa prodrug.

According to some embodiments, the dose of the carbidopa moiety in the second pharmaceutical composition is between about 2.5 mg and about 50 mg per administration, between about 2.5 mg and about 20 mg per administration, between about 2.5 mg and about 25 mg per administration, between about 2.5 mg and about 35 mg per administration, between about 2.5 mg and about 40 mg per administration, between about 15 mg and about 20 mg per administration, between about 15 mg and about 25 mg per administration, between about 15 mg and about 35 mg per administration, between about 15 mg and about 40 mg per administration, between about 15 mg and about 50 mg per administration, between about 20 mg and about 25 mg per administration, between about 20 mg and about 35 mg per administration, between about 20 mg and about 40 mg per administration, between about 20 mg and about 50 mg per administration, between about 25 mg and about 35 mg per administration, between about 25 mg and about 40 mg per administration, between about 25 mg and about 50 mg per administration, between about 35 mg and about 40 mg per administration, between about 35 mg and about 50 mg per administration, between about 40 mg and about 50 mg per administration. According to some embodiments, the dose of carbidopa moiety in the second pharmaceutical composition comprises 2.5 mg, 18.57 mg, 25 mg, 31.25 mg, 37.5 mg or 50 mg carbidopa.

The second pharmaceutical composition may be in any appropriate oral form, such as a pill, hard or soft capsule, tablet, troches, lozenges, aqueous or oily suspensions, dispersible powders or granules, emulsions, syrups or elixirs. The second pharmaceutical composition may an immediate release form, or any type of controlled release form, such as sustained release, extended release, delayed release, prolonged release, and the like. As noted above, the second pharmaceutical composition may comprise at least two active ingredients, e.g., levodopa and carbidopa. It is noted that each one of the active ingredients in the second pharmaceutical composition may be formulated in a different release form, for instance, the levodopa may be in a controlled release form, while the carbidopa is in an immediate release form, or vice versa.

According to some embodiments, the second pharmaceutical formulation is administered only during high activity/waking hours, e.g., during the day, such that the administration intervals are smaller during high activity/waking hours than during other parts of the day, e.g., low activity/night hours. According to further embodiments, the doses of the second pharmaceutical formulation provided during high activity/waking hours are higher than the doses administered during other parts of the day, e.g., low activity/night hours. According to some embodiments, a dosing regimen over 24 hours is devised and may remain constant for a certain number of days, while, within the same day the regimen may be different based on wakefulness, activity, and the like. According to some embodiments, the dosing regimen may change from day to day, as well as within the same day.

Embodiments of the invention are further directed to a method for treatment of a neurological or movement disorder, such as Parkinson's disease, in a patient in need thereof, wherein the method comprises:
parenterally administering a first pharmaceutical composition comprising:
levodopa, a levodopa salt, a levodopa prodrug, or any combination thereof; and
a dopa decarboxylase inhibitor (DDCI), a DDCI salt, a DDCI prodrug, or any combination thereof;
and, concomitantly,
orally administering a morning oral dose composition comprising:
levodopa, a levodopa salt, a levodopa prodrug;
a dopa decarboxylase inhibitor (DDCI), a DDCI salt, a DDCI prodrug; or any combination thereof.

Further embodiments of the invention are directed to a first pharmaceutical composition comprising:
levodopa, a levodopa salt, a levodopa prodrug, or any combination thereof; and
a dopa decarboxylase inhibitor (DDCI), a DDCI salt, a DDCI prodrug, or any combination thereof;
and,
a second pharmaceutical composition comprising:
levodopa, a levodopa salt, a levodopa prodrug;
a dopa decarboxylase inhibitor (DDCI), a DDCI salt, a DDCI prodrug; or any combination thereof,
for use as a combination in the treatment of a neurological or movement disorder, for example, Parkinson's disease, wherein the first pharmaceutical composition is formulated as a parenteral composition and the second pharmaceutical composition is formulated as an oral composition.

Further embodiments of the invention are directed to a kit comprising:
a first pharmaceutical composition in parenteral form comprising:
levodopa, a levodopa salt, a levodopa prodrug, or any combination thereof; and
a dopa decarboxylase inhibitor (DDCI), a DDCI salt, a DDCI prodrug, or any combination thereof,
a second pharmaceutical composition in oral form comprising:
levodopa, a levodopa salt, a levodopa prodrug;
a dopa decarboxylase inhibitor (DDCI), a DDCI salt, a DDCI prodrug; or
any combination thereof; and
instructions for the concomitant administration of the first pharmaceutical composition and the second pharmaceutical composition for the treatment of a neurological or movement disorder, such as Parkinson's disease.

Further embodiments of the invention are directed to a kit comprising:
a first pharmaceutical composition in parenteral form comprising:
levodopa, a levodopa salt, a levodopa prodrug, or any combination thereof; and a dopa decarboxylase inhibitor (DDCI), a DDCI salt, a DDCI prodrug, or any combination thereof; and
instructions for the concomitant administration of the first pharmaceutical composition and a second pharmaceutical composition for the treatment of a neurological or movement disorder, such as Parkinson's disease, wherein the second pharmaceutical composition is provided separately.

Further embodiments of the invention are directed to a method of treating Parkinson's disease in a patient in need thereof, wherein the patient was previously administered a previous form of levodopa other than immediate release carbidopa-levodopa tablets in a ratio of 1:4, and wherein the method comprises:
converting the patient from the previous form of levodopa to oral immediate release levodopa-carbidopa 100/25 mg tablets;
subcutaneously administering to the patient, over a subcutaneous infusion time course of at least about 24 hours or more, a first pharmaceutically acceptable liquid composition comprising levodopa, a levodopa salt, a levodopa prodrug, or any combination thereof; and
orally administering to the patient, before or during the subcutaneous infusion time course, at least one oral dosage form comprising levodopa.

Further embodiments of the invention are directed to a method of treating Parkinson's disease in a patient in need thereof, wherein the patient was previously administered a previous form of levodopa, and wherein the method comprises:
converting the patient from the previous form of levodopa to an oral immediate release levodopa-carbidopa form;
after said conversion, subcutaneously administering to the patient, over a subcutaneous infusion time course of at least about 24 hours or more, a first pharmaceutically acceptable liquid composition comprising levodopa, a levodopa salt, a levodopa prodrug, or any combination thereof; and
orally administering to the patient, before or during the subcutaneous infusion time course, at least one oral dosage form comprising levodopa.

Further embodiments of the invention are directed to a method of treating Parkinson's disease in a patient in need thereof, wherein the patient was previously administered a previous form of levodopa, and wherein the method comprises:
converting the patient from the previous form of levodopa to an oral immediate release levodopa form, thus administering an amount of oral immediate release levodopa to said patient;
following said conversion, subcutaneously administering to the patient, over a subcutaneous infusion time course of at least about 24 hours or more, a first pharmaceutically acceptable liquid composition comprising a subcutaneous amount of levodopa, a levodopa salt, a levodopa prodrug, or any combination thereof, wherein
if the amount of oral immediate release form of levodopa is higher than the subcutaneous amount of levodopa, the amount of oral immediate release form of levodopa is reduced by about the amount of the subcutaneous amount of levodopa, and the patient is administered a remaining amount of oral immediate release levodopa; and
if the amount of oral immediate release form of levodopa is lower than the subcutaneous amount of levodopa, the levodopa salt, the levodopa prodrug, or the combination thereof, the patient is not administered the oral immediate release form of levodopa except for a morning dose of oral immediate release levodopa, administered before or during the subcutaneous infusion time course.

Further embodiments of the invention are directed to a method of treating Parkinson's disease in a patient in need thereof, wherein the patient was previously administered with a previous form of levodopa, and wherein the method comprises:
- converting the patient from the previous form of levodopa to an oral immediate release levodopa form, thus administering an initial daily amount of oral immediate release levodopa to said patient;
- following said conversion, subcutaneously administering to the patient, over a subcutaneous infusion time course of at least about 24 hours or more, a first pharmaceutically acceptable liquid composition in an amount to deliver about 720 mg of levodopa, a levodopa salt, a levodopa prodrug, or any combination thereof, to the patient over the course of at least about 24 hours, wherein
  - if the initial daily amount of oral immediate release form of levodopa is higher than about 700 mg, the amount oral immediate release form of levodopa is reduced by about 700 mg and the patients is administered with a remaining amount of oral immediate release levodopa, equal to the initial daily amount of oral immediate release levodopa minus 700 mg; and
  - if the initial daily amount of amount of oral immediate release form of levodopa is lower than about 700 mg, the patient is administered only with a morning dose of oral immediate release levodopa, administered before or during the subcutaneous infusion time course.

In certain embodiments of the methods described herein, the concomitant administration of the first composition (parenteral, e.g., subcutaneous administration) and the second composition (e.g., oral tablet) to the patient results in a higher area under the curve (AUC) for levodopa from time 0 to the end of the parenteral, e.g., subcutaneous, infusion as compared to the combined AUC for levodopa in the patient when the first composition and the second composition are not concomitantly administered, wherein the total amount of levodopa administered is the same, whether administered concomitantly or non-concomitantly.

Unless explicitly stated, the method embodiments described herein are not constrained to a particular order or sequence. Additionally, some of the described method embodiments or elements thereof can occur or be performed simultaneously, at the same point in time, or concurrently.

It is appreciated that certain features of the invention may also be provided in combination in a single embodiment. Conversely, various elements of the invention that are, for brevity, described in the context of a single embodiment, may also be provided separately or in any suitable subcombination or as suitable in any other described embodiment of the invention. Further, certain features described in the context of various embodiments are not to be considered essential features of those embodiments, unless the embodiment is inoperative without those elements.

Various embodiments and aspects of the present invention as delineated hereinabove and as claimed in the claims section below may be supported by the following examples; however, they are not to be limited by the examples.

EXAMPLES

Example 1

Synergism

A test was run in order to assess the plasma exposure of levodopa (LD) following the coadministration of LD and carbidopa (CD) in both subcutaneous (SC) and oral administrations. Accordingly, results obtained from a combined SC+oral administration were compared to results obtained from SC administration alone and from oral administration alone. An additive plasma exposure and PK profile was expected, i.e., it was expected that the SC+oral coadministration would provide results equal to the additive results of the SC and oral administrations, when each was administered separately.

Methods 16 healthy subjects (18-50 years) were treated in a crossover manner, i.e., sequentially, with a washout period of 6 days between the following two treatments:

Treatment A: A total dose of 180/22.5 mg LD/CD (formulation A) was administered by SC infusion over the course of 8 hours, at a steady infusion rate.

Treatment B: An immediate release (IR) tablet of 100/25 mg LD/CD was administered orally at time 0 h.

Following a 32 hour washout period, the same 16 healthy subjects were administered with LC/CD both orally and subcutaneously according to the following treatment:

Treatment C: A dose of 153.6/19.2 LD/CD (formulation A) was administered by SC infusion over the course of 8 hours, at a steady infusion rate, combined with a single co-administration of an oral IR LD/CD 100/25 mg tablet, 4 hours after the initiation of the infusion. Total LD/CD dose: 253.6/44.2 mg.

Blood samples were collected at the following time points:

Treatment A: 0 (prior to treatment initiation), 0.5 h, 1 h, 2 h, 3 h, 4 h, 5 h, 5.5 h, 6 h, 7 h, 8 h (prior to the end of the infusion).

Treatment B: 0 (prior to treatment initiation), 0.5 h, 1 h, 2 h, 3 h, 4 h.

Treatment C: 0 (prior to treatment initiation), 0.5 h, 1 h, 2 h, 3 h, 4 h, 4.5 h, 5 h, 5.5 h, 6 h, 7 h, 8 h (prior to the end of the infusion).

Results

The normalized $AUC_{0-8}$ of LD and CD of Treatment C, resulting from the combined SC and oral treatment, as described above, was calculated and compared to the sum of the normalized LD and CD AUCs obtained from Treatment A ($AUC_{0-8}$ resulting from 8 h SC infusion) and Treatment B ($AUC_{0-4}$ resulting from one IR oral tablet). The results are presented in the Tables 1 and 2 below.

TABLE 1

Observed .vs. Calculated Ratios of LD AUCs Resulting from SC, Oral, and SC + Oral Treatments

| ID | 1. Treatment A AUC (0-8) × 0.853* | | 2. Treatment B AUC (0-4) | | 3. Combined 1 + 2 [Estimated] | 4. Treatment C AUC (0-8) [Observed] | | Observed (C) Additive Ratio |
|---|---|---|---|---|---|---|---|---|
| 1001 | 2266 | + | 1327 | = | 3593 | 4092 | vs. | 1.139 |
| 1002 | 2218 | + | 1434 | = | 3652 | 3961 | vs. | 1.085 |

TABLE 1-continued

Observed .vs. Calculated Ratios of LD AUCs Resulting from SC, Oral, and SC + Oral Treatments

| ID | 1. Treatment A AUC (0-8) × 0.853* | | 2. Treatment B AUC (0-4) | | 3. Combined 1 + 2 [Estimated] | 4. Treatment C AUC (0-8) [Observed] | | Observed (C) Additive Ratio |
|---|---|---|---|---|---|---|---|---|
| 1003 | 2620 | + | 1752 | = | 4372 | 5136 | vs. | 1.175 |
| 1004 | 1729 | + | 919 | = | 2648 | 3508 | vs. | 1.325 |
| 1005 | 2031 | + | 969 | = | 3000 | 4105 | vs. | 1.368 |
| 1006 | 2693 | + | 1885 | = | 4578 | 6325 | vs. | 1.382 |
| 1008 | 2603 | + | 986 | = | 3589 | 5031 | vs. | 1.402 |
| 1009 | 1920 | + | 1167 | = | 3087 | 3889 | vs. | 1.260 |
| 1010 | 2575 | + | 1375 | = | 3950 | 4175 | vs. | 1.057 |
| 1011 | 3686 | + | 2658 | = | 6344 | 7678 | vs. | 1.210 |
| 1012 | 2310 | + | 1419 | = | 3729 | 4772 | vs. | 1.280 |
| 1013 | 3087 | + | 1799 | = | 4886 | 5620 | vs. | 1.150 |
| 1014 | 2196 | + | 1426 | = | 3622 | 5059 | vs. | 1.397 |
| 1015 | 2629 | + | 1812 | = | 4441 | 5861 | vs. | 1.320 |
| 1016 | 2236 | + | 1837 | = | 4073 | 4610 | vs. | 1.132 |
| Geomean Individual | | | | | | | | 1.240 |
| Geomean Group | 2412 | + | 1458 | = | 3870 | 4817 | vs. | 1.245 |

*Treatment A AUC multiplied by 0.853 in order to provide a dose equal to the subcutaneous dose of Treatment C. It is noted in this respect that previous studies (not shown) proved the dose proportionality of subcutaneous levodopa and carbidopa, and therefore, comparison between doses is by linear normalization.

TABLE 2

Observed .vs. Calculated Ratios of CD AUCs Resulting from SC, Oral, and SC + Oral Treatments

| ID | 1. Treatment A AUC (0-8) × 0.853* | | 2. Treatment B AUC (0-4) | | 3. Combined 1 + 2 [Estimated] | 4. Treatment C AUC (0-8) [Observed] | | Observed (C) Additive Ratio |
|---|---|---|---|---|---|---|---|---|
| 1001 | 850 | + | 256 | = | 1106 | 917 | vs. | 0.829 |
| 1002 | 827 | + | 290 | = | 1117 | 973 | vs. | 0.871 |
| 1003 | 925 | + | 266 | = | 1191 | 1086 | vs. | 0.912 |
| 1004 | 773 | + | 219 | = | 992 | 1000 | vs. | 1.008 |
| 1005 | 942 | + | 246 | = | 1188 | 1181 | vs. | 0.994 |
| 1006 | 955 | + | 322 | = | 1277 | 1218 | vs. | 0.954 |
| 1008 | 988 | + | 349 | = | 1337 | 1047 | vs. | 0.783 |
| 1009 | 657 | + | 318 | = | 975 | 754 | vs. | 0.773 |
| 1010 | 880 | + | 322 | = | 1202 | 995 | vs. | 0.828 |
| 1011 | 1231 | + | 513 | = | 1744 | 1358 | vs. | 0.779 |
| 1012 | 855 | + | 300 | = | 1155 | 868 | vs. | 0.752 |
| 1013 | 1017 | + | 459 | = | 1476 | 1200 | vs. | 0.813 |
| 1014 | 770 | + | 297 | = | 1067 | 1152 | vs. | 1.080 |
| 1015 | 1120 | + | 252 | = | 1372 | 1255 | vs. | 0.915 |
| 1016 | 859 | + | 351 | = | 1210 | 936 | vs. | 0.774 |
| Geomean Individual | | | | | | | | 0.866 |
| Geomean Group | 900 | + | 309 | = | 1209 | 1051 | vs. | 0.869 |

*Treatment A AUC multiplied by 0.853 in order to provide a dose equal to the subcutaneous dose of Treatment C. It is noted in this respect that previous studies (not shown) proved the dose proportionality of subcutaneous levodopa and carbidopa, and therefore, comparison between doses is by linear normalization.

It was expected that the combined/additive results of Treatments A and B (combined, i.e., added to one another), would be practically the same as the results obtained from Treatment C, which essentially combines Treatments A and B within its treatment regime.

Surprisingly, as presented in the results above, the comparison of the Treatment C normalized $AUC_{0-8}$, with the sum of the normalized AUCs for Treatments A and B, as described above, demonstrated a higher than expected LD AUC, while, in contrast, the CD AUC for Treatment C was lower than expected.

Specifically, as presented in Table 1, the ratio of the LD normalized AUCs resulting from Treatment C, compared to those obtained in Treatments A+B (addition of both to simulate the SC+oral administration in Treatment C) for each individual was above 1.0, with a mean ratio of 1.245, and a range of from 1.057 to 1.402. Further, as presented in Table 2, the ratio of the CD normalized AUCs resulting from Treatment C, compared to those obtained in Treatments A+B, for most individuals was below 1.0, with a mean ratio of 0.869 and a range of from 0.773 to 1.080.

Thus, surprisingly, the combined SC+oral treatment provides LD levels higher than expected from the addition of the two types of administrations, when each is provided separately. In contrast, the CD levels obtained from the combined SC+oral treatment are lower than expected from the addition of the two types of administrations, when each is provided separately. The low CD results obtained in the combined treatment render the higher than expected LD levels even more surprising—even though the amount of CD is reduced, the amount of LD actually rises, which is opposite than what would have been expected, since generally, the CD inhibits the peripheral metabolism of LD and therefore, the lower the amount of CD, the lower the expected amount of LD would be.

Example 2

Dose Proportionality

Example 2a

Dose proportionality of LD and CD administered subcutaneously was demonstrated in a clinical trial (ND0612-001, a single dose, single-center, randomized, double-blind, placebo controlled, dose escalation study in healthy male subjects).

Subjects were administered with a composition comprising LD (6% w/w)/CD (1.4% w/w) by way of a 24 hour continuous infusion at varying infusion rates:
Group 1: 80 µl/h
Group 2: 120 µl/h
Group 3: 160 µl/h
Group 4: 200 µl/h
Group 5: 240 µl/h
Several PK parameters were derived for both LD and CD in the dose proportionality assessment, including AUC (hr*ng/mL), Cmax (ng/mL), C15 (ng/mL), and C24 (ng/mL).

All analyses performed for all PK parameters studied demonstrated dose proportionality for both LD and CD. Reference is made to FIG. 1, which presents the mean plasma levodopa concentration of the five tested groups. vs. the time (in hours) after subcutaneous infusion initiation. As clearly shown in FIG. 1, the levodopa plasma levels are dependent on the administered dose of levodopa and are proportional to one another. Similar results were obtained for carbidopa.

Example 2b

Figure 2:
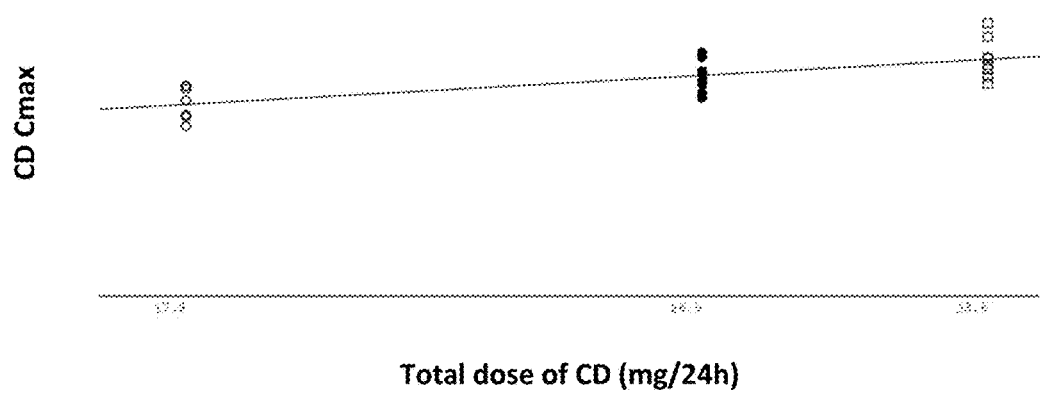
FIG. 2 provides a graph showing Cmax carbidopa values obtained from the subcutaneous administration of three different administered carbidopa concentrations.

In a separate clinical trial (ND0612-005a and ND0612-005b, open label design studies), the plasma carbidopa levels were tested in view of the subcutaneous administration of several carbidopa doses. Three formulations, comprising 60 mg/ml levodopa and (a) 7.5 mg/ml; (b) 6 mg/ml; or 4 mg/ml of carbidopa, were administered to three groups of subjects over the course of 24 hours, providing a total of 17.9 mg/24 h carbidopa to each subject in the first group, 26.9 mg/24 h carbidopa to each subject in the second group and 33.6 mg/24 h carbidopa to each subject in the third group. The obtained carbidopa Cmax values showed clear dose proportionality (see FIG. 2).

Example 3

Pharmacokinetics (PK) of Levodopa (LD) Following SC Administration of a LD Prodrug Concomitantly with the Oral Administration of LD The objective of this study was to determine the pharmacokinetics (PK) of levodopa (LD) in domestic pigs following continuous subcutaneous (SC) infusion of a levodopa prodrug, exemplified using LD-Tyr, administered concomitantly with oral Levodopa.

Table 3 provides the LD-Tyr formulation tested in this study:

TABLE 3

LD-Tyr/CD 300/13 mg/ml Solution:
Formulation Composition

| Formulation Composition | Nominal concentration (mg/ml) |
| --- | --- |
| LD-Tyrosine | 300.00 |
| Carbidopa | 13.00 |
| L-Arginine | 240.00 |
| EtOH | 155.50 |
| NAC | 10.00 |
| WFI | q.s |

Experimental Procedure
Study Design

The study consisted of 3 dosing sessions in which 5 female pigs (Swine/Landrace×large White, ~40-50 kg each) were treated with the LD-Tyr solution of Table 3 and/or Sinemet IR oral tablets (CD/LD 25/100 mg tablet) in a cross-over design with up to 4-day washout period between dosing sessions, as detailed in the following tables:

TABLE 4

Allocation to treatment groups and dosing regimen

| n= | Group Code | | Treatment | Total Dose (mg) | Route | Infusion rate (µL/hrs) | Infusion volume per site (mL) | Infusion duration (hrs) | No. of tablets per day |
| --- | --- | --- | --- | --- | --- | --- | --- | --- | --- |
| 5 | G1 | TI I | LD-Tyr/CD 300/13 mg/mL | LD-Tyr/CD 600/26 | SC | 250 | 2 | 8 | — |
| 5 | G2 | TI II | LD/CD 100/25 mg | LD/CD 300/75 | PO | — | — | — | 3 (Every 4 hrs, first test at time 0) |
| 5 | G3 | TI I + TI II | LD-Tyr/CD 300/13 mg/mL LD/CD 100/25 mg | LD-Tyr/CD 600/26 LD/CD 200/50 | SC PO | 250 — | 2 — | 8 — | — 2 (4 and 8 hrs post infusion initiation) |

TABLE 5

Treatment Design

| Study Day | Animal ND-111 | Animal ND-112 | Animal ND-113 | Animal ND-114 | Animal ND-115 |
|---|---|---|---|---|---|
| 0 | | | Gr2 | | |
| 3 | | | Gr1 | | |
| 4 | | | Pumps removal | | |
| 8 | | | Gr3 | | |
| 9 | | | Pumps removal | | |

The day number indicates the day on which the Test Items (TI) was administered. Day 0 corresponds to the first day of dosing.

As presented in Tables 4 and 5 above, the study included the following three test groups:
G1—received only SC LD-Tyr (600 mg total daily dose);
G2—received only oral LD (300 mg total daily dose); and
G3—received both SC LD-Tyr (600 mg total daily dose) and oral LD (200 mg total daily dose).

Pharmacokinetics

Blood Collection

Blood samples for the determination of LD-Tyr (in groups 1 and 3), as well as LD and CD plasma levels (in all groups) were collected from the pigs at the following timepoints:
0 (pre-dose), 30 min, 1 h, 2 h, 3 h, 4 h, 4.5 h, 5 h, 6 h, 7 h, 8 h, 8.5 h, 9 h, 10 h, 11 h, 13 h, 15 h 18 h following treatment initiation. In case of pump occlusion (groups 1 and 3) resulting in infusion cessation, no further blood samples will be collected. Tablets were administrated before blood collection (time 0, 4 and 8 h).

Bioanalysis

Plasma samples were analyzed for concentration of LD-Tyr (groups 1 and 3), as well as LD and CD (for all groups) using a qualified LC-MS/MS analytical method.

Pharmacokinetic Evaluation

PK parameters (at least $C_{max}$, $t_{max}$, $t_{1/2}$, AUC) for LD-Tyr, LD and CD were calculated by noncompartmental methods using appropriate software (e.g. Phoenix® WinNonlin®). Individual and mean was calculated for quantitative parameters.

Results

The LD AUC of all three test groups was calculated and is presented in Table 6 below. It is noted that the LD AUC resulting from the SC treatment of LD-Tyr is a result of the in-vivo dissociation of the LD-Tyr to LD and tyrosine. The LD exposure obtained from the SC infusion is considered to be the baseline. Therefore, the additional exposure obtained in G3, on top of what would have been obtained from the SC treatment alone (as obtained in G1), is calculated both according to the predicted values and according to the actual results according to the following formulae:

1) Oral on top of SC [[actual]]=G3 (actual results)−G1 (actual results); and
2) Oral on top of SC [[predicted]]=⅔*G2 (the multiplication by ⅔ is required for normalization since G2 received a daily dose of 300 mg, while the oral add-ons in G3 amounted to a daily dose of 200 mg).

TABLE 6

| Animal | SC treatment AUC (G1) Actual | 300 mg Oral AUC (G2) Actual | SC & 200 mg Oral AUC (G3) Predicted | SC & 200 mg Oral AUC (G3) Actual | Calculated AUC of Oral add-ons, on top of SC treatment Predicted* | Calculated AUC of Oral add-ons, on top of SC treatment Actual | Synergism ratio | |
|---|---|---|---|---|---|---|---|---|
| 111 | 19100 | 7590 | 24160 | 30000 | 5060 | 10900 | 2.15 | |
| 112 | 18000 | 9380 | 24253 | 25100 | 6253 | 7100 | 1.14 | |
| 113 | 17600 | 10700 | 24733 | 29900 | 7133 | 12300 | 1.72 | |
| 114 | 19700 | 5230 | 23187 | 24100 | 3487 | 4400 | 1.26 | |
| 115 | 17500 | 6790 | 22027 | 18700 | 4527 | 1200 | 0.27 | Excluded** |
| | | | | | | | 1.49 | Median |
| | | | | | | | 1.57 | Mean |
| | | | | | | | 0.47 | SD |
| | | | | | | | 0.46 | 95% CI (+/−) |
| | | | | | | | 1.11 | 95% CI LB |
| | | | | | | | 2.02 | 95% CI UB |
| | | | | | | | 0.098 | p-value |

*The predicted AUC obtained by the addition of orals on top of the SC treatment (G3) is calculated according to the AUC obtained from orals alone (G1), normalized in a 2/3 ratio.
**animal 115 was excluded since it clearly is an outlier. According to the actual AUC values obtained in all three groups, it seems as though this animal did not swallow the LD pills in G3.

It was expected that, after normalization, the exposure resulting from the oral addition to the SC administration (G3) would be additive, i.e., would, at least approximately, be similar to the oral treatment alone (G2). However, as presented in Table 6 above, surprisingly, the predicted values for the oral addition on top of the SC administration are much lower than the actual results.

The ratio between the actual and predicted values is always above 1, starting at 1.14 and reaching as high as 2.15, wherein the mean ratio is 1.57. Accordingly, these results show that the addition of the oral add-ons increases the LD plasma exposure, on top of the LD exposure obtained from SC administration alone, by an average of over 50%. This ratio shows the unexpected synergism between the SC administration and the oral treatment.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about". It should be noted that where particular values are described in the description and claims, unless otherwise stated, the term "about" means that an acceptable error range, e.g., up to 5% or 10%, for the particular value should be assumed.

INCORPORATION BY REFERENCE

The entire contents of all patents, published patent applications, websites, and other references cited herein are hereby expressly incorporated herein in their entireties by reference.

What is claimed is:

1. A method for treatment of Parkinson's disease in a patient in need thereof, said method comprising:
subcutaneously administering to the patient, over a subcutaneous infusion time course of about 24 hours or more, a first pharmaceutically acceptable liquid composition comprising: a levodopa prodrug, and carbidopa or a carbidopa prodrug, where the levodopa prodrug is present in an amount to deliver up to about 4260 mg of levodopa to the patient over the course of about 24 hours; and
orally administering to the patient, before or during the subcutaneous infusion time course, at least one oral dosage form, each comprising levodopa.

2. The method of claim 1, wherein the carbidopa or carbidopa prodrug is administered in an amount to deliver up to about 220-227 mg of carbidopa to the patient over the course of about 24 hours.

3. The method of claim 1, wherein the first pharmaceutically acceptable liquid composition comprises a carbidopa prodrug, and the levodopa prodrug to carbidopa prodrug is present in the composition in a ratio of about 20:1 w/w.

4. The method of claim 1, wherein the first pharmaceutically acceptable liquid composition is administered to the patient at a rate of about 0.15 ml/site/hr to about 1.04 ml/site/hr.

5. The method of claim 1, further comprising administering an extra dose of a levodopa prodrug, wherein the levodopa prodrug is present in an amount to deliver from about 17 mg levodopa to about 51 mg levodopa to the patient.

6. The method of claim 5, wherein the extra dose of levodopa prodrug is present in an amount to deliver about 17 mg, about 25.5 mg, about 34 mg, about 42.5 mg, or about 51 mg of levodopa to the patient.

7. The method of claim 1, further comprising administering a loading dose of a levodopa prodrug, wherein the levodopa prodrug is present in an amount to deliver between about 50 mg to about 500 mg of levodopa to the patient in each loading dose.

8. The method of claim 7, wherein the loading dose is administered subcutaneously.

9. The method of claim 7, wherein the loading dose is administered orally.

10. The method of claim 1, wherein the oral dosage form includes one of: about 50 mg levodopa, about 75 mg levodopa, about 95 mg levodopa, about 100 mg levodopa, about 125 mg levodopa, about 145 mg levodopa, about 150 mg levodopa, about 195 mg levodopa, about 200 mg levodopa, about 245 mg levodopa, or about 250 mg levodopa.

11. The method of claim 1, wherein the oral dosage form further comprises a COMT inhibitor.

12. The method of claim 1, wherein the treatment includes the treatment of motor fluctuations.

13. The method of claim 1, wherein the oral dosage form is a morning oral dose.

14. The method of claim 1, wherein the oral dosage form is a loading dose.

15. A method for treatment of Parkinson's disease in a patient in need thereof, said method comprising:
subcutaneously administering to the patient, over a subcutaneous infusion time course of about 24 hours or more, a first pharmaceutically acceptable liquid composition comprising: a levodopa prodrug, and carbidopa or a carbidopa prodrug, at a volume of between about 1 ml to about 30 ml per site per day to the patient over the course of about 24 hours; and
orally administering to the patient, before or during the subcutaneous infusion time course, at least one oral dosage form, each comprising levodopa.

16. The method of claim 15, wherein the levodopa prodrug is present in an amount to deliver up to about 4260 mg of levodopa to the patient.

17. The method of claim 15, wherein the carbidopa or carbidopa prodrug is present in an amount to deliver up to about 220-227 mg of carbidopa to the patient.

18. The method of claim 15, wherein the first pharmaceutically acceptable liquid composition comprises a carbidopa prodrug and has the levodopa prodrug to carbidopa prodrug in a ratio of about 20:1 w/w.

19. The method of claim 15, wherein the first pharmaceutically acceptable liquid composition is administered at a rate of about 0.15 ml/site/hr to about 1.04 ml/site/hr.

20. The method of claim 15, further comprising administering an extra dose of a levodopa prodrug, wherein the levodopa is present in an amount to deliver from about 17 mg levodopa to about 51 mg levodopa to the patient.

21. The method of claim 20, wherein the extra dose of levodopa prodrug is present in an amount to deliver about 17 mg, about 25.5 mg, about 34 mg, about 42.5 mg, or about 51 mg of levodopa to the patient.

22. The method of claim 15, further comprising administering a loading dose of a levodopa prodrug, wherein the levodopa prodrug is present in an amount to deliver between about 50 mg to about 500 mg of levodopa to the patient in each loading dose.

23. The method of claim 22, wherein the loading dose is administered subcutaneously.

24. The method of claim 22, wherein the loading dose is administered orally.

25. The method of claim 15, wherein the oral dosage form includes one of: about 50 mg levodopa, about 75 mg levodopa, about 95 mg levodopa, about 100 mg levodopa, about 125 mg levodopa, about 145 mg levodopa, about 150 mg levodopa, about 195 mg levodopa, about 200 mg levodopa, about 245 mg levodopa, or about 250 mg levodopa.

26. The method of claim 15, wherein the oral dosage form further comprises a COMT inhibitor.

27. The method of claim 15, wherein the treatment includes the treatment of motor fluctuations.

28. The method of claim 15, wherein the oral dosage form is a morning oral dose.

29. The method of claim 15, wherein the oral dosage form is a loading dose.

* * * * *